(12) United States Patent
Matsuura et al.

(10) Patent No.: US 10,184,078 B2
(45) Date of Patent: Jan. 22, 2019

(54) ORGANIC ELECTROLUMINESCENT DEVICE

(71) Applicant: Samsung Display Co., Ltd., Yongin-si, Gyeonggi-do (KR)

(72) Inventors: Toshiyuki Matsuura, Yokohama (JP); Hiroaki Itoi, Yokohama (JP); Naoya Sakamoto, Yokohama (JP); Nobutaka Akashi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 15/871,070

(22) Filed: Jan. 15, 2018

(65) Prior Publication Data

US 2018/0134951 A1 May 17, 2018

Related U.S. Application Data

(63) Continuation of application No. 14/934,032, filed on Nov. 5, 2015, now Pat. No. 9,902,901.

(30) Foreign Application Priority Data

Nov. 7, 2014 (JP) .................................. 2014-227110
Nov. 7, 2014 (JP) .................................. 2014-227118

(51) Int. Cl.
*C09K 11/00* (2006.01)
*C09K 11/02* (2006.01)
(Continued)

(52) U.S. Cl.
CPC .......... *C09K 11/025* (2013.01); *C07C 211/43* (2013.01); *C07C 211/44* (2013.01);
(Continued)

(58) Field of Classification Search
CPC .............. H01L 51/006; H01L 51/0067; H01L 51/0074; H01L 51/0058; H01L 51/0054;
(Continued)

(56) References Cited

U.S. PATENT DOCUMENTS

2007/0082226 A1 4/2007 Yu
2007/0092753 A1 4/2007 Begley et al.
(Continued)

FOREIGN PATENT DOCUMENTS

EP 2 709 183 A1 3/2014
JP 2002-241352 A 8/2002
(Continued)

*Primary Examiner* — Amanda C. Walke
(74) *Attorney, Agent, or Firm* — Lewis Roca Rothgerber Christie LLP

(57) ABSTRACT

An organic electroluminescent device of which emission life may be improved. The organic electroluminescent device includes an anode, an emission layer, and an anode-side hole transport layer provided between the anode and the emission layer and including an anode-side hole transport material. An electron accepting material is doped in the anode-side hole transport layer. An intermediate hole transport material layer is provided between the anode-side hole transport layer and the emission layer and includes an intermediate hole transport material, and an emission layer-side hole transport layer is provided between the intermediate hole transport material layer and the emission layer and adjacent to the emission layer. The emission layer-side hole transport layer includes an emission layer-side hole transport material represented by the following Formula 1.

(Continued)

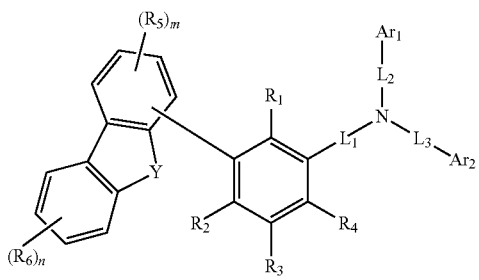

Formula 1

6 Claims, 1 Drawing Sheet

(51) Int. Cl.
| | |
|---|---|
| H01L 51/50 | (2006.01) |
| C07D 403/10 | (2006.01) |
| C07C 211/61 | (2006.01) |
| C07C 211/43 | (2006.01) |
| C07C 211/44 | (2006.01) |
| C07C 211/49 | (2006.01) |
| C07D 401/14 | (2006.01) |
| H01L 51/00 | (2006.01) |

(52) U.S. Cl.
CPC .......... C07C 211/49 (2013.01); C07C 211/61 (2013.01); C07D 401/14 (2013.01); C07D 403/10 (2013.01); H01L 51/5064 (2013.01); H01L 51/0059 (2013.01); H01L 51/0073 (2013.01); H01L 51/0074 (2013.01)

(58) Field of Classification Search
CPC .. C09K 11/025; C07D 401/14; C07D 403/10; C07C 211/61; C07C 211/43; C07C 211/44; C07C 211/49
USPC .......................... 564/426, 431; 428/690, 917
See application file for complete search history.

(56) References Cited

U.S. PATENT DOCUMENTS

| | | |
|---|---|---|
| 2011/0278551 A1 | 11/2011 | Yabunouchi et al. |
| 2011/0278558 A1 | 11/2011 | Hamada |
| 2012/0302762 A1 | 11/2012 | Osaka et al. |
| 2014/0061630 A1 | 3/2014 | Yabunouchi |
| 2015/0270506 A1 | 9/2015 | Voges et al. |
| 2016/0118597 A1 | 4/2016 | Itoi et al. |

FOREIGN PATENT DOCUMENTS

| | | |
|---|---|---|
| JP | 2011-187959 A | 9/2011 |
| JP | 2013-28597 A | 2/2013 |
| KR | 10-2013-0007159 A | 1/2013 |
| WO | WO 2007/105906 A1 | 9/2007 |
| WO | WO 2011/021520 A1 | 2/2011 |

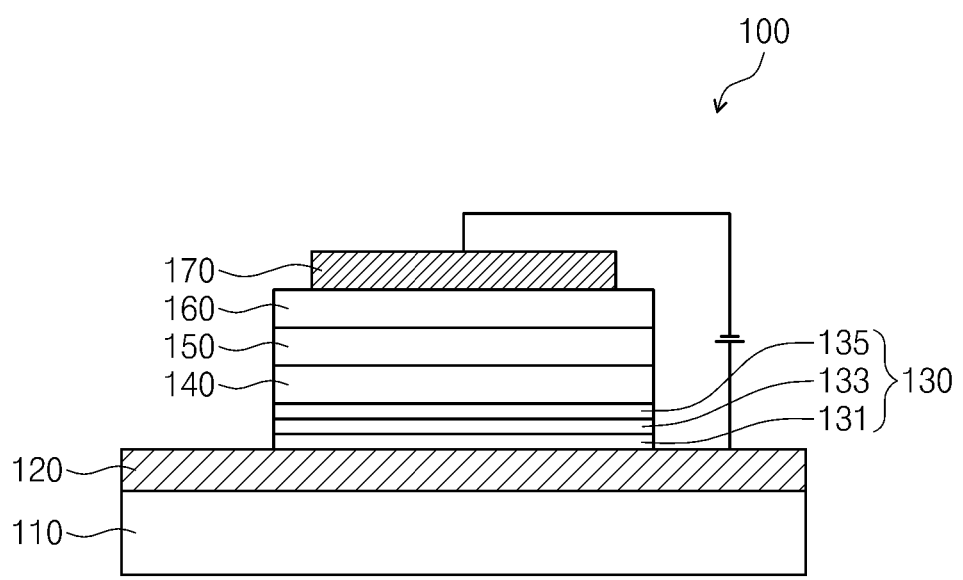

ORGANIC ELECTROLUMINESCENT DEVICE

CROSS-REFERENCE TO RELATED APPLICATIONS

This application is a continuation of U.S. patent application Ser. No. 14/934,032, filed Nov. 5, 2015, which claims priority to and the benefit of Japanese Patent Application Nos. 2014-227110, filed on Nov. 7, 2014, and 2014-227118, filed on Nov. 7, 2014, the entire content of all of which is incorporated herein by reference.

BACKGROUND

The present disclosure herein relates to an organic electroluminescent device.

Recently, the developments of organic electroluminescent (EL) displays are being actively conducted. Also, the developments of organic EL devices, which are self luminescent type emitting devices utilized in the organic EL displays, are being actively conducted.

As the structure of the organic EL device, a stacked structure of, for example, an anode, a hole transport layer, an emission layer, an electron transport layer and a cathode in the stated order has been utilized.

In such organic EL devices, holes and electrons injected from the anode and the cathode recombine in the emission layer to generate excitons. The emission of light may be realized via the transition of the generated excitons to a ground state.

For example, in Patent Documents 1 to 4, technique on a hole transport material or a hole transport layer in an organic EL device is disclosed. For example, a hole transport material utilized in a hole transport layer is disclosed in Patent Document 1. In addition, technique of adding an electron accepting material to a hole transport layer, etc., is disclosed in Patent Document 2, and technique of forming a hole transport layer of a stacked structure utilizing a plurality of layers is disclosed in Patent Documents 3 and 4.

PATENT DOCUMENTS (Patent Document 1) JP2002-241352 A
(Patent Document 2) WO2007-105906 A
(Patent Document 3) KR10-2013-0007159 A
(Patent Document 4) JP2011-187959 A

SUMMARY

However, according to the techniques disclosed in Patent Documents 1 to 4, satisfactory values concerning the emission efficiency and the emission life of an organic EL device could not be obtained, and further improvement thereof is required.

An aspect according to one or more embodiments of the present disclosure, considering the above-described limitation, is directed toward a novel and improved organic EL device having improved emission efficiency and emission life.

According to an embodiment of the present disclosure, an organic EL device includes an anode; an emission layer; an anode-side hole transport layer between the anode and the emission layer, the anode-side hole transport layer including an anode-side hole transport material and doped with an electron accepting material; an intermediate hole transport material layer between the anode-side hole transport layer and the emission layer, the intermediate hole transport material layer including an intermediate hole transport material; and an emission layer-side hole transport layer between the intermediate hole transport material layer and the emission layer, the emission layer-side hole transport layer including an emission layer-side hole transport material represented by Formula 1.

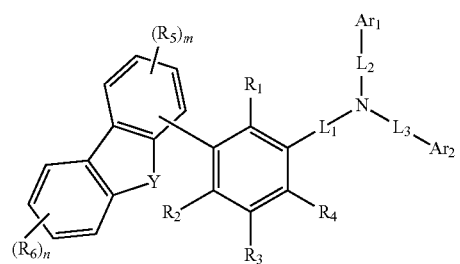

Formula 1

In Formula 1, Y is O or S; $R_1$ to $R_6$ are each independently hydrogen, deuterium, a halogen atom, a substituted or unsubstituted alkyl group having 1 to 15 carbon atoms, a substituted or unsubstituted silyl group, a substituted or unsubstituted aryl group having 6 to 30 carbon atoms for forming a ring, a substituted or unsubstitued heteroaryl group having 1 to 30 carbon atoms for forming a ring, or a substituted or unsubstituted aryl group or heteroaryl group formed via condensation of optional adjacent substituents; $Ar_1$ and $Ar_2$ are each independently a substituted or unsubstituted aryl group having 6 to 50 carbon atoms for forming a ring, or a substituted or unsubstituted heteroaryl group having 5 to 50 carbon atoms for forming a ring; $L_1$ to $L_3$ are each independently a direct linkage, a substituted or unsubstituted alkylene group having 1 to 15 carbon atoms, a substituted or unsubstituted aralkylene group having 7 to 30 carbon atoms, a substituted or unsubstituted arylene group having 6 to 30 carbon atoms for forming a ring, a substituted or unsubstituted heteroarylene group having 1 to 30 carbon atoms for forming a ring, or a substituted or unsubstituted divalent silyl group; m is an integer from 0 to 3; and n is an integer from 0 to 4.

In accordance with this aspect, the emission efficiency and emission life of the organic EL device may be further increased.

In an embodiment, the intermediate hole transport material may be a compound represented by Formula 2.

Formula 2

In Formula 2, $Ar_7$ to $Ar_9$ are each independently a substituted or unsubstituted aryl group having 6 to 50 carbon atoms for forming a ring, or a substituted or unsubstituted heteroaryl group having 5 to 50 carbon atoms for forming a ring; Ar$_{10}$ is hydrogen, deuterium, a halogen atom, a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; and L$_4$ is a direct linkage, a substituted or unsubstituted arylene group having 6 to 18 carbon atoms for forming a ring, or a substituted or unsubstituted heteroarylene group having 5 to 15 carbon atoms for forming a ring.

In accordance with this aspect, the emission efficiency and emission life of the organic EL device may be further increased.

In an embodiment, the electron accepting material may have a lowest unoccupied molecular orbital (LUMO) level within a range from about −9.0 eV to about −4.0 eV.

In accordance with this aspect, the emission efficiency and emission life of the organic EL device may be further increased.

In an embodiment, the anode-side hole transport layer may be adjacent to the anode.

In accordance with this aspect, the emission efficiency and emission life of the organic EL device may be further increased.

In an embodiment, the anode-side hole transport material may be a compound represented by Formula 2.

In accordance with this aspect, the emission efficiency and emission life of the organic EL device may be further increased.

In an embodiment, the emission layer may include a compound represented by Formula 3.

Formula 3

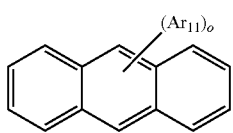

In Formula 3, Ar$_{11}$ is each independently hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group, or a hydroxyl group; and o is an integer from 1 to 10.

In accordance with this aspect, the emission efficiency and emission life of the organic EL device may be further increased.

According to an embodiments of the present disclosure, an organic EL device includes an anode; an emission layer; an anode-side hole transport layer between the anode and the emission layer, the anode-side hole transport layer formed mainly utilizing an electron accepting material; an intermediate hole transport material layer between the anode-side hole transport layer and the emission layer, the intermediate hole transport material layer including an intermediate hole transport material; and an emission layer-side hole transport layer between the intermediate hole transport material layer and the emission layer, the emission layer-side hole transport layer adjacent to the emission layer and including an emission layer-side hole transport material represented by Formula 1.

Formula 1

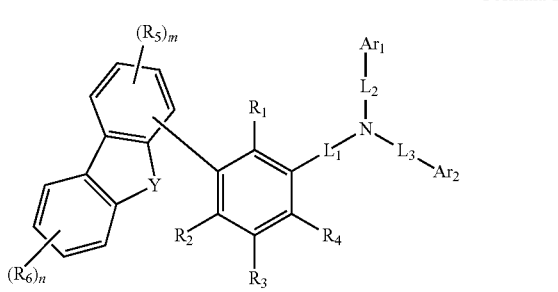

In Formula 1, Y is O or S; R$_1$ to R$_6$ are each independently hydrogen, deuterium, a halogen atom, a substituted or unsubstituted alkyl group having 1 to 15 carbon atoms, a substituted or unsubstituted silyl group, a substituted or unsubstituted aryl group having 6 to 30 carbon atoms for forming a ring, a substituted or unsubstituted heteroaryl group having 1 to 30 carbon atoms for forming a ring, or a substituted or unsubstituted aryl group or heteroaryl group formed via condensation of optional adjacent substituents; Ar$_1$ and Ar$_2$ are each independently a substituted or unsubstituted aryl group having 6 to 30 carbon atoms for forming a ring, or a substituted or unsubstituted heteroaryl group having 1 to 30 carbon atoms for forming a ring; L$_1$ to L$_3$ are each independently a direct linkage, a substituted or unsubstituted alkylene group having 1 to 15 carbon atoms, a substituted or unsubstituted aralkylene group having 7 to 30 carbon atoms, a substituted or unsubstituted arylene group having 6 to 30 carbon atoms for forming a ring, a substituted or unsubstituted heteroarylene group having 1 to 30 carbon atoms for forming a ring, or a substituted or unsubstituted divalent silyl group; m is an integer from 0 to 3; and n is an integer from 0 to 4.

In accordance with this aspect, the driving voltage of the organic EL device may decrease, and the emission efficiency and emission life thereof may be increased.

In some embodiments, the intermediate hole transport material may be a compound represented by Formula 2.

Formula 2

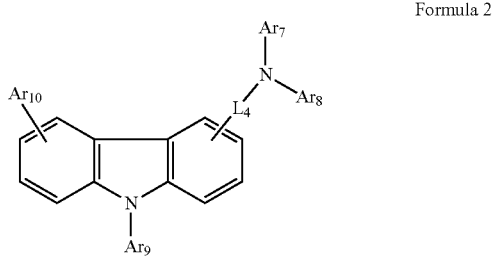

In Formula 2, Ar$_7$ to Ar$_9$ are each independently a substituted or unsubstituted aryl group having 6 to 50 carbon atoms for forming a ring, or a substituted or unsubstituted heteroaryl group having 5 to 50 carbon atoms for forming a ring; $Ar_{10}$ is hydrogen, deuterium, a halogen atom, a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; and $L_4$ is a direct linkage, a substituted or unsubstituted arylene group having 6 to 18 carbon atoms for forming a ring, or a substituted or unsubstituted heteroarylene group having 5 to 15 carbon atoms for forming a ring.

In accordance with this aspect, the driving voltage of the organic EL device may decrease, and the emission efficiency and emission life thereof may be further increased.

In some embodiments, the electron accepting material may have a LUMO level within a range from about −9.0 eV to about −4.0 eV.

In accordance with this aspect, the driving voltage of the organic EL device may decrease further, and the emission efficiency and emission life thereof may be further increased.

In some embodiments, the anode-side hole transport layer may be adjacent to the anode.

In accordance with this aspect, the driving voltage of the organic EL device may decrease further, and the emission efficiency and emission life thereof may be further increased.

In some embodiments, the emission layer may include a compound represented by Formula 3.

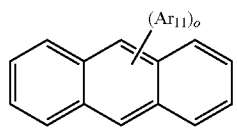

Formula 3

In Formula 3, $Ar_{11}$ is each independently hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group, or a hydroxyl group; and o is an integer from 1 to 10.

In accordance with this aspect, the driving voltage of the organic EL device may decrease further, and the emission efficiency and emission life thereof may be further increased.

BRIEF DESCRIPTION OF THE FIGURE

The accompanying drawing is included to provide a further understanding of the present disclosure, and is incorporated in and constitutes a part of this specification. The drawing illustrates example embodiments of the present disclosure and, together with the description, serves to explain principles of the present disclosure. The drawing is a diagram for explaining the schematic configuration of an organic EL device according to an embodiment.

DETAILED DESCRIPTION

Example embodiments of the present disclosure will be described below in more detail with reference to the accompanying drawing. In the specification and drawing, elements having substantially the same function will be designated by the same reference numerals, and repeated explanation thereof will not be provided.

<1-1. Configuration of Organic EL Device>
(1-1-1. Whole Configuration)

First, on the basis of the drawing, the whole configuration of an organic EL device 100 according to an embodiment of the present disclosure will be described.

As shown in the drawing, an organic EL device 100 according to an embodiment may include a substrate 110, a first electrode 120 disposed on the substrate 110, a hole transport layer 130 disposed on the first electrode 120, an emission layer 140 disposed on the hole transport layer 130, an electron transport layer 150 disposed on the emission layer 140, an electron injection layer 160 disposed on the electron transport layer 150, and a second electrode 170 disposed on the electron injection layer 160. Here, the hole transport layer 130 may be formed to have a multi-layer structure composed of a plurality of layers 131, 133 and 135.

(1-1-2. Configuration of substrate)

The substrate 110 may be a substrate utilized in a common (e.g., an existing) organic EL device. For example, the substrate 110 may be a glass substrate, a semiconductor substrate or a transparent plastic substrate.

(1-1-3. Configuration of First Electrode)

The first electrode 120 may be, for example, an anode, and may be formed on the substrate 110 by an evaporation method, a sputtering method, etc. For example, the first electrode 120 may be formed as a transmission electrode utilizing a metal, an alloy, a conductive compound, etc., having high work function. The first electrode 120 may be formed utilizing, for example, indium tin oxide ($In_2O_3$—$SnO_2$: ITO), indium zinc oxide ($In_2O_3$—ZnO: IZO), tin oxide ($SnO_2$), zinc oxide (ZnO), etc., having good transparency and conductivity. In addition, the first electrode 120 may be formed as a reflection electrode formed by stacking a transparent and conductive layer, such as magnesium (Mg), aluminum (Al), etc.

(1-1-4. Configuration of Hole Transport Layer)

The hole transport layer 130 may include a hole transport material and have hole transporting function. The hole transport layer 130 may be formed, for example, on the first electrode 120 to a layer thickness (total layer thickness in a multi-layer structure) within a range from about 10 nm to about 150 nm.

Here, the hole transport layer 130 of the organic EL device 100 according to an embodiment may be formed as a multi-layer by stacking from the first electrode 120, an anode-side hole transport layer 131, an intermediate hole transport material layer 133 and an emission layer-side hole transport layer 135 one by one. In addition, the ratio of the thicknesses of the layers is not specifically limited.

(1-1-4-1. Configuration of Anode-Side Hole Transport Layer)

The anode-side hole transport layer 131 may be a layer including an anode-side hole transport material and being doped with an electron accepting material. For example, the anode-side hole transport layer 131 may be formed on the first electrode 120.

The anode-side hole transport layer 131 may be doped with the electron accepting material, and hole injection property from the first electrode 120 may be improved. Thus, in one embodiment, the anode-side hole transport layer 131 may be provided near the first electrode 120, and for example, may be provided adjacent to the first electrode 120.

The anode-side hole transport material included in the anode-side hole transport layer 131 may be any suitable hole transport material. Examples of the anode-side hole transport material included in the anode-side hole transport layer 131 may be 1,1-bis[(di-4-tolylamino)phenyl]cyclohexane (TAPC), a carbazole derivative (such as N-phenyl carbazole or polyvinyl carbazole), N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), etc.

The electron accepting material included in the anode-side hole transport layer 131 may be any suitable electron accepting material. However, in one embodiment, the electron accepting material doped in the anode-side hole transport layer 131 may have a LUMO level from about −9.0 eV to about −4.0 eV, and for example, the electron accepting material doped in the anode-side hole transport layer 131 may have the LUMO level from about −6.0 eV to about −4.0 eV.

Here, examples of the electron accepting material having the LUMO level from about −9.0 eV to about −4.0 eV may include the compounds represented by Formulae 4-1 to 4-14.

(4-1)
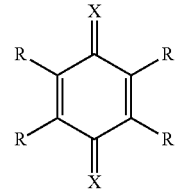

(4-2)
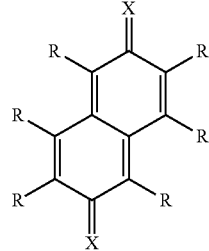

(4-3)
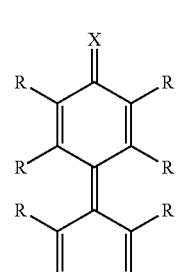

-continued (4-4)
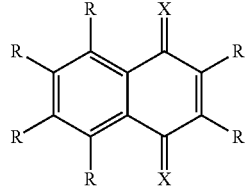

(4-5)
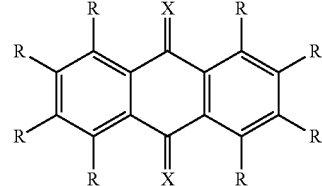

(4-6)
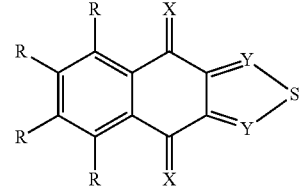

(4-7)
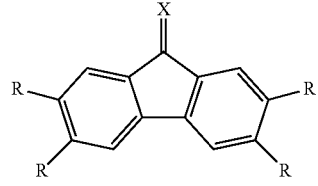

(4-8)
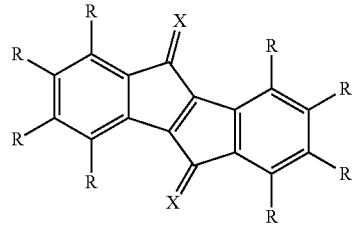

(4-9)
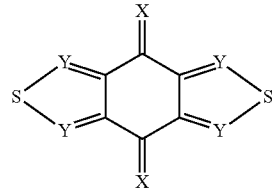

(4-10)
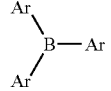

(4-11)
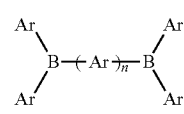

-continued

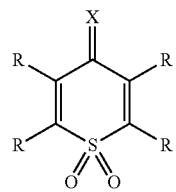
(4-12)

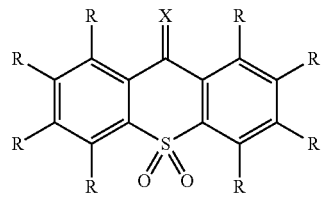
(4-13)

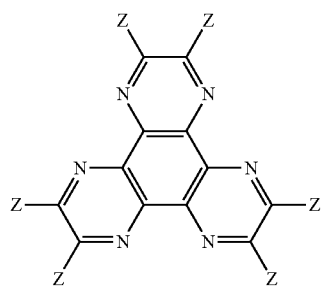
(4-14)

In the above Formulae 4-1 to 4-14, R is hydrogen, deuterium, a halogen atom, a fluoroalkyl group having 1 to 50 carbon atoms, a cyano group, an alkoxy group having 1 to 50 carbon atoms, an alkyl group having 1 to 50 carbon atoms, an aryl group having 6 to 50 carbon atoms or a heteroaryl group having 5 to 50 carbon atoms for forming a ring.

Ar is a substituted with an electron withdrawing group (e.g., a substituted aryl group having 6 to 50 carbon atoms for forming a ring and substituted with an electron withdrawing group) or an unsubstituted aryl group having 6 to 50 carbon atoms for forming a ring, or a substituted or unsubstituted heteroaryl group having 5 to 50 carbon atoms for forming a ring; Y is a methine group (—CH=) or a nitrogen atom (—N=); Z is a pseudohalogen atom or a sulfur (S) atom; n is an integer of 10 and less; and X is one of the substituents represented by the following formulae X1 to X7.

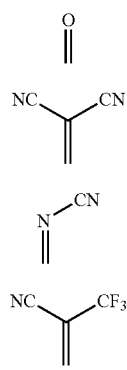

X1

X2

X3

X4

X5

X6

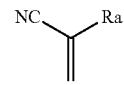
X7

In the above Formulae $X_1$ to $X_7$, Ra is hydrogen, deuterium, a halogen atom, a fluoroalkyl group having 1 to 50 carbon atoms, a cyano group, an alkoxy group having 1 to 50 carbon atoms, an alkyl group having 1 to 50 carbon atoms, a substituted or unsubstituted aryl group having 6 to 50 carbon atoms for forming a ring, or a substituted or unsubstituted heteroaryl group having 5 to 50 carbon atoms for forming a ring.

Examples of the substituted or unsubstituted aryl group having 6 to 50 carbon atoms for forming a ring represented by R, Ar and Ra may include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butyl phenyl group, a p-(1-2-phenylpropyl)phenyl group, a 3-methyl-2-naphthyl group, a 4-methyl-1-naphthyl group, a 4-methyl-1-anthryl group, a 4'-methyl biphenylyl group, a 4"-t-butyl-p-terphenyl-4-yl group, a fluoranthenyl group, a fluorenyl group, etc.

Examples of the substituted or unsubstituted heteroaryl group having 5 to 50 carbon atoms for forming a ring represented by R, Ar and Ra may include a 1-pyrrolyl group, a 2-pyrrolyl group, a 3-pyrrolyl group, a pyridinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(1-2-phenylpropyl) pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, etc.

Examples of the fluoroalkyl group in the substituted or unsubstituted fluoroalkyl group having 1 to 50 carbon atoms represented by R and Ra may include a perfluoroalkyl group (such as a trifluoromethyl group, a pentafluoroethyl group, a heptafluoropropyl group or a heptadecafluorooctane group), a monofluoromethyl group, a difluoromethyl group, a trifluoroethyl group, a tetrafluoropropyl group, an octafluoropentyl group, etc.

Examples of the substituted or unsubstituted alkyl group having 1 to 50 carbon atoms represented by R and Ra may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

The substituted or unsubstituted alkoxy group having 1 to 50 carbon atoms represented by R and Ra may be a group represented by —OY. Examples of Y may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, etc.

Examples of the halogen atom represented by R and Ra may include fluorine (F), chlorine (Cl), bromine (Br), iodine (I), etc.

Here, example compounds of the electron accepting material may include the following Compounds 4-15 and 4-16. For example, the LUMO level of Compound 4-15 may be about −4.40 eV, and the LUMO level of Compound 4-16 may be about −5.20 eV. However, the electron accepting material is not limited to the following Compounds 4-15 and 4-16.

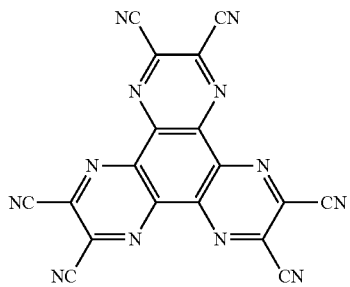

(4-15)

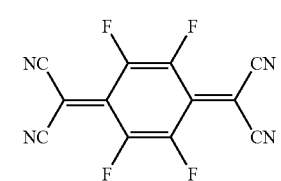

(4-16)

In addition, the amount doped of the electron accepting material may be an amount capable of being doped into the anode-side hole transport layer 131, without any limitation (e.g., the amount of the electron accepting material doped into or included in the anode-side hole transport layer 131 is not particularly limited and may be any suitable amount). For example, the amount doped of the electron accepting material may be from about 0.1 wt % to about 50 wt % on the basis of the total amount of the anode-side hole transport material included in the anode-side hole transport layer 131, and may be from about 0.5 wt % to about 5 wt %.

(1-1-4-2. Configuration of Intermediate Hole Transport Material Layer)

The intermediate hole transport material layer 133 may include an intermediate hole transport material. The intermediate hole transport material layer 133 may be formed, for example, on the anode-side hole transport layer 131.

The intermediate hole transport material included in the intermediate hole transport material layer 133 may be any suitable hole transport material. For example, the intermediate hole transport material may utilize the above-mentioned hole transport materials as the anode-side hole transport materials.

However, in one embodiment, the intermediate hole transport material may be a compound represented by the following Formula 2.

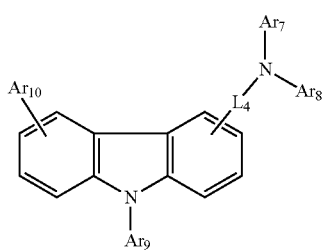

Formula 2

In the above Formula 2, $Ar_7$ to $Ar_9$ are each independently a substituted or unsubstituted aryl group having 6 to 50 carbon atoms for forming a ring or a substituted or unsubstituted heteroaryl group having 5 to 50 carbon atoms for forming a ring; $Ar_{10}$ is hydrogen, deuterium, a halogen atom, a substituted or unsubstituted aryl group having 6 to 50 carbon atoms for forming a ring, a substituted or unsubstituted heteroaryl group having 5 to 50 carbon atoms for forming a ring or a substituted or unsubstituted alkyl group having 1 to 50 carbon atoms; and $L_4$ is a direct linkage, a substituted or unsubstituted arylene group having 6 to 18 carbon atoms for forming a ring or a substituted or unsubstituted heteroarylene group having 5 to 15 carbon atoms for forming a ring.

Examples of $Ar_7$ to $Ar_9$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In one embodiment, examples of $Ar_7$ to $Ar_9$ may include the phenyl group, the biphenyl group, the terphenyl group, the fluorenyl group, the carbazolyl group, the dibenzofuranyl group, etc.

Examples of $Ar_{10}$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In one embodiment, examples of $Ar_{11}$ may include the phenyl group, the biphenyl group, the terphenyl group, the fluorenyl group, the carbazolyl group, the dibenzofuranyl group, etc.

Examples of $L_4$ other than the direct linkage may include a phenylene group, a biphenylene group, a terphenylene group, a naphthylene group, an anthrylene group, a phenanthrylene group, a fluorenylene group, an indenylene group, a pyrenylene group, an acetonaphthenylene group, a fluoranthenylene group, a triphenylenylene group, a pyridylene group, a furanylene group, a pyranylene group, a thienylene group, a quinolylene group, an isoquinolylene group, a benzofuranylene group, a benzothienylene group, an indolylene group, a carbazolylene group, a benzoxazolylene group, a benzothiazolylene group, a kinokisariren group, a benzoimidazolylene group, a pyrazolylene group, a dibenzofuranylene group, a dibenzothienylene group, etc. In one embodiment, $L_4$ may include the direct linkage, the phenylene group, the biphenylene group, the terphenylene group, the fluorenylene group, the carbazolylene group or the dibenzofuranylene group.

Examples of the compound represented by Formula 2 may include the following Compounds 2-1 to 2-17. However, the compound represented by Formula 2 is not limited to the following Compounds 2-1 to 2-17.

Formula 7
(2-1)
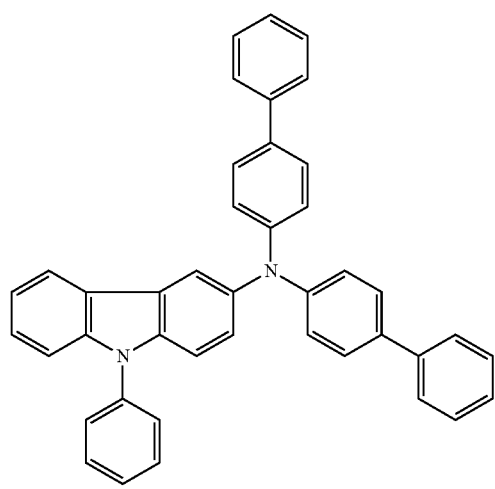
(2-4)
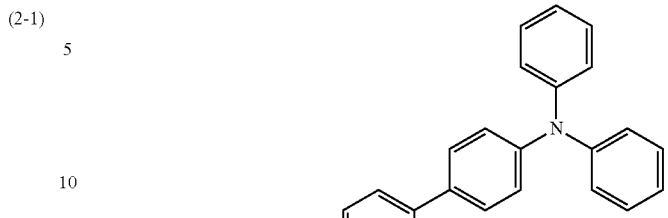
(2-2)
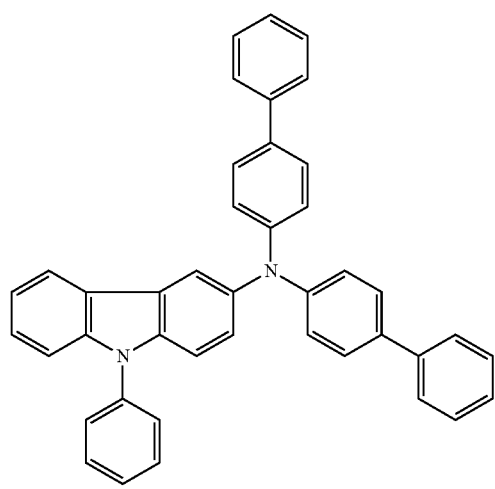
(2-5)
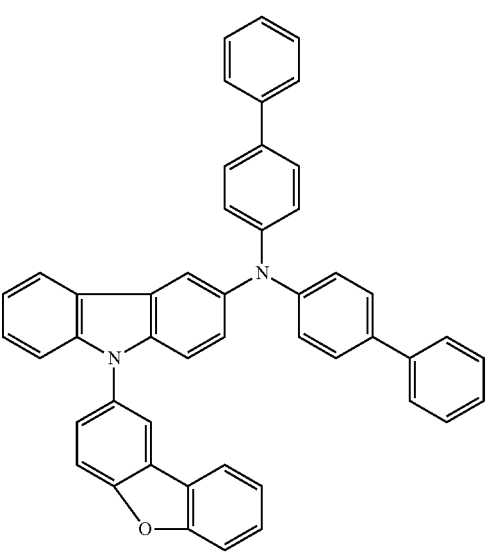
(2-3)
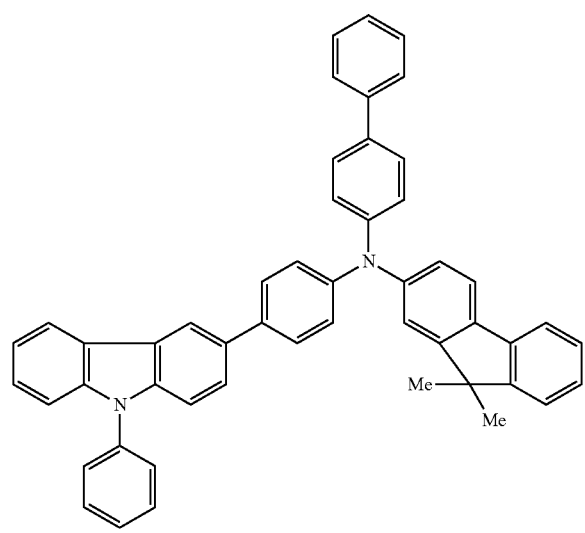
(2-6)
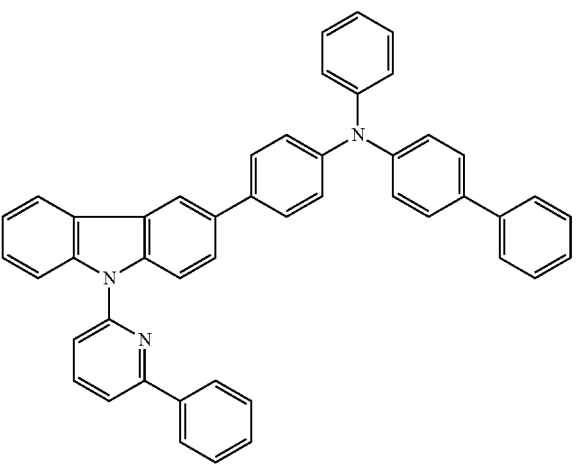

(2-7)
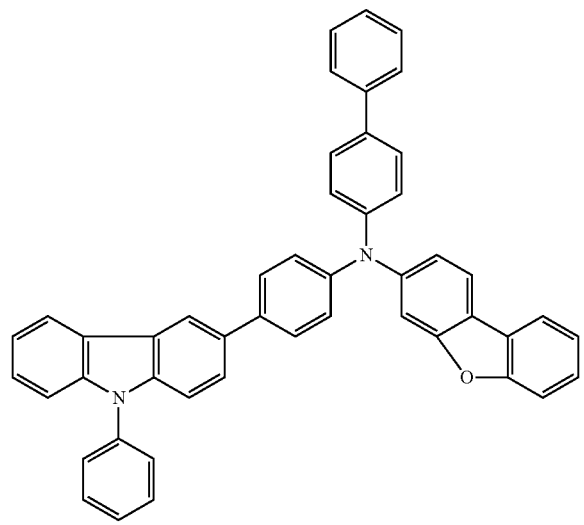
(2-8)
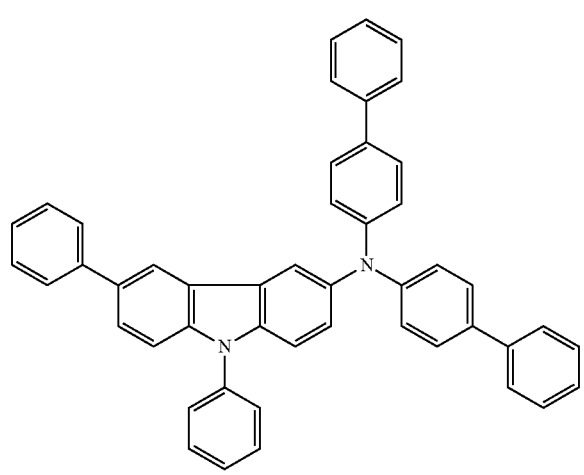
(2-9)
(2-10)
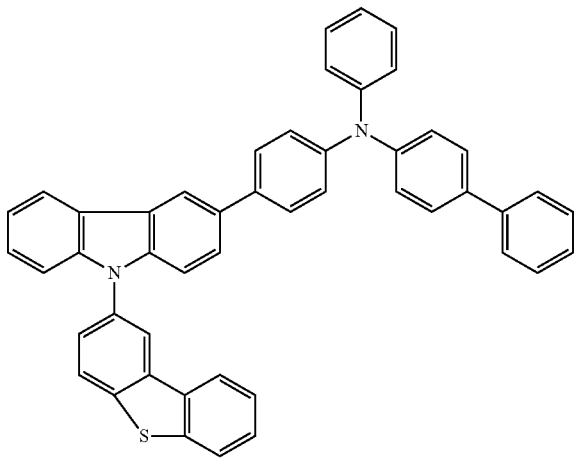
(2-11)
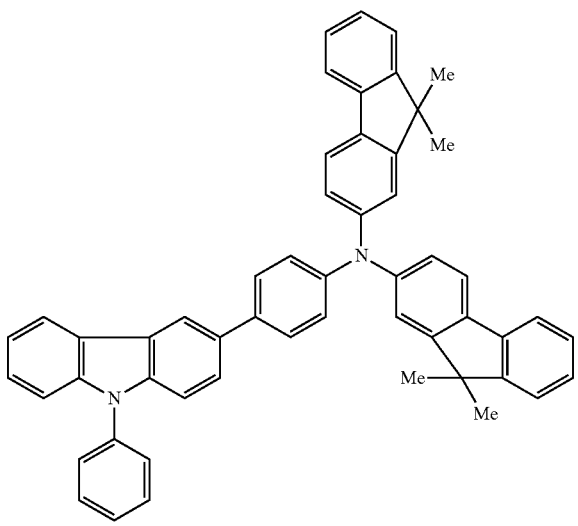
(2-12)
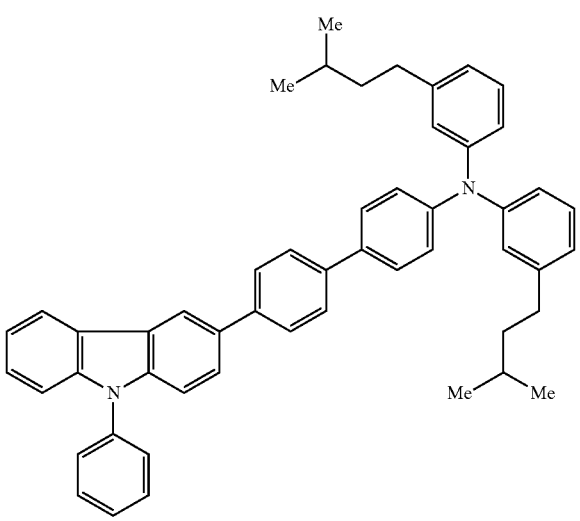

-continued (2-13)

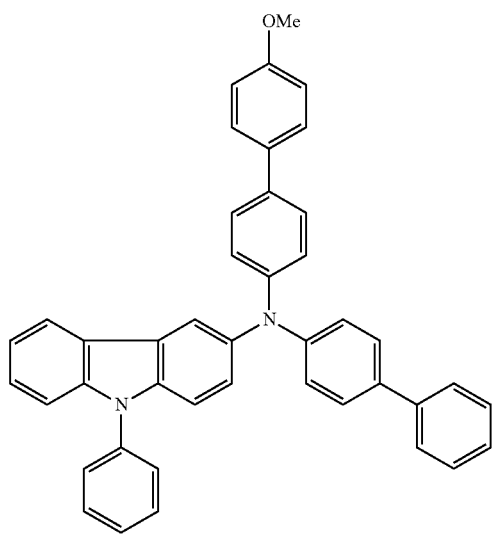

(2-14)

(2-15)

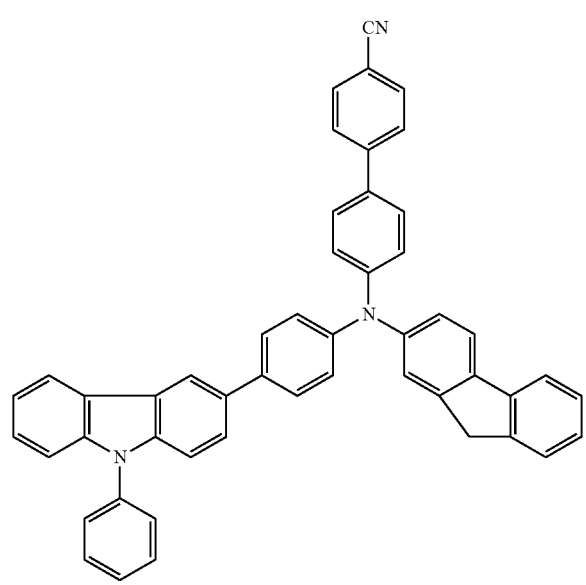

-continued (2-16)

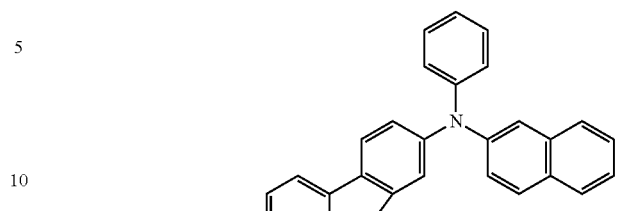

(2-17)

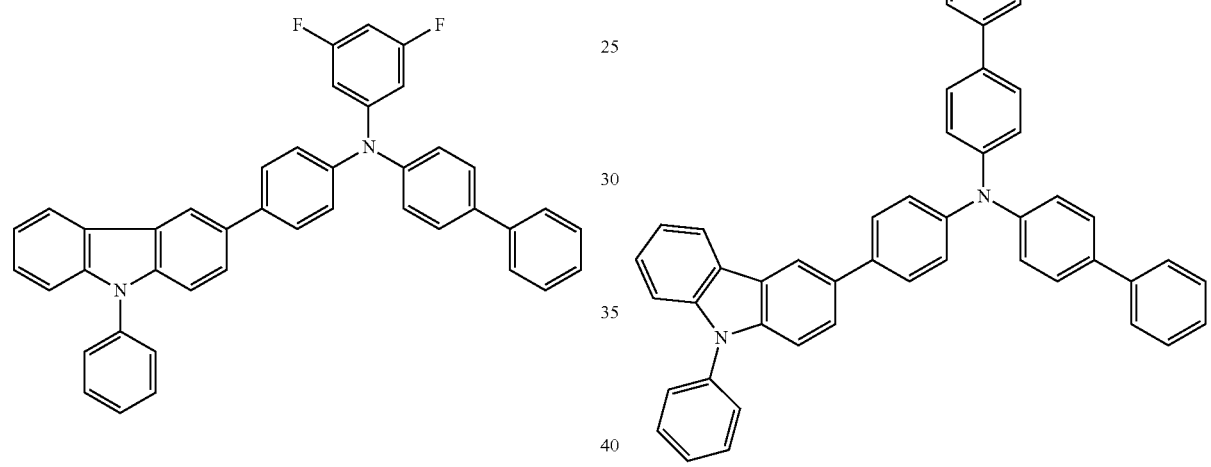

The intermediate hole transport material layer 133 may include the compound represented by the above Formula 2 as the intermediate hole transport material and may improve the hole transporting property of the hole transport layer 130. Thus, the emission efficiency and emission life of the organic EL device 100 may be improved.

In addition, the compound represented by Formula 2 may be included in the anode-side hole transport layer 131 as the anode-side hole transport material. In the case that the anode-side hole transport layer 131 includes the compound represented by Formula 2 as the anode-side hole transport material, the hole transporting property of the hole transport layer 130 may be improved. Thus, the emission efficiency and emission life of the organic EL device 100 may be improved.

(1-1-4-3. Configuration of Emission Layer-Side Hole Transport Layer)

The emission layer-side hole transport layer 135 may include a compound represented by the following Formula 1. The emission layer-side hole transport layer 135 may be formed, for example, on the intermediate hole transport material layer 133, adjacent to the emission layer 140.

Formula 1

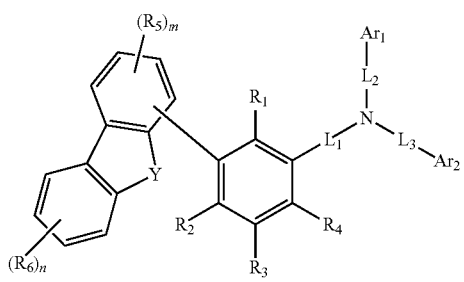

In Formula 1, Y is O or S; $R_1$ to $R_6$ are each independently hydrogen, deuterium, a halogen atom, a substituted or unsubstituted alkyl group having 1 to 15 carbon atoms, a substituted or unsubstituted silyl group, a substituted or unsubstituted aryl group having 6 to 30 carbon atoms for forming a ring, a substituted or unsubstituted heteroaryl group having 1 to 30 carbon atoms for forming a ring, or a substituted or unsubstituted aryl group or heteroaryl group formed via condensation of optional adjacent substituents; $Ar_1$ and $Ar_2$ are each independently a substituted or unsubstituted aryl group having 6 to 30 carbon atoms for forming a ring, or a substituted or unsubstituted heteroaryl group having 1 to 30 carbon atoms for forming a ring; $L_1$ to $L_3$ are each independently a direct linkage, a substituted or unsubstituted alkylene group having 1 to 15 carbon atoms, a substituted or unsubstituted aralkylene group having 7 to 30 carbon atoms, a substituted or unsubstituted arylene group having 6 to 30 carbon atoms for forming a ring, a substituted or unsubstituted heteroarylene group having 1 to 30 carbon atoms for forming a ring, or a substituted or unsubstituted divalent silyl group; m is an integer from 0 to 3; and n is an integer from 0 to 4.

Examples of $R_1$ to $R_6$ may include hydrogen, deuterium, a halogen atom, a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In one embodiment, examples of $R_1$ and $R_6$ may include the hydrogen atom, the halogen atom, the methyl group, the phenyl group, the biphenyl group, the fluorenyl group, the carbazolyl group, and the dibenzofuranyl group.

Examples of $Ar_1$ and $Ar_2$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In one embodiment, examples of $Ar_1$ and $Ar_2$ may include the phenyl group, the biphenyl group, the terphenyl group, the fluorenyl group, the carbazolyl group, the dibenzofuranyl group, etc.

Examples of $L_1$ to $L_3$ other than the direct linkage may be a corresponding divalent substituent of the substituents illustrated in the above $Ar_1$ and $Ar_2$ (e.g., examples of $L_1$ to $L_3$ other than the direct linkage may be a corresponding divalent group of the groups listed above for $Ar_1$ and $Ar_2$). Examples of $L_1$ to $L_3$ other than the direct linkage may include a phenylene group, a naphthylene group, a biphenylene group, a thienothiophenylene group and a pyridylene group. In one embodiment, $L_1$ to $L_3$ may be the direct linkage, the phenylene group or the biphenylene group.

Examples of the compound represented by Formula 1 may include the following Compounds 1 to 48. However, the compound represented by Formula 1 is not limited to the following Compounds 1 to 48.

Formula 8

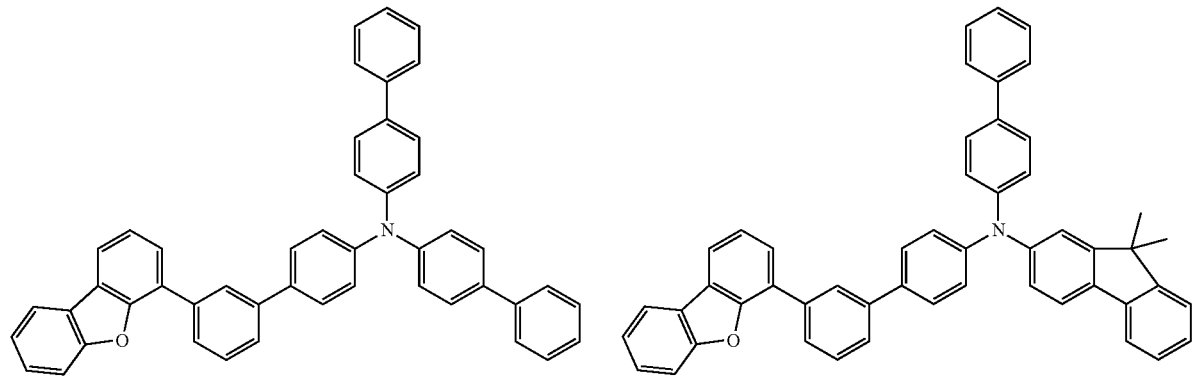

1          2

-continued
3
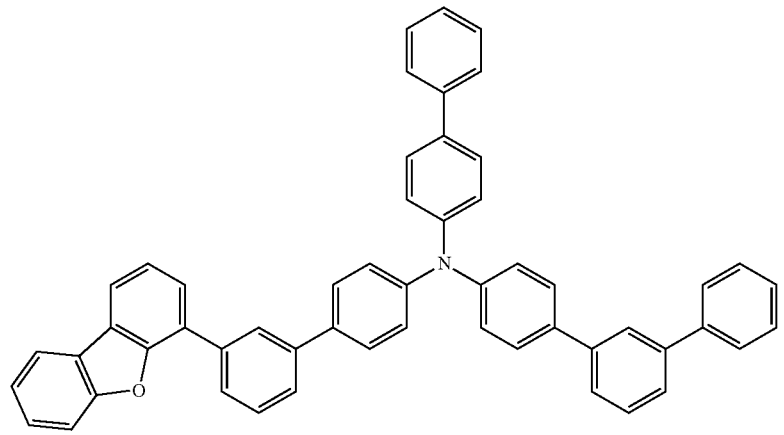
4
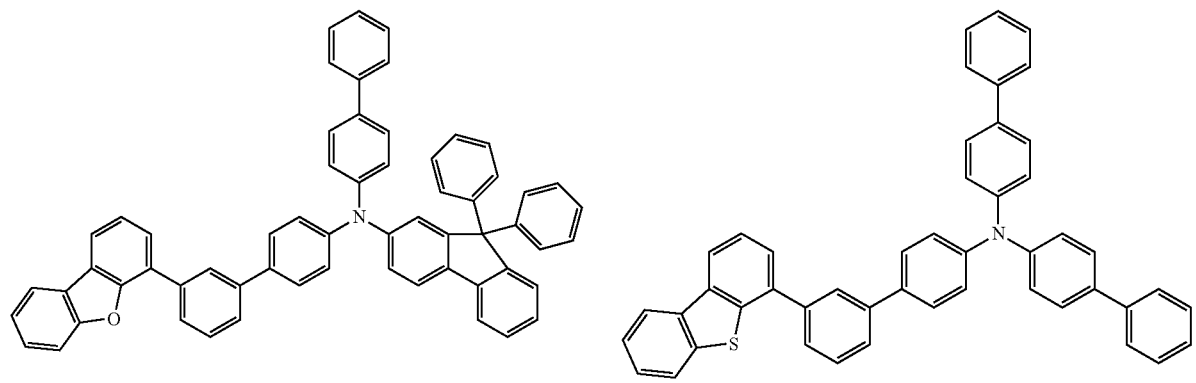
5
6
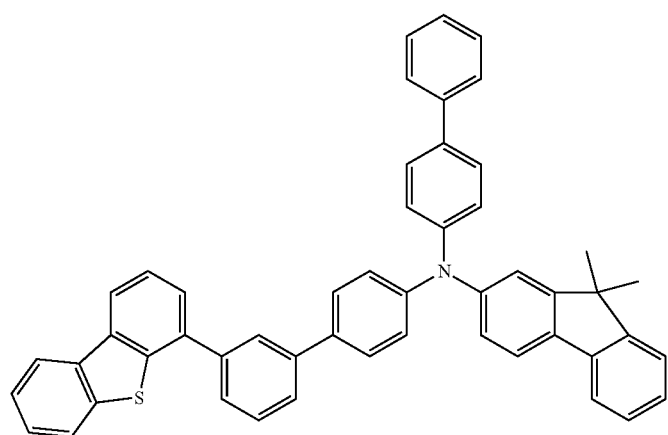

-continued
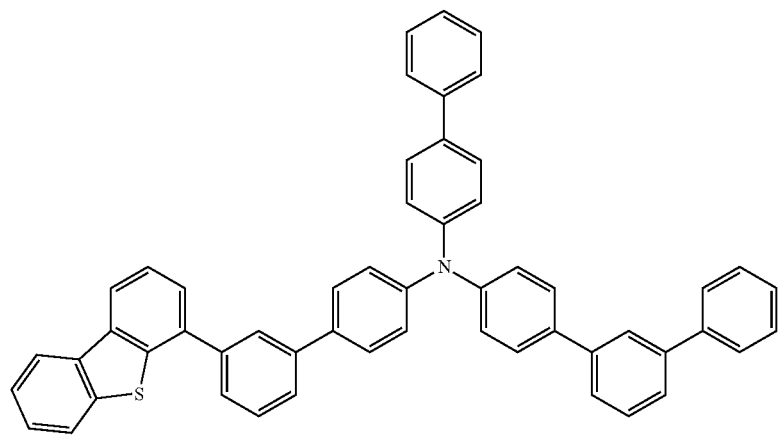
7
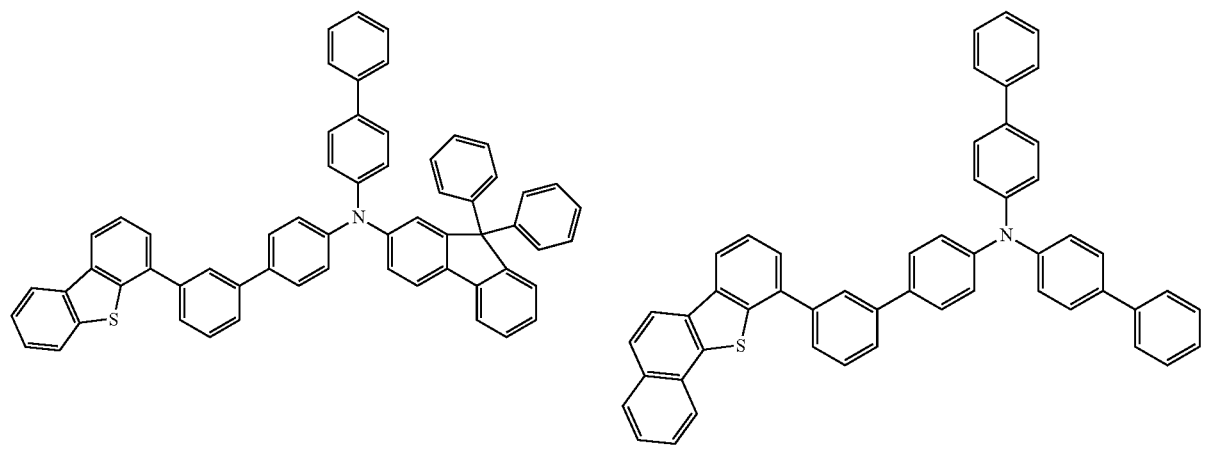
8 9
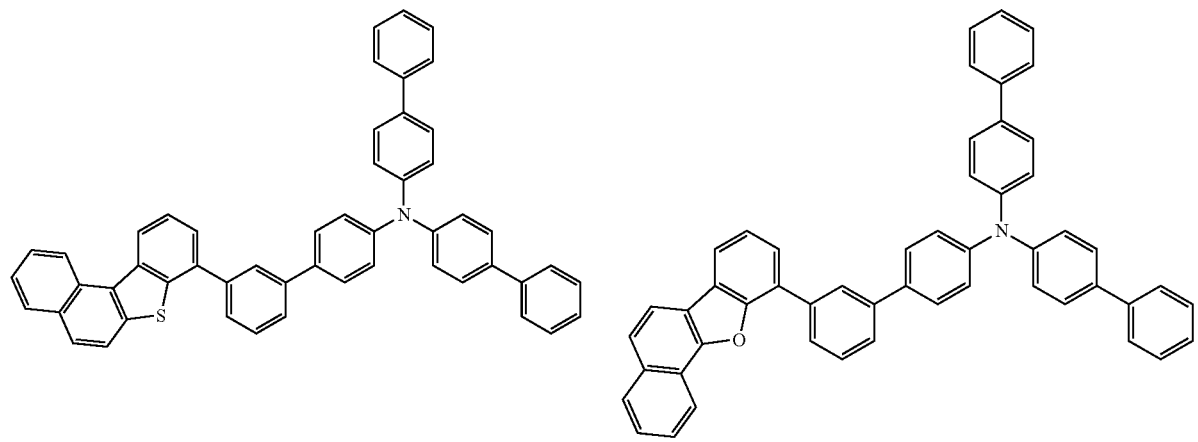
10 11

-continued
12
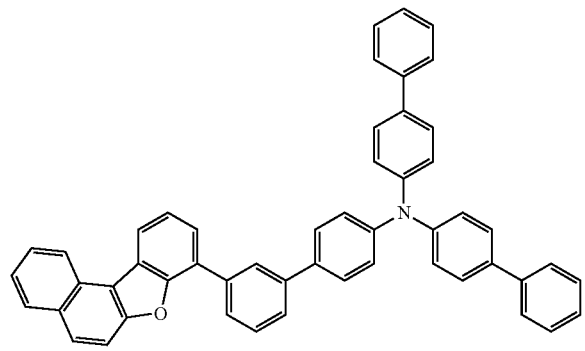
13
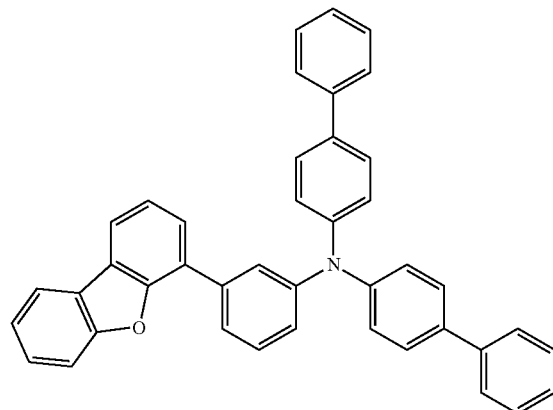
14
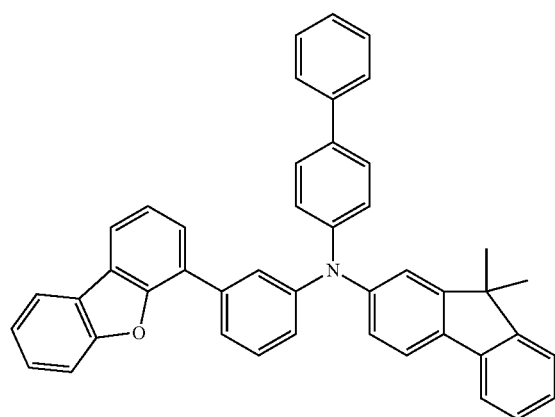
15
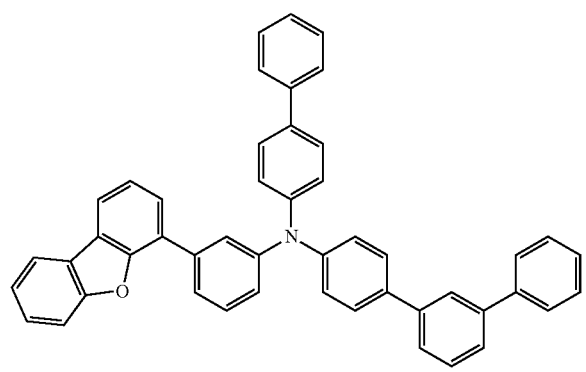
16
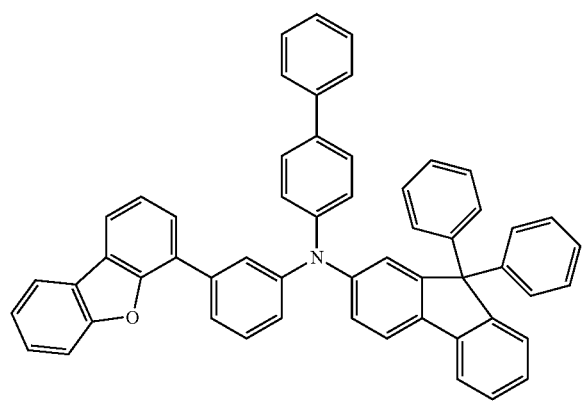
17
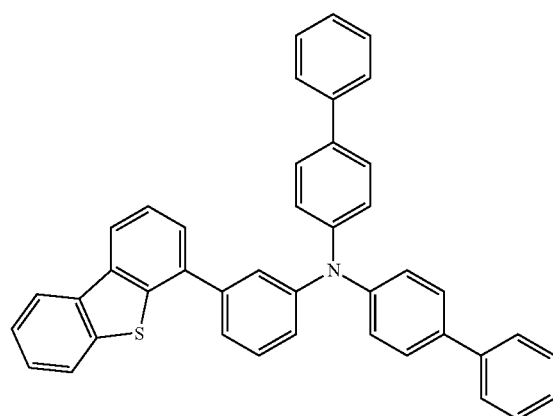

-continued
18
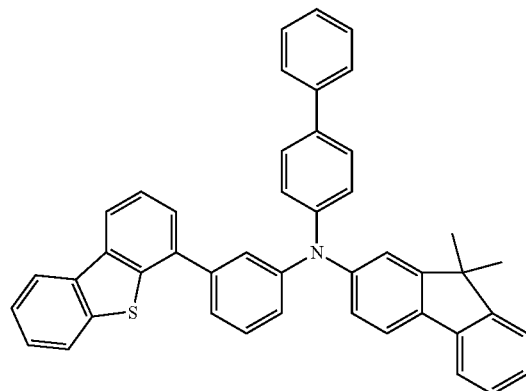
19
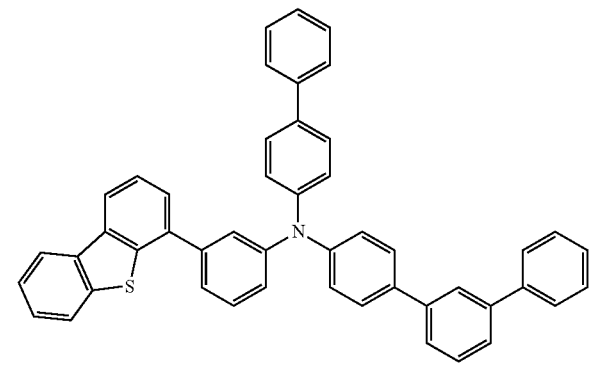
20
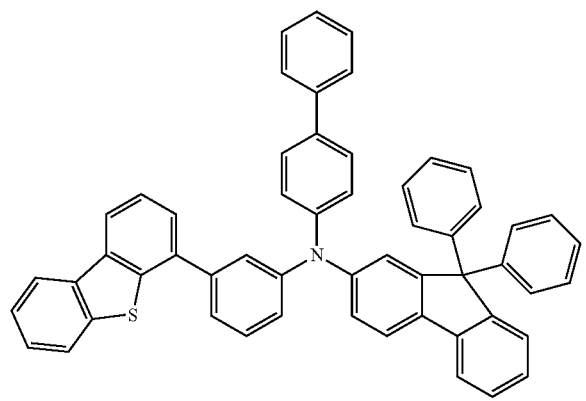
21
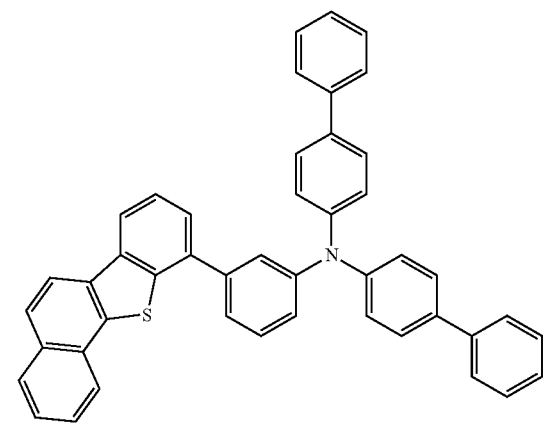
22
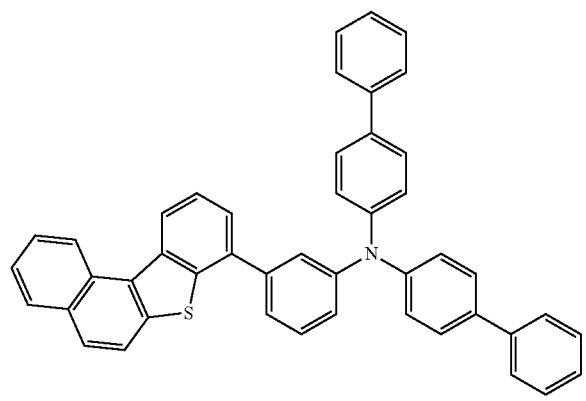
23
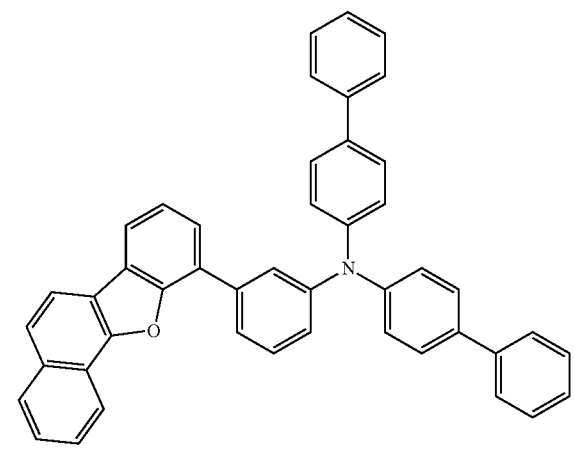

-continued
24
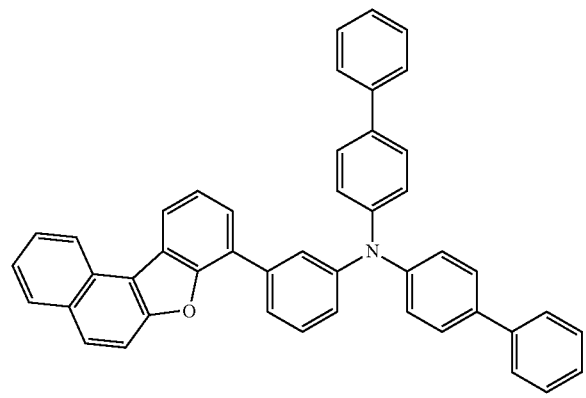
25
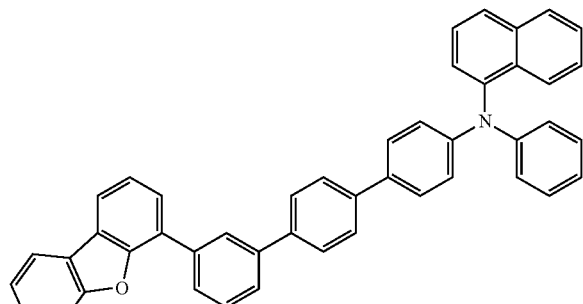
26
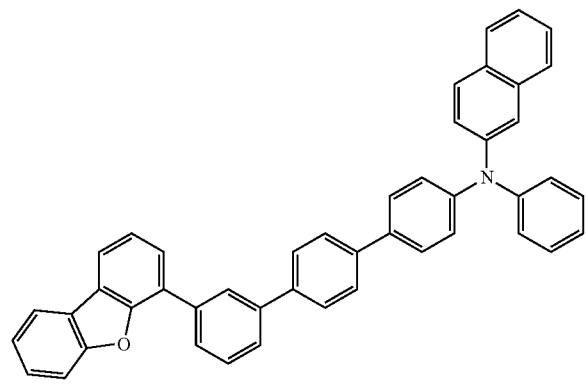
27
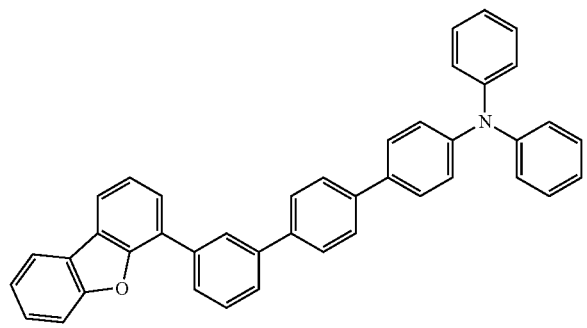
28
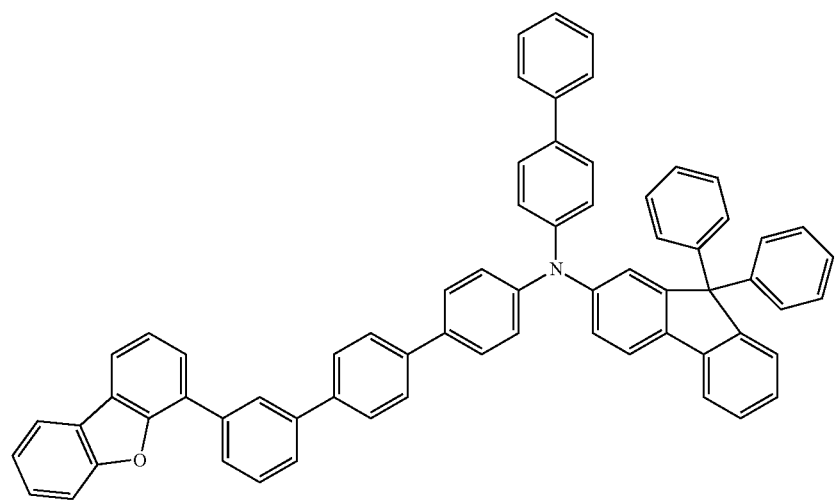

29
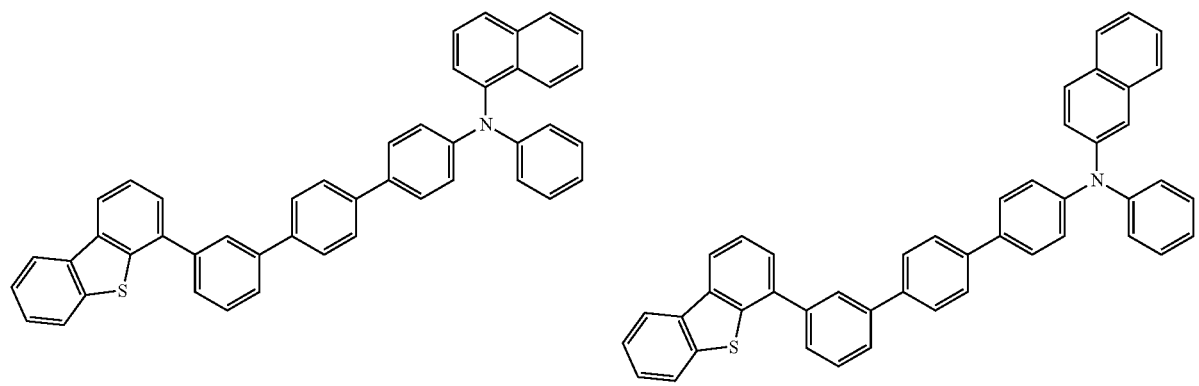
30
31
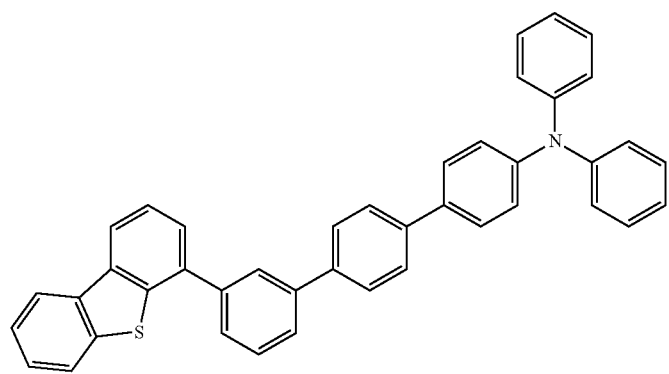
32
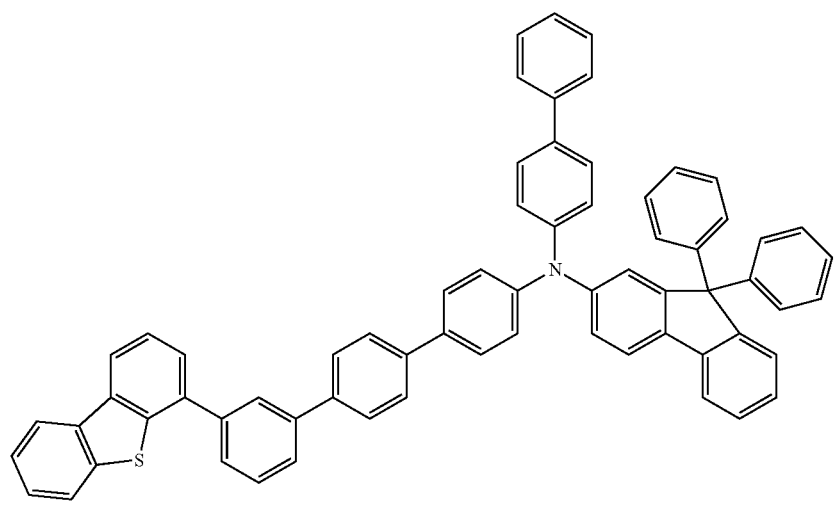

-continued
33
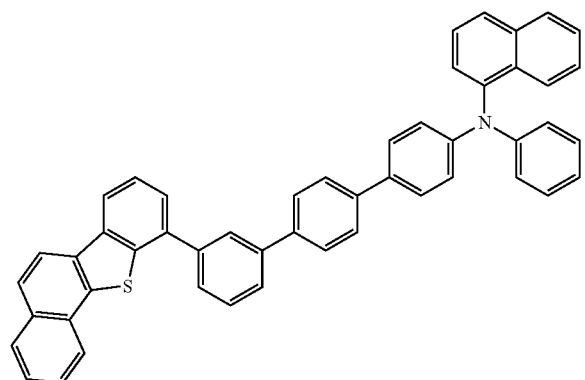
34
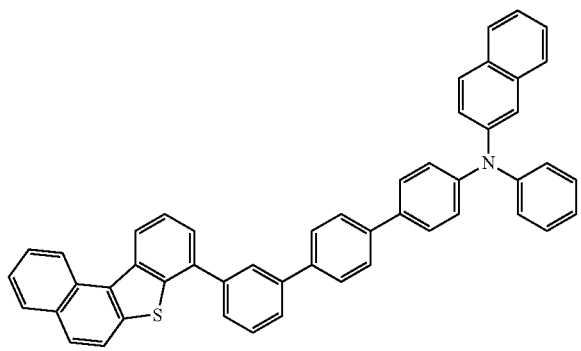
35
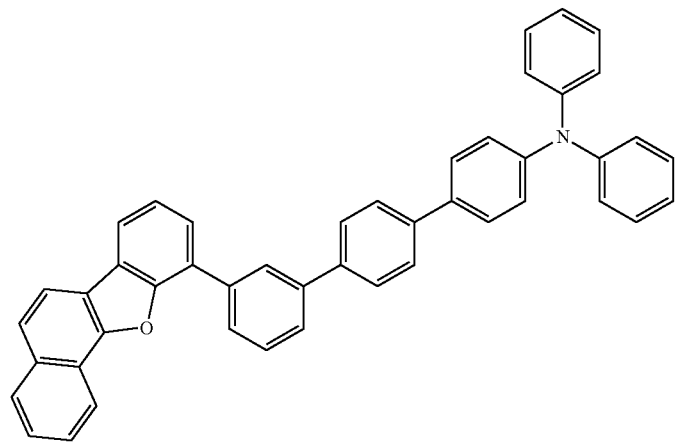
36
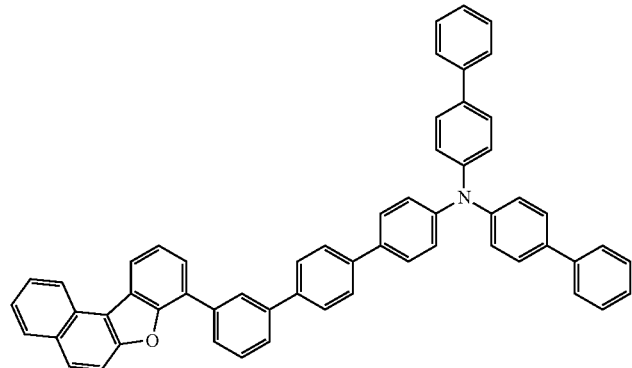
37
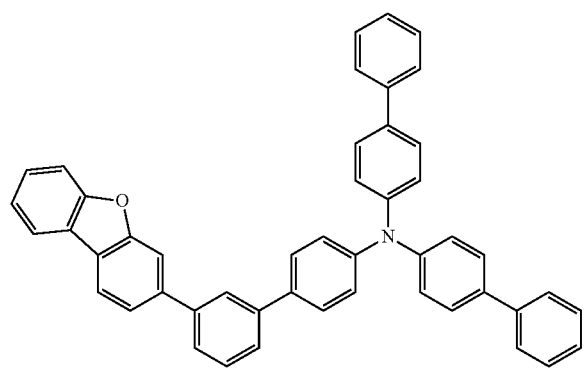
38
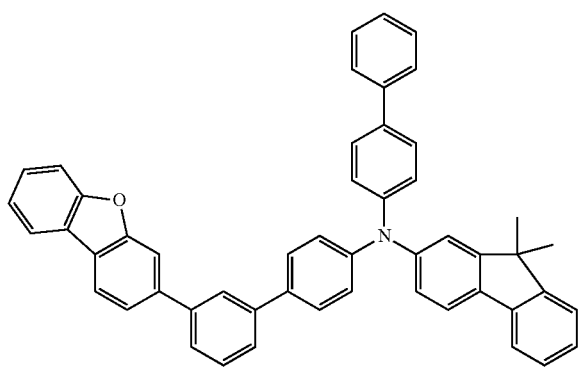

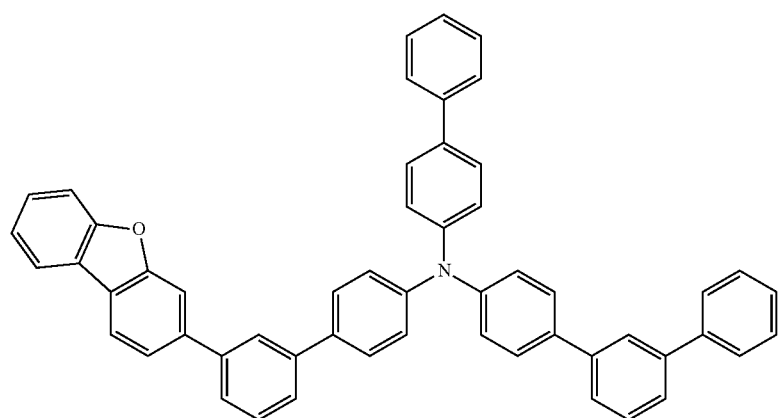
39
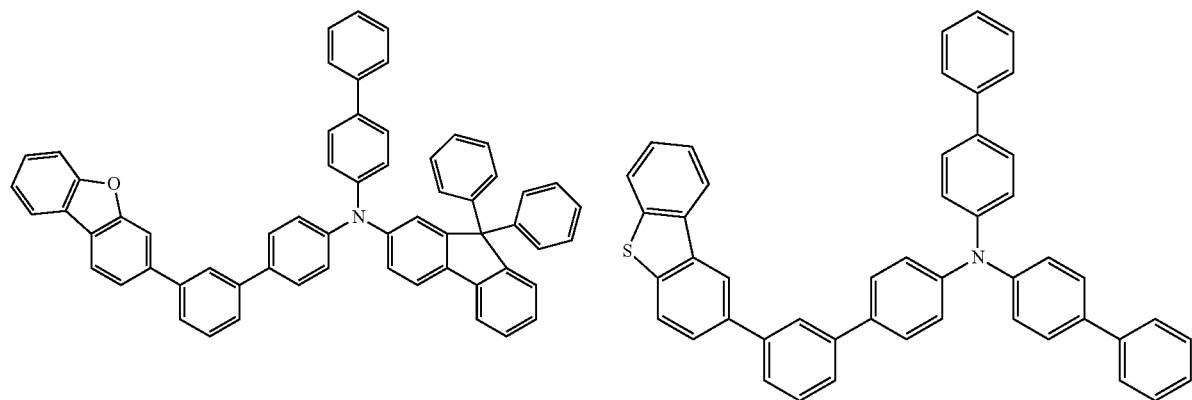
40
41
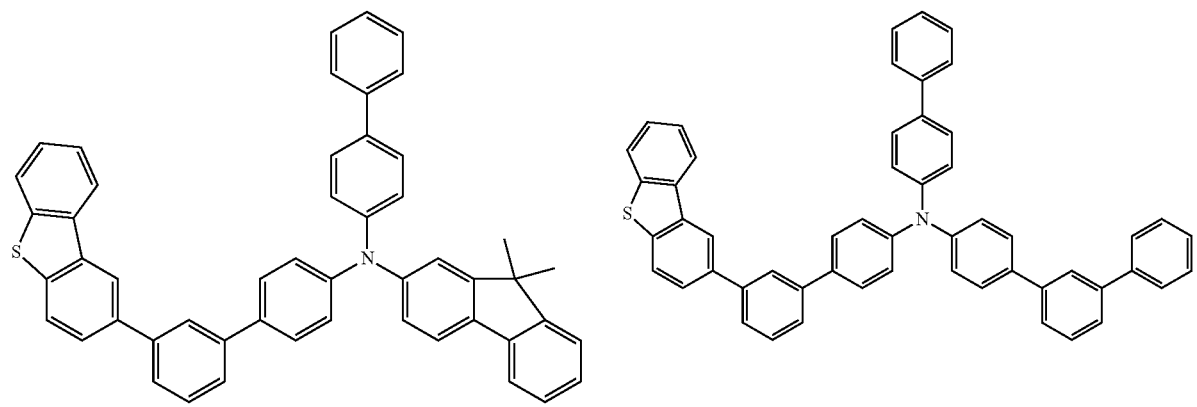
42
43

-continued

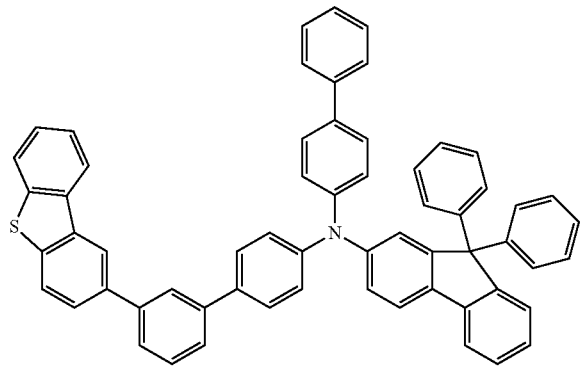

44

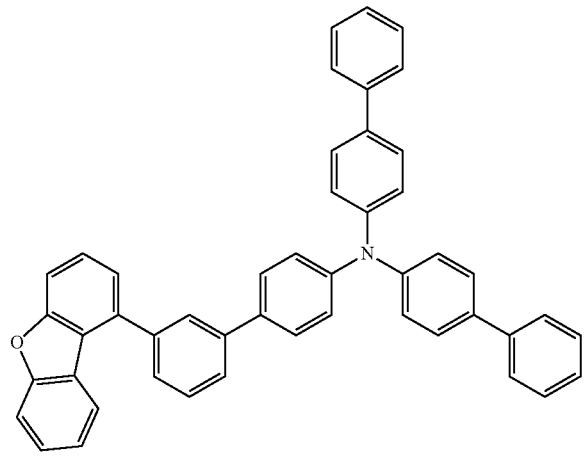

45

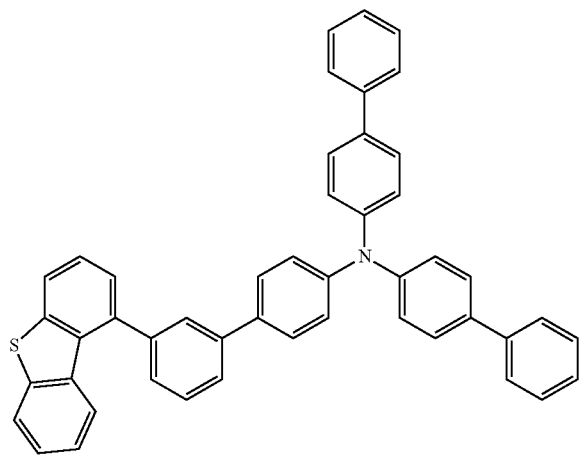

46

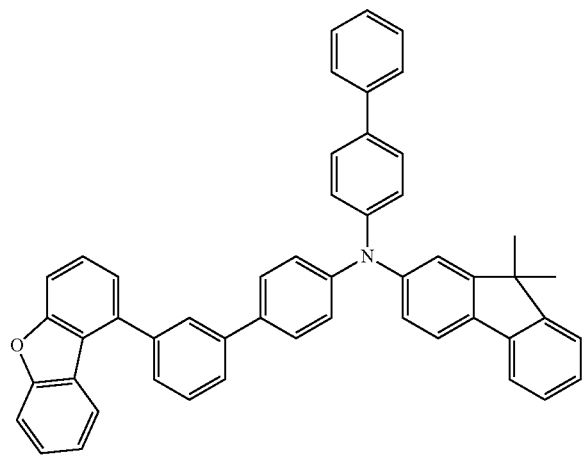

47

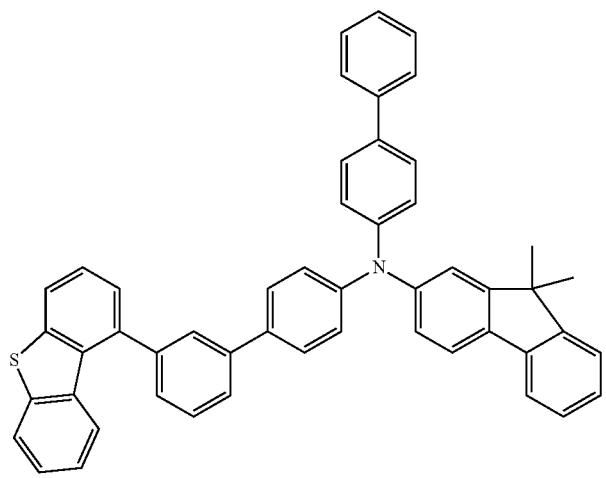

48

The emission layer-side hole transport layer 135 may include the compound represented by the above Formula 1 as the emission layer-side hole transport material and may passivate the hole transport layer 130 from electrons not consumed in the emission layer 140. In addition, since the emission layer-side hole transport layer 135 includes the compound represented by the above Formula 1, the diffusion of energy in an excited state generated in the emission layer 140 into the hole transport layer 130 may be reduced or prevented. Thus, according to this configuration, the emission layer-side hole transport layer 135 may improve the current flow durability of the hole transport layer 130.

In addition, in one embodiment, the emission layer-side hole transport layer 135 may be formed near the emission layer 140, for example, the emission layer-side hole transport layer 135 may be formed adjacent to the emission layer

140 to effectively reduce or prevent the diffusion of the electrons or the energy from the emission layer 140.

Since the emission layer-side hole transport layer 135 includes the compound represented by the above Formula 1, the charge balance of the whole organic EL device 100 may be controlled, and the diffusion of the electron accepting material doped into the anode-side hole transport layer 131 into the emission layer 140 may be restrained (e.g., reduced or prevented). Accordingly, the emission layer-side hole transport layer 135 may improve the whole charge transport property of the hole transport layer 130.

Since the emission layer-side hole transport layer 135 includes the compound represented by the above Formula 1, the charge transport property and current flow durability of the hole transport layer 130 may be improved. Thus, the emission layer-side hole transport layer 135 may improve the emission efficiency and emission life of the organic EL device 100.

As described above, the hole transport layer 130 including the anode-side hole transport layer 131, the intermediate hole transport material layer 133 and the emission layer-side hole transport layer 135 may improve the current flow durability and hole transport property of the organic EL device 100. Thus, the organic EL device 100 according to an embodiment may have improved emission efficiency and emission life.

(1-1-5. Configuration of Emission Layer)

The emission layer 140 may include a host material, a dopant material as a luminescent material, etc., and emits light via fluorescence or phosphorescence. The emission layer 140 may be formed, for example, on the hole transport layer 130 to a layer thickness within a range from about 10 nm to about 60 nm.

The host material and the dopant material included in the emission layer 140 may include any suitable host materials and dopant materials. For example, the emission layer 140 may include a fluoranthene derivative, a pyrene derivative, an arylacetylene derivative, a fluorene derivative, a perylene derivative, a chrysene derivative, etc., as the host material or the dopant material. In one embodiment, the emission layer 140 may include tris(8-quinolinolato)aluminum (Alq3), 4,4'-N,N'-dicarbazole-biphenyl (CBP), poly(n-vinylcarbazole) (PVK), 4,4',4"-tris(N-carbazolyl)triphenylamine (TCTA), 1,3,5-tris(N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dmCBP), bis(2,2-diphenyl vinyl)-1,1'-biphenyl (DPVBi), 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-(E)-2-(6-((E)-4-(diphenylamino)styryl)naphthalen-2-yl)vinyl)phenyl)-N-phenylbenzenamine (N-BDAVBi), 2,5,8,11-tetra-t-butylperylene (TBPe), 1,1-dipyrene, 1,4-dipyrenylbenzene, 1,4-bis(N,N-diphenylamino)pyrene, etc., as the host material or the dopant material.

In addition, the emission layer 140 may, in one embodiment, include a compound represented by the following Formula 3.

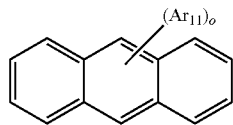

Formula 3

In the above Formula 3, $Ar_{11}$ is each independently (e.g., when o is two or greater, each of $Ar_{11}$ is independently) hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group or a hydroxyl group; and o is an integer from 1 to 10.

In addition, examples of the compound represented by Formula 3 may include the following Compounds 3-1 to 3-12. However, the compound represented by Formula 3 is not limited to the following Compounds 3-1 to 3-12.

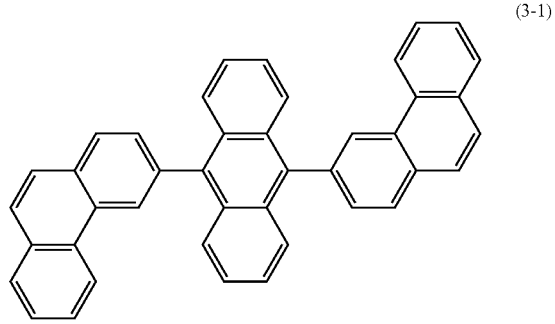

(3-1)

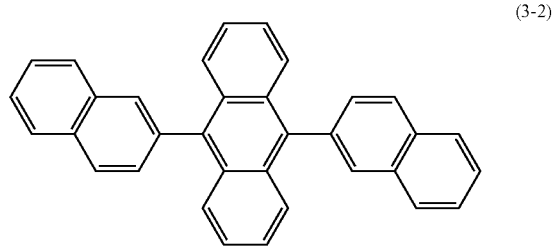

(3-2)

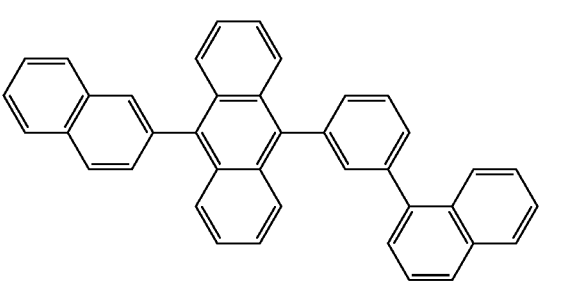

(3-3)

(3-4)
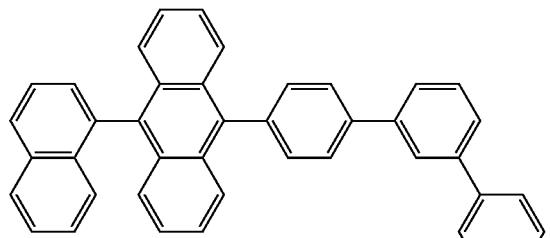

(3-9)
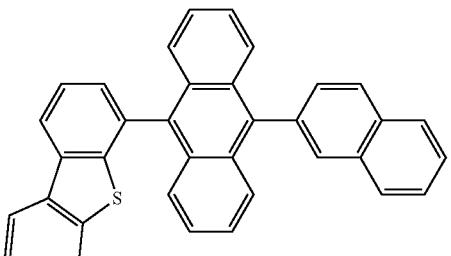

(3-5)

(3-10)

(3-6)

(3-11)

(3-7)

(3-12)
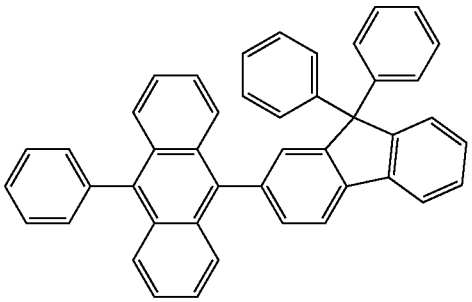
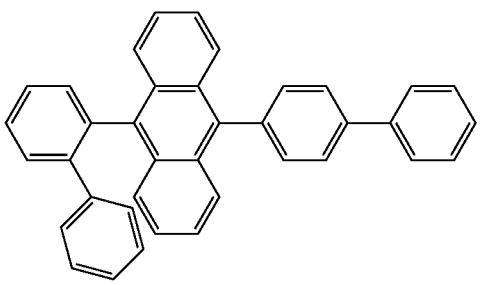
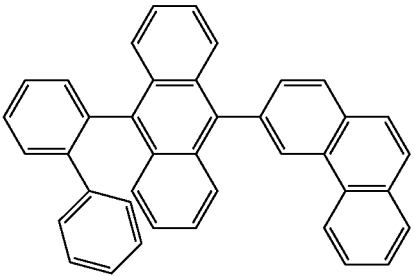
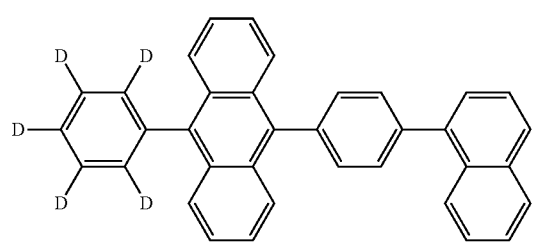

(3-8)
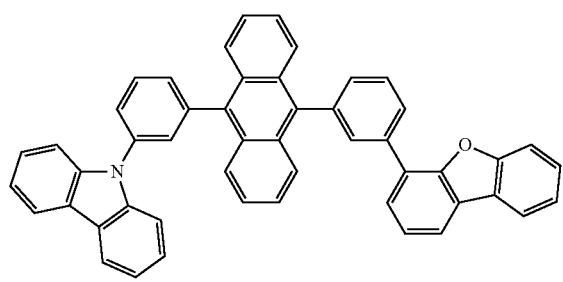

In the case that the emission layer 140 includes the compound represented by Formula 3, the anode-side hole transport layer 131 may improve the hole injection property from the first electrode 120 significantly. Thus, the emission layer 140 may further improve the emission property of the organic EL device 100 by including the compound represented by Formula 3.

The emission layer 140 may include the compound represented by Formula 3 as the host material or as the dopant material.

The emission layer 140 may be formed as an emission layer emitting light with a specific color. For example, the emission layer 140 may be formed as a red emitting layer, a green emitting layer or a blue emitting layer.

In the case that the emission layer 140 is the blue emitting layer, suitable blue dopants may be utilized. For example, perylene and the derivative thereof, and/or an iridium (Ir)

complex (such as bis[2-(4,6-difluorophenyl)pyridinate]picolinate iridium(III) (FIrpic)) may be utilized as the blue dopant.

In the case that the emission layer 140 is the red emitting layer, suitable red dopants may be utilized. For example, rubrene and the derivative thereof, 4-dicyanomethylene-2-(p-dimethylaminostyryl)-6-methyl-4H-pyrane (DCM) and the derivative thereof, an iridium complex (such as bis(1-1-phenylisoquinoline)(acetylacetonate) iridium(III) (Ir(piq)$_2$(acac)), an osmium (Os) complex, a platinum complex, etc., may be utilized as the red dopant.

In the case that the emission layer 140 is the green emitting layer, suitable green dopants may be utilized. For example, coumarin and the derivative thereof, an iridium complex (such as tris(2-phenylpyridine) iridium(III) (Ir (ppy)$_3$)), etc., may be utilized.

(1-1-6. Configuration of Electron Transport Layer)

The electron transport layer 150 is a layer including an electron transport material and having electron transporting function. The electron transport layer 150 may be formed, for example, on the emission layer 140 to a layer thickness within a range from about 15 nm to about 50 nm. The electron transport material included in the electron transport layer 150 may be any suitable electron transport materials.

Examples of the suitable electron transport material may include, tris(8-hydroxyquinolinato)aluminum (Alq3) or an electron transport material having a nitrogen-containing aromatic ring. Examples of the electron transport material having a nitrogen-containing aromatic ring may include an electron transport material including a pyridine ring (such as 1,3,5-tri[(3-pyridyl)-phen-3-yl]benzene), an electron transport material including a triazine ring (such as 2,4,6-tris(3'-(pyridin-3-yl)biphenyl-2-yl)-1,3,5-triazine), an electron transport material including an imidazole derivative (such as 2-(4-(N-phenylbenzoimidazolyl-1-ylphenyl)-9,10-dinaphthylanthracene)), etc.

(1-1-7. Configuration of Electron Injection Layer)

The electron injection layer 160 is a layer having function of easy injection of electrons from the second electrode 170. The electron injection layer 160 may be formed, for example, on the electron transport layer 150 to a layer thickness within a range from about 0.3 nm to about 9 nm. The electron injection layer 160 may be formed utilizing any suitable materials that may be utilized as materials for forming the electron injection layer 160. Examples of the material for forming the electron injection layer 160 may include a Li complex (such as lithium 8-quinolinato (Liq) or lithium fluoride (LiF)), sodium chloride (NaCl), cesium fluoride (CsF), lithium oxide (Li$_2$O), barium oxide (BaO), etc.

(1-1-8. Configuration of Second Electrode)

The second electrode 170 may be, for example, a cathode and formed on the electron injection layer 160 utilizing an evaporation method or a sputtering method. For example, the second electrode 170 may be formed as a reflection electrode utilizing a metal, an alloy, a conductive compound, etc., having low work function. The second electrode 170 may be formed utilizing, a metal (such as lithium (Li), magnesium (Mg), aluminum (Al) or calcium (Ca)), or a metal mixture (such as aluminum-lithium (Al—Li), magnesium-indium (Mg—In) or magnesium-silver (Mg—Ag)). In addition, the second electrode 170 may be formed as a thin film of a metal material, having a thickness of about 20 nm or less (e.g., not greater than 20 nm) and may be formed as a transmission electrode utilizing ITO, IZO, etc.

(1-1-9. Modification Example of Organic EL Device)

In addition, the structure of the organic EL device 100 shown in the drawing is only an illustration, and the organic EL device 100 according to an embodiment is not limited to the structure of the drawing. In the organic EL device 100 according to an embodiment, some layers may be formed as a multi-layer, or another layer may be additionally formed. In the organic EL device 100 according to an embodiment, at least one of the electron transport layer 150 and the electron injection layer 160 may not be provided.

In the organic EL device 100 according to an embodiment, a hole injection layer may be provided between the first electrode 120 and the hole transport layer 130.

The hole injection layer is a layer having the function of easy injection of holes from the first electrode 120. The hole injection layer may be formed, for example, on the first electrode 120 to a layer thickness within a range from about 10 nm to about 150 nm. The hole injection layer may be formed utilizing any suitable materials for forming the hole injection layer. Examples of the material for forming the hole injection layer may include a triphenylamine-containing polyether ketone (TPAPEK), 4-isopropyl-4'-methyldiphenyliodonium tetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound (such as copper phthalocyanine), 4,4',4"-tris(3-methylphenylphenylamino)triphenylamine (m-MTDATA), N,N'-di(1-naphthyl)-N,N'-diphenylbenzidine (NPB), 4,4', 4"-tris{N,N-diamino}triphenylamine (TDATA), 4,4',4"-tris(N,N-2-naphthylphenylamino)triphenylamine (2-TNATA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA) or polyaniline/poly(4-styrenesulfonate) (PANI/PSS), etc.

(1-1-10. Method of Manufacturing Organic EL Device)

Each layer of the organic EL device 100 according to an embodiment as described above may be formed by selecting an appropriate layer forming method depending on materials utilized, such as vacuum evaporation, sputtering, or various other suitable coating methods.

For example, a metal layer such as the first electrode 120, the second electrode 170, or the electron injection layer 160 may be formed utilizing an evaporation method (including an electron beam evaporation method, a hot filament evaporation method and/or a vacuum evaporation method), a sputtering method, and/or a plating method (including an electroplating method and/or an electroless plating method).

An organic layer (such as the hole transport layer 130, the emission layer 140 or the electron transport layer 150) may be formed utilizing a physical vapor deposition (PVD) method (such as a vacuum deposition method), a printing method (such as a screen printing method or an ink jet printing method), a laser transcription method and/or a coating method (such as a spin coating method).

Hereinabove, an embodiment of the organic EL device 100 according to an embodiment has been explained in more detail.

EXAMPLES 1-2. Examples

Hereinafter, organic EL devices according to example embodiments will be explained in more detail referring to examples and comparative examples. The following embodiments are only for illustration, and the organic EL devices according to example embodiments are not limited thereto.

(1-2-1. Synthesis of Compound Represented by Formula 1)

First, a synthetic method of a compound represented by Formula 1 will be explained in more detail referring to synthetic methods of Compounds 1 and 5. The following embodiments are only for illustration, and the synthetic methods of the compound represented by Formula 1 are not limited thereto.

(1-2-1-1. Synthesis of Compound 1)

According to the following Reaction 1, Compound 1, which is the compound represented by Formula 1, was synthesized. The product thus obtained was identified by measuring physical properties by means of $^1$HNMR and FAB-MS.

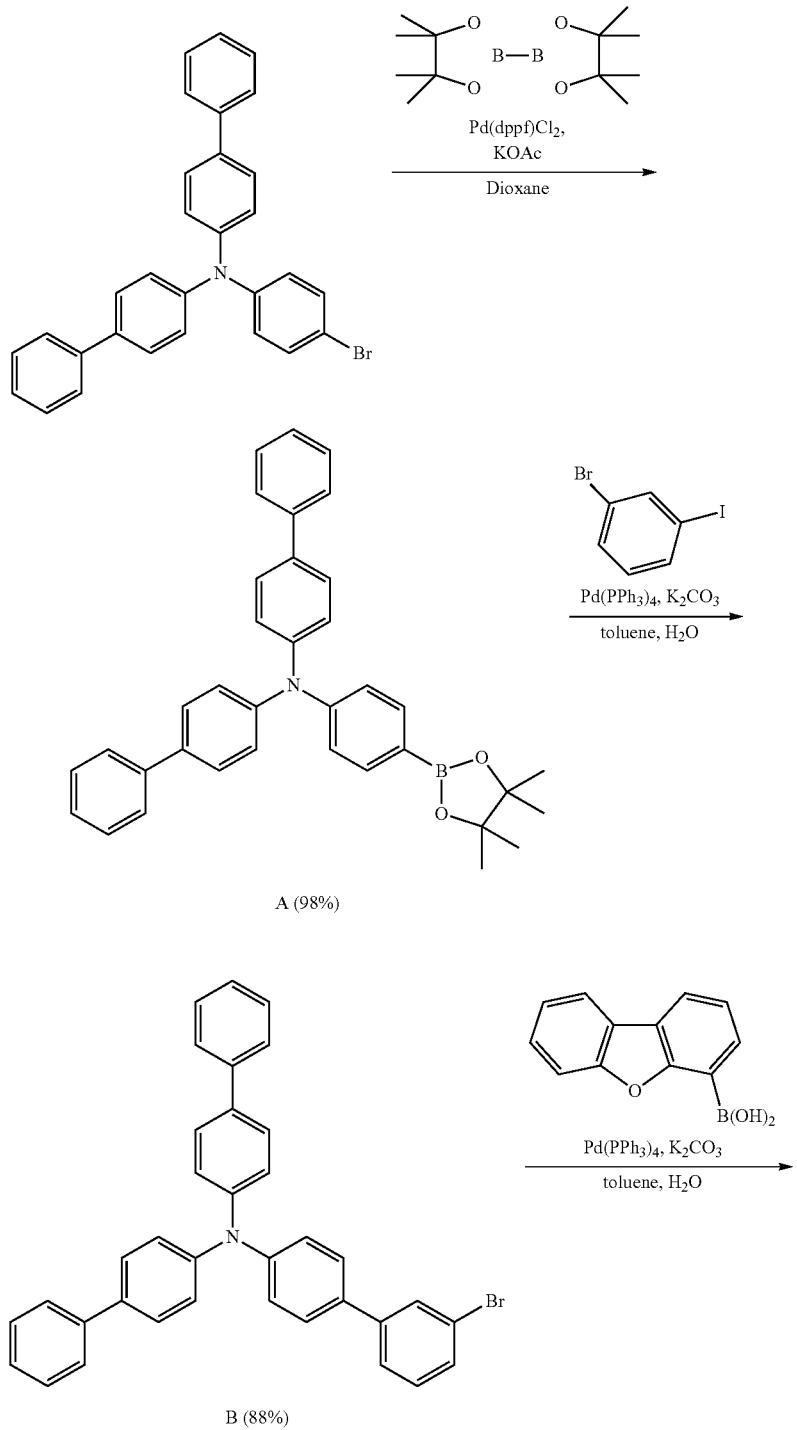

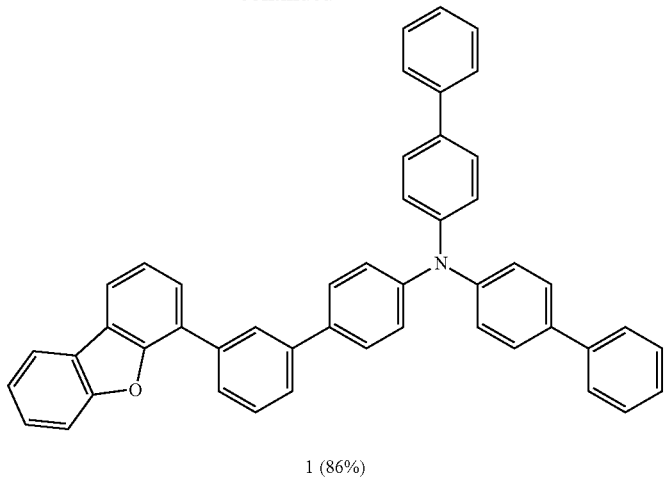

1 (86%)

(Synthesis of Compound A)

Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$·CH$_2$Cl$_2$, 33.3 g of KOAc and 33.0 g of bis(pinacolato)diboron were added to a 2 L flask, followed by degassing under vacuum and stirring in a dioxane solvent at about 100° C. for about 12 hours. Then, solvents were distilled from the reactant, CH$_2$Cl$_2$ and water were added thereto, and an organic phase was separated. To the separated organic phase, magnesium sulfate (Mg$_2$SO$_4$) and activated clay were added, filtering with suction was performed, and the solvent was distilled. The crude product thus obtained was separated by silica gel column chromatography utilizing a mixture solvent of dichloromethane and hexane, to produce 56.8 g (Yield 98%) of Compound A as a white solid (FAB-MS: C$_{36}$H$_{34}$BNO$_2$, measured value 523).

(Synthesis of Compound B)

Under an Ar atmosphere, 10.0 g of Compound A, 6.00 g of 1-iodo-3-bromobenzene, 1.54 g of Pd(PPh$_3$)$_4$, and 5.25 g of potassium carbonate (K$_2$CO$_3$) were added to a 300 mL, three necked flask, followed by heating and stirring in a mixture solvent of 450 mL of toluene and 60 mL of water at about 90° C. for about 8 hours. After air cooling, water was added to the reactant, an organic phase was separated, and solvents were distilled from the separated organic phase. The crude product thus obtained was separated by silica gel column chromatography utilizing a mixture solvent of dichloromethane and hexane and recrystallized utilizing a mixture solvent of toluene and hexane to produce 9.29 g (Yield 88%) of Compound B as a white solid (FAB-MS: C$_{36}$H$_{26}$BrN, measured value 551).

(Synthesis of Compound 1)

Under an Ar atmosphere, 3.10 g of Compound B, 1.2 g of dibenzofuran-4-boronic acid, 0.84 g of Pd(PPh$_3$)$_4$, and 2.35 g of potassium carbonate (K$_2$CO$_3$) were added to a 500 mL, three necked flask, followed by heating and stirring in a mixture solvent of 170 mL of toluene and 80 mL of water at about 90° C. for about 8 hours. After air cooling, water was added to the reactant, an organic phase was separated, and solvents were distilled from the separated organic phase. The crude product thus obtained was separated by silica gel column chromatography utilizing a mixture solvent of dichloromethane and hexane and recrystallized utilizing a mixture solvent of toluene and hexane to produce 3.08 g (Yield 86%) of Compound 1 as a white solid. Chemical shift values (δ) of Compound 1 by $^1$HNMR (300 MHz, CDCl$_3$) were 8.11 (s, 1H), 8.00 (d, J=7.6 Hz, 1H), 7.96 (d, J=7.6 Hz, 1H), 7.87 (d, J=7.4 Hz, 1H), 7.67-7.23 (m, 29H), and the measured molecular weight of Compound 1 by FAB-MS was 639 (C$_{48}$H$_{33}$NO).

(1-2-1-2. Synthesis of Compound 5)

According to the following Reaction 2, Compound 5 as the compound represented by Formula 1 was synthesized. The product was identified by measuring the physical properties by $^1$HNMR and FAB-MS.

Reaction 2

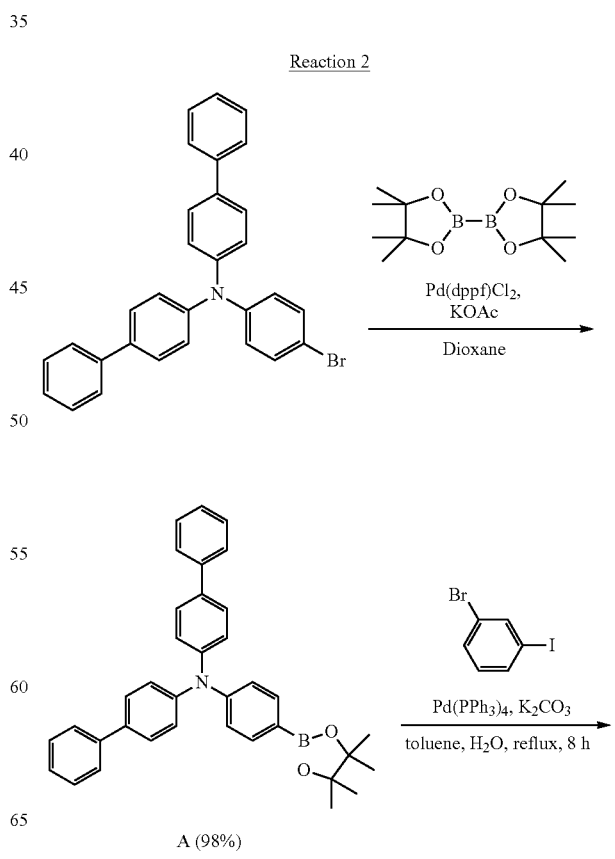

A (98%)

-continued

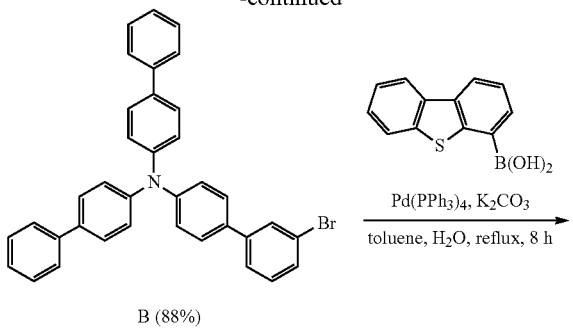

B (88%)

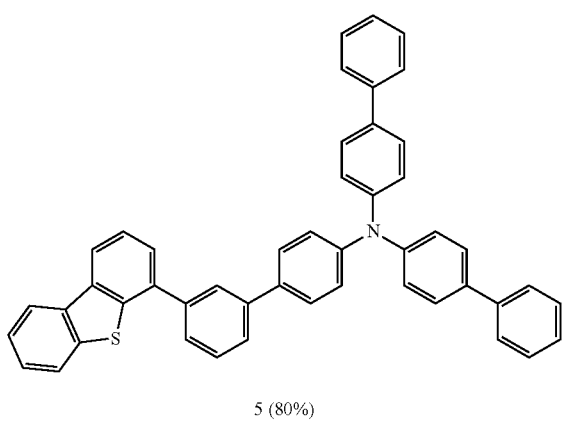

5 (80%)

(Synthesis of Compounds A and B)

Since the synthetic method of Compounds A and B are the same as described above (1-2-1-1. Synthesis of Compound 1), explanation thereabout will not be provided again.

(Synthesis of Compound 5)

Under an Ar atmosphere, 3.10 g of Compound B, 1.28 g of dibenzothiophene-4-boronic acid, 0.84 g of Pd(PPh$_3$)$_4$, and 2.35 g of potassium carbonate (K$_2$CO$_3$) were added to a 500 mL, three necked flask, followed by heating and stirring in a mixture solvent of 170 mL of toluene and 80 mL of water at about 90° C. for about 8 hours. After air cooling, water was added to the reactant, an organic phase was separated, and solvents were distilled from the separated organic phase. The crude product thus obtained was separated by silica gel column chromatography utilizing a mixture solvent of dichloromethane and hexane and recrystallized utilizing a mixture solvent of toluene and hexane to produce 2.94 g (Yield 80%) of Compound 5 as a white solid. Chemical shift values (δ) of Compound 5 by $^1$HNMR (300 MHz, CDCl$_3$) were 8.46-8.41 (m, 2H), 8.20 (d, 1H, J=7.80 Hz), 7.98 (d, 1H, J=7.90 Hz), 7.58-7.50 (m, 18H), 7.48-7.41 (m, 4H), 6.69-6.65 (m, 4H), and the measured molecular weight of Compound 5 by FAB-MS was 656 (C$_{48}$H$_{33}$NS).

(1-2-2. Manufacture of Organic EL Device Including Anode-Side Hole Transport Material and Anode-Side Hole Transport Layer Doped with Electron Accepting Material)

An organic EL device according to an embodiment was manufactured by the following manufacturing method.

First, with respect to an ITO-glass substrate patterned and washed in advance, surface treatment utilizing UV-Ozone (O$_3$) was conducted. The layer thickness of an ITO layer (first electrode) on a glass substrate was about 150 nm. After ozone treatment, the surface treated substrate was inserted in a glass bell jar evaporator for forming an organic layer, and an anode-side hole transport layer, an intermediate hole transport material layer, an emission layer-side hole transport layer, an emission layer and an electron transport layer were evaporated one by one with a vacuum degree of about $10^{-4}$ to about $10^{-5}$ Pa. The layer thickness of each of the anode-side hole transport layer, the intermediate hole transport material layer and the emission layer-side hole transport layer was about 10 nm. The layer thickness of the emission layer was about 25 nm, and the layer thickness of the electron transport layer was about 25 nm. Then, the substrate was moved into a glass bell jar evaporator for forming a metal layer, and an electron injection layer and a second electrode were evaporated with a vacuum degree of about $10^{-4}$ to about $10^{-5}$ Pa. The layer thickness of the electron injection layer was about 1 nm and the layer thickness of the second electrode was about 100 nm.

Here, the anode-side hole transport layer, the intermediate hole transport material layer and the emission layer-side hole transport layer correspond to the hole transport layer with a stacked structure. The anode-side hole transport layer, the intermediate hole transport material layer and the emission layer-side hole transport layer were manufactured in examples and comparative examples utilizing the materials shown in the following Table 1.

In Table 1, for example, the expression of "Compound 2-3, Compound 4-15" indicates that Compound 2-3 is the anode-side hole transport material, and Compound 4-15 is the doped electron accepting material. The amount doped of the electron accepting material was about 3 wt % on the basis of the amount of the anode-side hole transport material.

In addition, Compounds 6-1, 6-2 and 6-3 refers to common hole transport materials represented by the following formula 12.

Formula 12

(6-1)

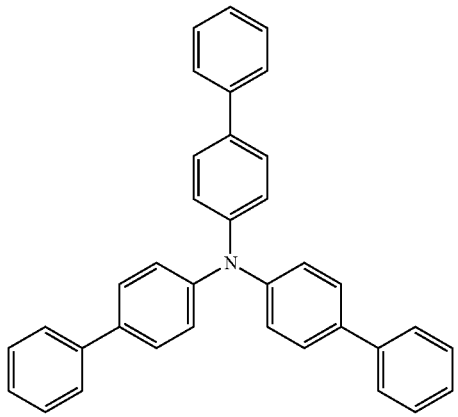

-continued (6-2)

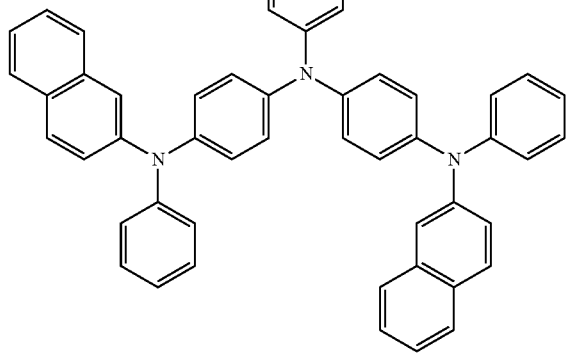

(6-3)

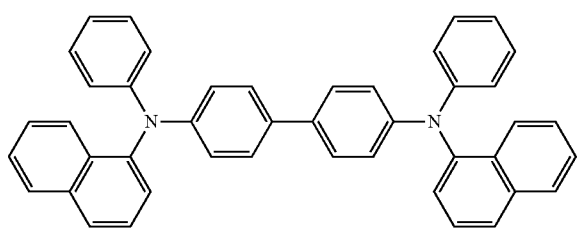

9,10-di(1-2-naphthyl)anthracene (ADN, Compound 3-2) was utilized as the host material of the emission layer, and 2,5,8,11-tetra-t-butylperylene (TBP) was utilized as the dopant material. 3 wt % of the dopant material on the basis of the amount of the host material was added. In addition, the electron transport layer was formed utilizing Alq3, the electron injection layer was formed utilizing LiF, and the second electrode was formed utilizing aluminum (Al).

(1-2-2. Evaluation Results)

Then, the driving voltage and the half life of the organic EL device thus manufactured were evaluated. Evaluation results are shown together in the following Table 1. The driving voltage and the emission efficiency in each example and comparative example were obtained by measuring at current density of about 10 mA/cm². The emission life was obtained by measuring a time period for decreasing luminance to half with the initial luminance of about 1,000 cd/m².

In addition, the measurement was conducted utilizing a source meter of 2400 series of Keithley Instruments Co., a Color brightness photometer CS-200 (Konica Minolta holdings Co., Ltd., measurement angle of 1°), and a PC program LabVIEW8.2 (National instruments Co., Ltd. in Japan) in a dark room.

TABLE 1

|  | Anode-side hole transport material | Intermediate hole transport material | Emission layer-side hole transport layer | Driving current [V] | Emission efficiency [cd/A] | Emission life LT50 [h] |
| --- | --- | --- | --- | --- | --- | --- |
| Example 1-1 | Compound 2-3, Compound 4-15 | Compound 2-3 | Compound 1 | 6.1 | 7.6 | 4,000 |
| Example 1-2 | Compound 2-3, Compound 4-15 | Compound 2-3 | Compound 5 | 6.1 | 7.5 | 4,100 |
| Example 1-3 | Compound 2-3, Compound 4-16 | Compound 2-3 | Compound 1 | 6.2 | 7.4 | 3,900 |
| Example 1-4 | Compound 2-3, Compound 4-15 | Compound 2-17 | Compound 1 | 6.1 | 7.6 | 3,200 |
| Example 1-5 | Compound 6-2, Compound 4-15 | Compound 2-3 | Compound 1 | 6.5 | 7.5 | 3,200 |
| Example 1-6 | Compound 2-3, Compound 4-15 | Compound 6-3 | Compound 1 | 6.4 | 7.6 | 2,600 |
| Comparative Example 1-1 | Compound 2-3, Compound 4-15 | Compound 1 | Compound 2-3 | 6.4 | 7.2 | 2,100 |
| Comparative Example 1-2 | Compound 2-3 | Compound2-3 | Compound 1 | 7.5 | 6.7 | 2,200 |

TABLE 1-continued

|  | Anode-side hole transport material | Intermediate hole transport material | Emission layer-side hole transport layer | Driving current [V] | Emission efficiency [cd/A] | Emission life LT50 [h] |
|---|---|---|---|---|---|---|
| Comparative Example 1-3 | Compound 2-3, Compound 4-15 | Compound 2-3 | Compound 6-1 | 6.4 | 7.3 | 2,300 |

Referring to Table 1, the emission efficiency was improved, and the half life was increased for Examples 1-1 to 1-6 when compared to those for Comparative Examples 1-1 to 1-3. Thus, the improvement of the emission life of the organic EL device could be realized by providing the anode-side hole transport layer, the intermediate hole transport material layer and the emission layer-side hole transport layer between the first electrode and the emission layer.

For example, if comparing Examples 1-1 to 1-6 with Comparative Example 1-2, the properties for Examples 1-1 to 1-6 were better. In Comparative Example 1-2, the electron accepting material (Compound 4-15 or 4-16) was not doped in the anode-side hole transport layer. Thus, it was found to be desirable that the electron accepting material was doped in the anode-side hole transport layer.

If comparing Example 1-1 with Comparative Example 1-1, the properties for Example 1-1 were better. In Comparative Example 1-1, compounds included in the intermediate hole transport material layer and the emission layer-side hole transport layer were changed from those in Example 1-1. Thus, it was found to be desirable that the emission layer-side hole transport layer including the compound represented by Formula 1 was adjacent to the emission layer.

If comparing Example 1-1 with Comparative Example 1-3, the properties for Examples 1-1 to 1-6 were better. In Comparative Example 1-3, the emission layer-side hole transport material included in the emission layer-side hole transport layer was not Compound 1 or 5 represented by Formula 1, but a common hole transport material, i.e., Compound 6-1. Thus, it was found to be desirable that the emission layer-side hole transport layer included the compound represented by Formula 1.

If comparing Examples 1-1 to 1-5 with Example 1-6, the properties for Examples 1-1 to 1-5 were better. In Example 1-6, the intermediate hole transport material included in the intermediate hole transport material layer was not Compound 2-3 or 2-17 represented by Formula 2 but a common hole transport material, i.e., Compound 6-3. Thus, it was found to be desirable that the intermediate hole transport material layer included the compound represented by Formula 2.

If comparing Examples 1-1 to 1-4 with Example 1-5, the properties of Examples 1-1 to 1-4 were better. In Example 1-5, the anode-side hole transport material included in the anode-side hole transport layer was not Compound 2-3 represented by Formula 2 but a common hole transport material, i.e., Compound 6-2. Thus, it was found to be desirable that the anode-side hole transport layer included the compound represented by Formula 2.

As described above, since the anode-side hole transport layer doped with the electron accepting material, the intermediate hole transport material layer, and the emission layer-side hole transport layer including the compound represented by Formula 1 were stacked between the first electrode (anode) and the emission layer, the emission efficiency and emission life of the organic EL device were improved.

The results show that the hole transport layer may be passivated from electrons not consumed in the emission layer-side hole transport layer, the diffusion of energy in an excited state generated from the emission layer into the hole transport layer may be reduced or prevented, and the charge balance of a whole device may be controlled by disposing the emission layer-side hole transport layer including the compound represented by Formula 1. The results also show that the emission layer-side hole transport layer may restrain (e.g., reduce or prevent) the diffusion of the electron accepting material included in the anode-side hole transport layer provided near the first electrode (anode) into the emission layer by disposing the emission layer-side hole transport layer including the compound represented by Formula 1.

<2-1. Configuration of Organic EL Device Including Anode-Side Hole Transport Layer Mainly Including Electron Accepting Material>

Hereinafter, an organic EL device including an anode-side hole transport layer mainly including an electron accepting material will be explained referring to the drawing.

The organic EL device including the anode-side hole transport layer mainly including the electron accepting material includes the above-mentioned anode-side hole transport material and has substantially the same configuration, i.e., substantially the same configuration of a substrate, substantially the same configuration of a first electrode, substantially the same configuration of an emission layer, substantially the same configuration of an electron transport layer, substantially the same configuration of an electron injection layer, substantially the same configuration of a second electrode and substantially the same method of manufacturing an organic EL device as those of the organic EL device including the anode-side hole transport layer doped with the electron accepting material, and has a different configuration of the hole transport layer. Thus, the configuration of the hole transport layer will be explained in more detail, hereinafter.

(2-1-1. Configuration of Hole Transport Layer)

The hole transport layer 130 may include a hole transport material and have hole transporting function. The hole transport layer 130 may be formed, for example, on the first electrode 120 to a layer thickness (total layer thickness of a multi-layer structure) within a range from about 10 nm to about 150 nm.

Here, the hole transport layer 130 of the organic EL device 100 according to an embodiment may be formed as a multi-layer by stacking from a first electrode 120, an anode-side hole transport layer 131, an intermediate hole transport material layer 133 and an emission layer-side hole transport layer 135 one by one. In addition, the ratio of the thicknesses of the layers is not specifically limited.

(2-1-1-1. Configuration of Anode-Side Hole Transport Layer)

The anode-side hole transport layer 131 may be a layer mainly including an electron accepting material. For example, the anode-side hole transport layer 131 may be formed on the first electrode 120.

The anode-side hole transport layer 131 is a layer formed mainly utilizing the electron accepting material, however, a material other than the electron accepting material may be included. In addition, the expression that "the anode-side hole transport layer 131 may be formed mainly utilizing the electron accepting material" refers to that the anode-side hole transport layer 131 includes about 50 wt % or greater of the electron accepting material on the basis of the total amount of the anode-side hole transport layer 131.

The anode-side hole transport layer 131 may be formed mainly utilizing the electron accepting material and may improve hole injection property from the first electrode 120. Thus, in one embodiment, the anode-side hole transport layer 131 may be provided near the first electrode 120, and for example, the anode-side hole transport layer 131 may be provided adjacent to the first electrode 120.

The electron accepting material included in the anode-side hole transport layer 131 may be any suitable electron accepting materials. However, in one embodiment, the electron accepting material included in the anode-side hole transport layer 131 may have a LUMO level within a range from about −9.0 eV to about −4.0 eV, and for example, the electron accepting material included in the anode-side hole transport layer 131 may have the LUMO level within a range from about −6.0 eV to about −4.0 eV.

Here, examples of the electron accepting material having the LUMO level within a range from about −9.0 eV to about −4.0 eV may include the compounds represented by the following Formulae 4-1 to 4-14.

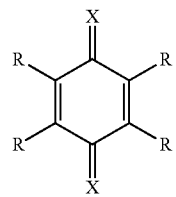
(4-1)

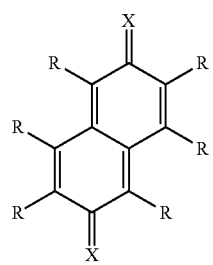
(4-2)

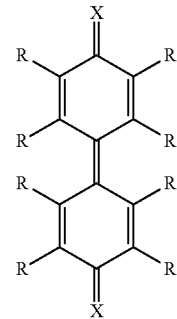
(4-3)

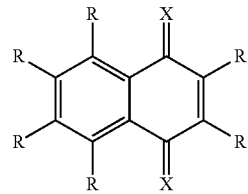
(4-4)

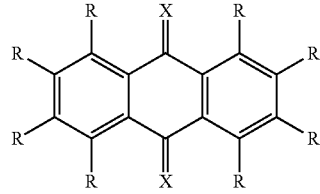
(4-5)

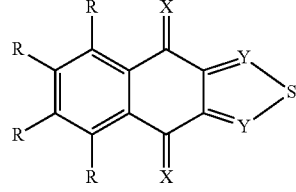
(4-6)

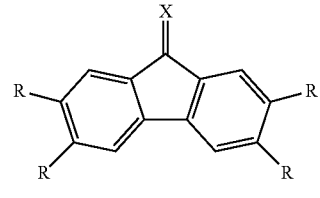
(4-7)

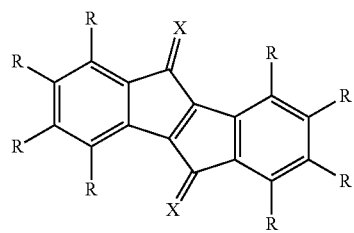
(4-8)

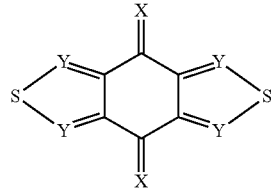
(4-9)

-continued (4-10)
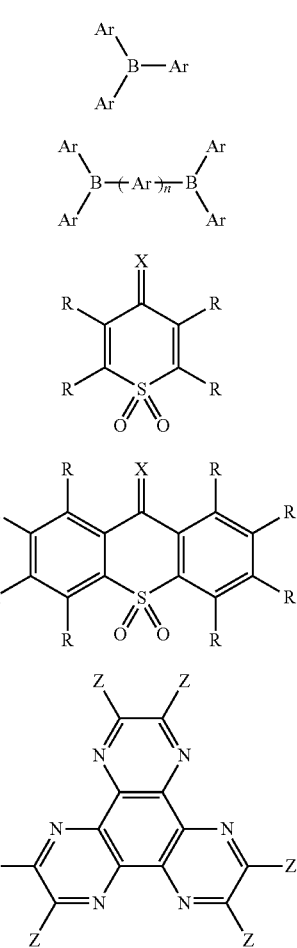

(4-11)

(4-12)

(4-13)

(4-14)

In the above Formulae 4-1 to 4-14, R is hydrogen, deuterium, a halogen atom, a fluoroalkyl group having 1 to 50 carbon atoms, a cyano group, an alkoxy group having 1 to 50 carbon atoms, an alkyl group having 1 to 50 carbon atoms, an aryl group having 6 to 50 carbon atoms or a heteroaryl group having 5 to 50 carbon atoms for forming a ring. Ar is a substituted aryl group with an electron withdrawing group or an unsubstituted aryl group having 6 to 50 carbon atoms for forming a ring, or a substituted or unsubstituted heteroaryl group having 5 to 50 carbon atoms for forming a ring; Y is a methine group (—CH═) or a nitrogen atom (—N═); Z is a pseudohalogen atom or a sulfur (S) atom; n is an integer of 10 and less; and X is one of the substituents represented by the following formulae X1 to X7.

X1

X2

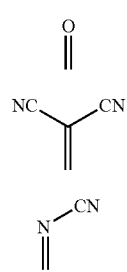

X3

X4

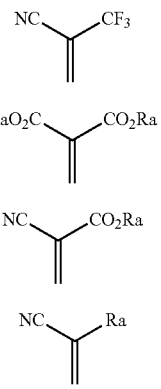

X5

X6

X7

In the above Formulae X1 to X7, Ra is hydrogen, deuterium, a halogen atom, a fluoroalkyl group having 1 to 50 carbon atoms, a cyano group, an alkoxy group having 1 to 50 carbon atoms, an alkyl group having 1 to 50 carbon atoms, a substituted or unsubstituted aryl group having 6 to 50 carbon atoms for forming a ring or a substituted or unsubstituted heteroaryl group having 5 to 50 carbon atoms for forming a ring.

Examples of the substituted or unsubstituted aryl group having 6 to 50 carbon atoms for forming a ring represented by R, Ar and Ra may include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, a fluorenyl group, etc.

Examples of the substituted or unsubstituted heteroaryl group having 5 to 50 carbon atoms for forming a ring represented by R, Ar and Ra may include a 1-pyrrolyl group, a 2-pyrrolyl group, a 3-pyrrolyl group, a pyridinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxazinyl group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, etc.

Examples of the substituted or unsubstituted fluoroalkyl group having 1 to 50 carbon atoms represented by R and Ra may include a perfluoroalkyl group such as a trifluoromethyl group, a pentafluoroethyl group, a heptafluoropropyl group and a heptadecafluorooctane group, a monofluoromethyl group, a difluoromethyl group, a trifluoroethyl group, a tetrafluoropropyl group, an octafluoropentyl group, etc.

Examples of the substituted or unsubstituted alkyl group having 1 to 50 carbon atoms represented by R and Ra may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

The substituted or unsubstituted alkoxy group having 1 to 50 carbon atoms represented by R and Ra may be a group represented by —OY. Examples of Y may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, etc.

Examples of the halogen atom represented by R and Ra may include fluorine (F), chlorine (Cl), bromine (Br), iodine (I), etc.

Here, example compounds of the electron accepting material may include the following Compounds 4-15 and 4-16.

For example, the LUMO level of Compound 4-15 may be about −4.40 eV, and the LUMO level of Compound 4-16 may be about −5.20 eV. However, the electron accepting material is not limited to the following Compounds 4-15 and 4-16.

Formula 6

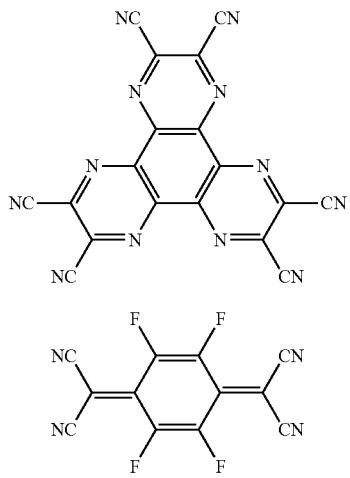

(4-15)

(4-16)

(2-1-1-2. Configuration of Intermediate Hole Transport Material Layer)

The intermediate hole transport material layer 133 may include an intermediate hole transport material. The intermediate hole transport material layer 133 may be formed, for example, on the anode-side hole transport layer 131.

The intermediate hole transport material included in the intermediate hole transport material layer 133 may be any suitable hole transport materials. Examples of the intermediate hole transport material included in the intermediate hole transport material layer 133 may be TAPC, a carbazole derivative (such as N-phenyl carbazole or polyvinyl carbazole), TPD, TCTA, NPB, etc.

However, the intermediate hole transport material may be a compound represented by the following Formula 2.

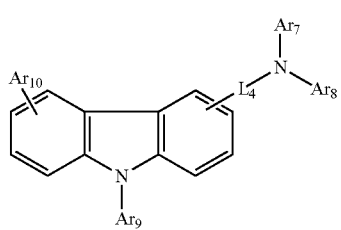

Formula 2

In Formula 2, $Ar_7$ to $Ar_9$ are each independently a substituted or unsubstituted aryl group having 6 to 50 carbon atoms for forming a ring or a substituted or unsubstituted heteroaryl group having 5 to 50 carbon atoms for forming a ring.

$Ar_{10}$ is hydrogen, deuterium, a halogen atom, a substituted or unsubstituted aryl group having 6 to 50 carbon atoms for forming a ring, a substituted or unsubstituted heteroaryl group having 5 to 50 carbon atoms for forming a ring or a substituted or unsubstituted alkyl group having 1 to 50 carbon atoms.

$L_4$ is a direct linkage, a substituted or unsubstituted arylene group having 6 to 18 carbon atoms for forming a ring or a substituted or unsubstituted heteroarylene group having 5 to 15 carbon atoms for forming a ring.

Examples of $Ar_7$ to $Ar_9$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In one embodiment, examples of $Ar_7$ to $Ar_9$ may include the phenyl group, the biphenyl group, the terphenyl group, the fluorenyl group, the carbazolyl group, the dibenzofuranyl group, etc.

Examples of $Ar_{10}$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In one embodiment, examples of $Ar_{10}$ may include the phenyl group, the biphenyl group, the terphenyl group, the fluorenyl group, the carbazolyl group, the dibenzofuranyl group, etc.

Examples of $L_4$ other than the direct linkage may include a phenylene group, a biphenylene group, a terphenylene group, a naphthalene group, an anthrylene group, a phenanthrylene group, a fluorenylene group, an indenylene group, a pyrenylene group, an acetonaphthenylene group, a fluoranthenylene group, a triphenylenylene group, a pyridylene group, a furanylene group, a pyranylene group, a thienylene group, a quinolylene group, an isoquinolylene group, a benzofuranylene group, a benzothienylene group, an indolylene group, a carbazolylene group, a benzoxazolylene group, a benzothiazolylene group, a kinokisariren group, a benzoimidazolylene group, a pyrazolylene group, a dibenzofuranylene group, a dibenzothienylene group, etc. In one embodiment, $L_4$ may include the direct linkage, the phenylene group, the biphenylene group, the terphenylene group, the fluorenylene group, the carbazolylene group or the dibenzofuranylene group.

Examples of the compound represented by Formula 2 may include the following Compounds 2-1 to 2-17. However, the compound represented by Formula 2 is not limited to the following Compounds 2-1 to 2-17.

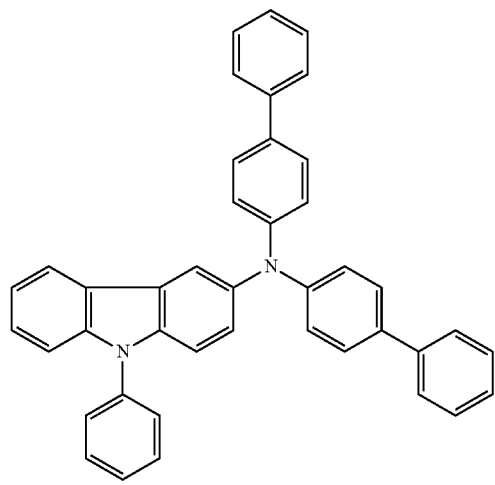
(2-1)
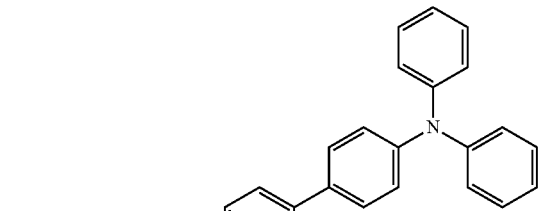
(2-4)
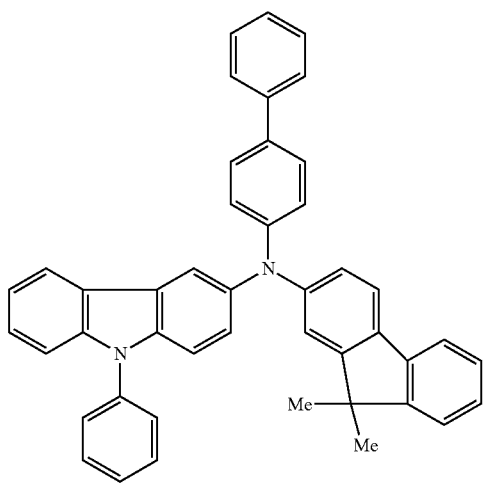
(2-2)
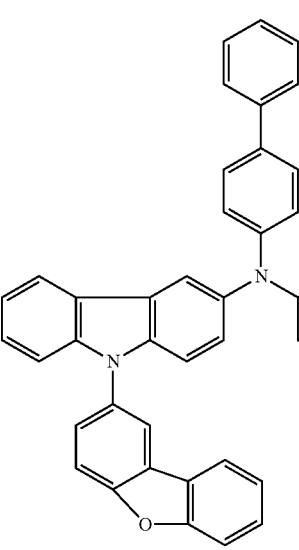
(2-5)
(2-3)
(2-6)

-continued
(2-7)
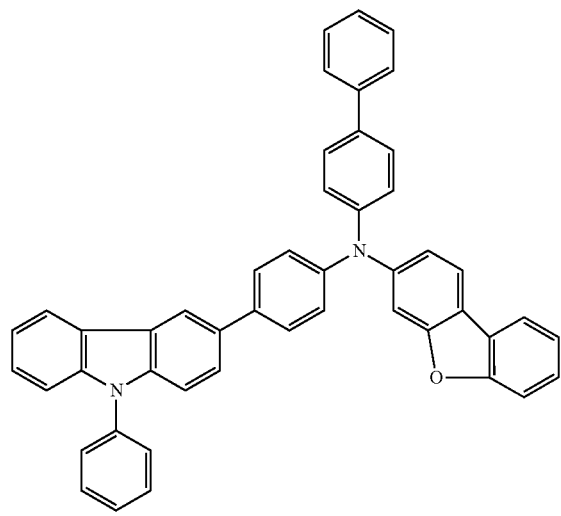
(2-8)
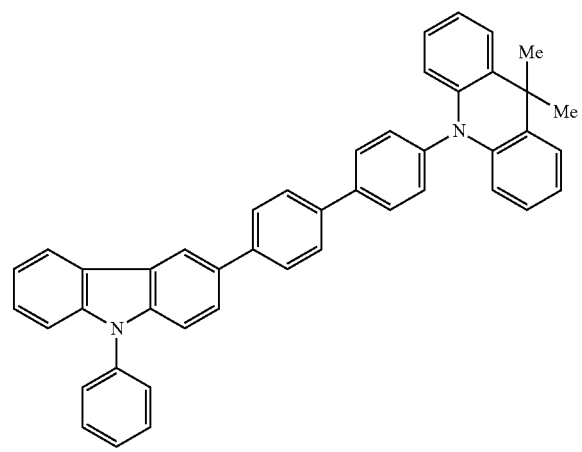
(2-9)
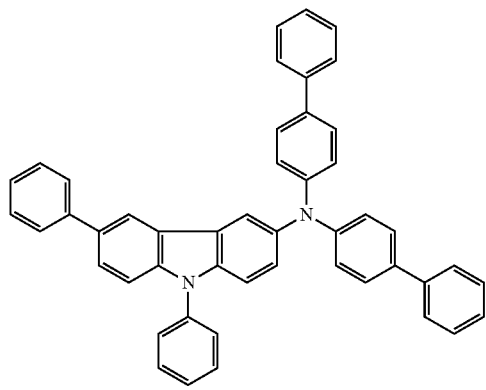
-continued
(2-10)
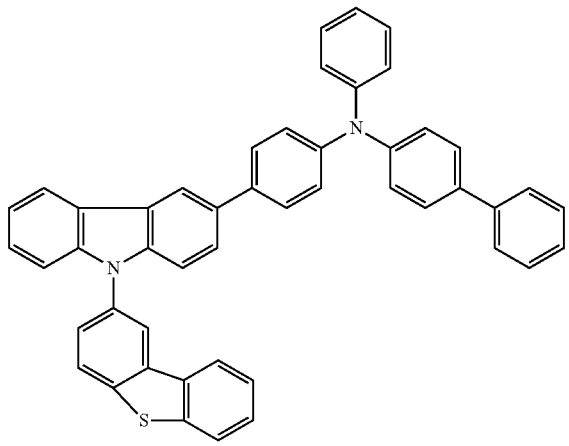
(2-11)
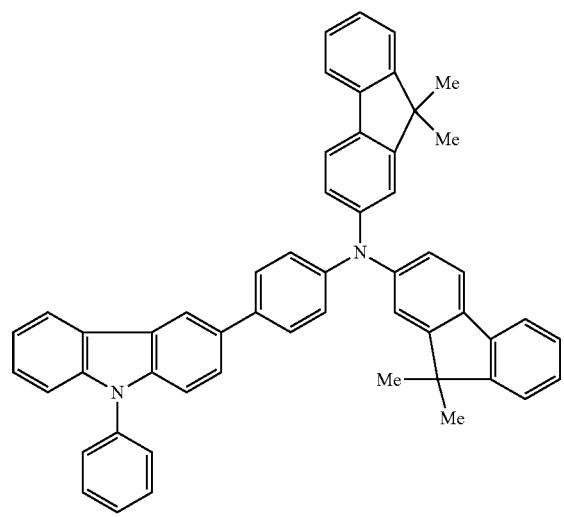
(2-12)
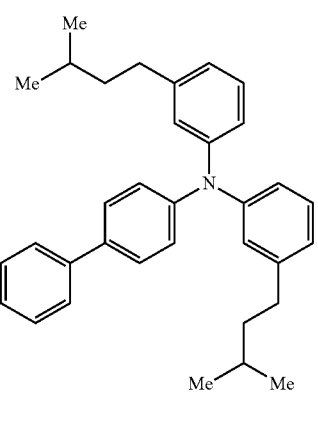

-continued (2-13)
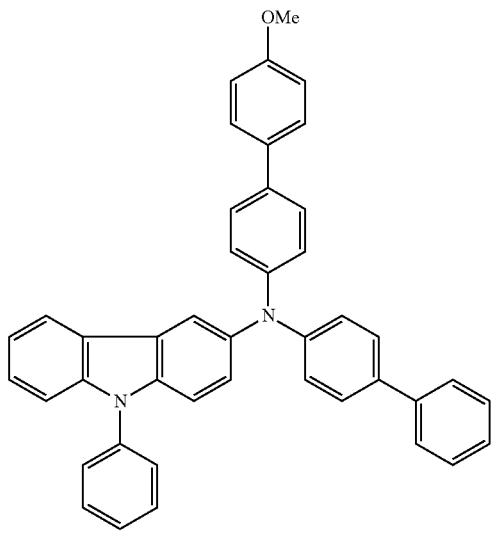

(2-14)
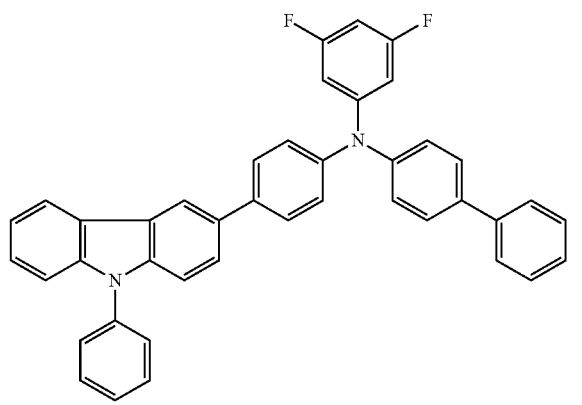

(2-15)
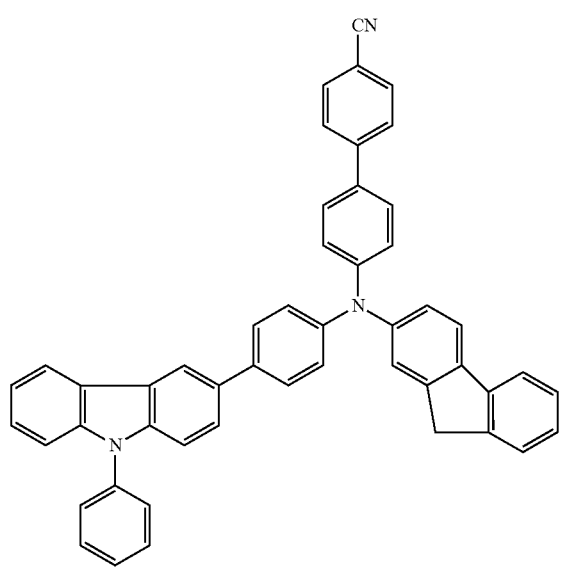

-continued (2-16)
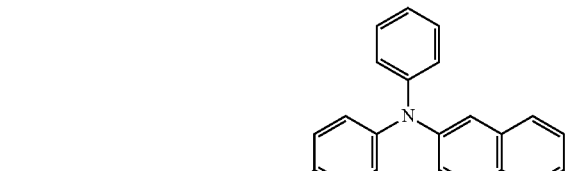

(2-17)
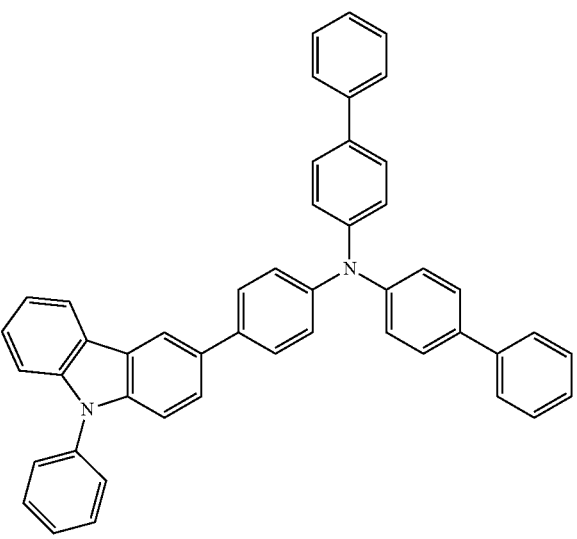

The intermediate hole transport material layer 133 may include the compound represented by the above Formula 2 as the intermediate hole transport material, and may improve the hole transporting property of the hole transport layer 130. Thus, the driving voltage of the organic EL device 100 may decrease, and the emission efficiency and emission life thereof may be increased.

(2-1-1-3. Configuration of Emission Layer-Side Hole Transport Layer)

The emission layer-side hole transport layer 135 may include a compound represented by the following Formula 1. The emission layer-side hole transport layer 135 may be formed, for example, on the intermediate hole transport material layer 133, adjacent to the emission layer 140.

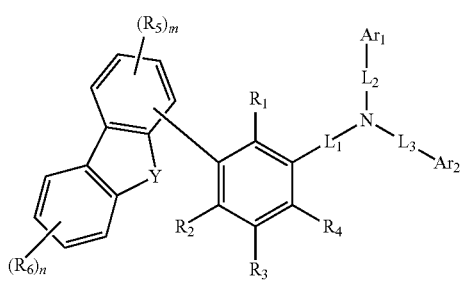

Formula 1

In Formula 1, Y is O or S, $R_1$ to $R_6$ are each independently hydrogen, deuterium, a halogen atom, a substituted or unsubstituted alkyl group having 1 to 15 carbon atoms, a substituted or unsubstituted silyl group, a substituted or unsubstituted aryl group having 6 to 30 carbon atoms for forming a ring, a substituted or unsubstituted heteroaryl group having 1 to 30 carbon atoms for forming a ring, or a substituted or unsubstituted aryl group or heteroaryl group formed via condensation of optional adjacent substituents; $Ar_1$ and $Ar_2$ are each independently a substituted or unsubstituted aryl group having 6 to 30 carbon atoms for forming a ring, or a substituted or unsubstituted heteroaryl group having 1 to 30 carbon atoms for forming a ring; $L_1$ to $L_3$ are each independently a direct linkage, a substituted or unsubstituted alkylene group having 1 to 15 carbon atoms, a substituted or unsubstituted aralkylene group having 7 to 30 carbon atoms, a substituted or unsubstituted arylene group having 6 to 30 carbon atoms for forming a ring, a substituted or unsubstituted heteroarylene group having 1 to 30 carbon atoms for forming a ring, or a substituted or unsubstituted divalent silyl group; m is an integer from 0 to 3; and n is an integer from 0 to 4.

Examples of $R_1$ to $R_6$ may include hydrogen, deuterium, a halogen atom, a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, a methyl group, an ethyl group, a propyl group, an isopropyl group, an n-butyl group, etc. In one embodiment, examples of $R_1$ and $R_6$ may include the hydrogen atom, the halogen atom, the methyl group, the phenyl group, the biphenyl group, the fluorenyl group, the carbazolyl group, and the dibenzofuranyl group.

Examples of $Ar_1$ and $Ar_2$ may include a phenyl group, a biphenyl group, a terphenyl group, a naphthyl group, an anthryl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a pyrazolyl group, a dibenzofuranyl group, a dibenzothienyl group, etc. In one embodiment, examples of $Ar_1$ and $Ar_2$ may include the phenyl group, the biphenyl group, the terphenyl group, the fluorenyl group, the carbazolyl group, the dibenzofuranyl group, etc.

Examples of $L_1$ to $L_3$ other than the direct linkage may be a divalent substituent of the substituent illustrated in the above $Ar_1$ and $Ar_2$ (e.g., examples of $L_1$ to $L_3$ other than the direct linkage may be a corresponding divalent group of the groups listed above for $Ar_1$ and $Ar_2$). In one embodiment, examples of $L_1$ to $L_3$ other than the direct linkage may include the phenylene group, the naphthylene group, the biphenylene group, the thienothiophenylene group and the pyridylene group. $L_1$ to $L_3$ may include the direct linkage, the phenylene group and the biphenylene group.

Examples of the compound represented by Formula 1 may include the following Compounds 1 to 48. However, the compound represented by Formula 1 is not limited to the following Compounds 1 to 48.

Formula 8

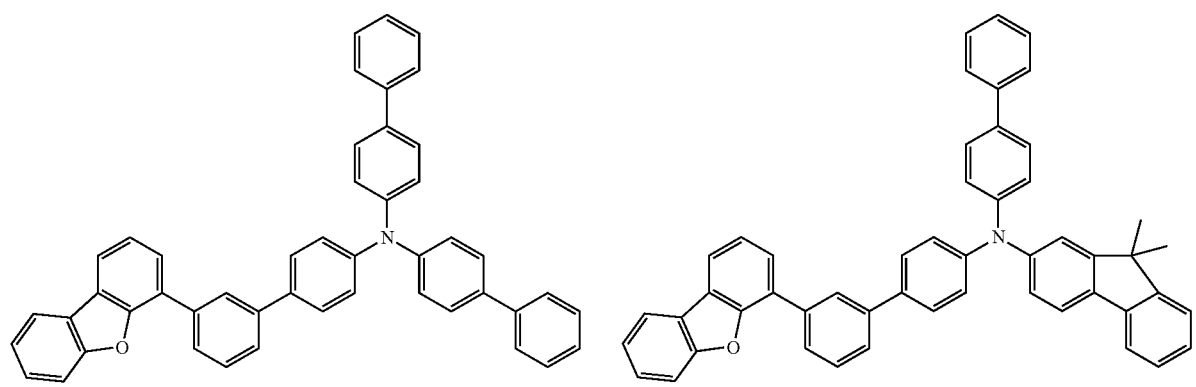

1

2

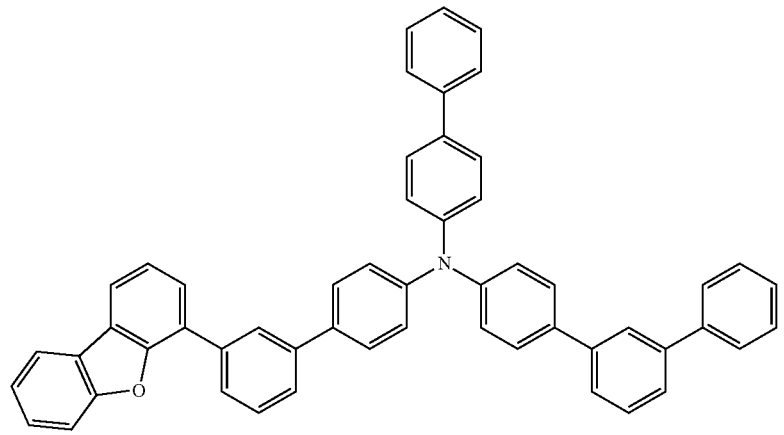
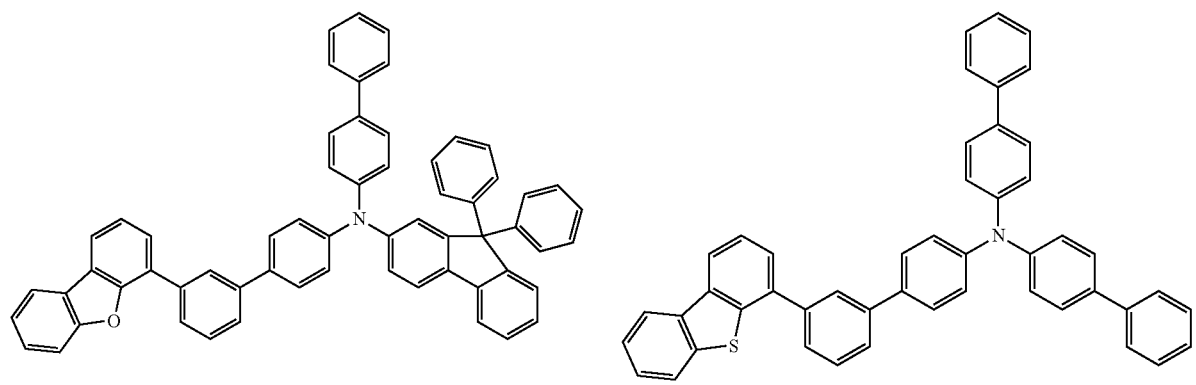
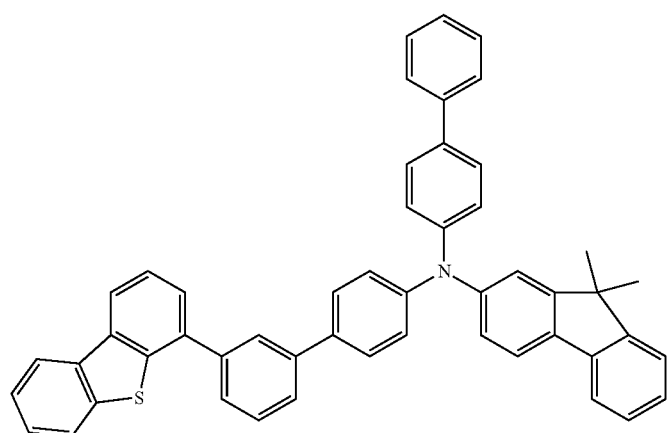

-continued
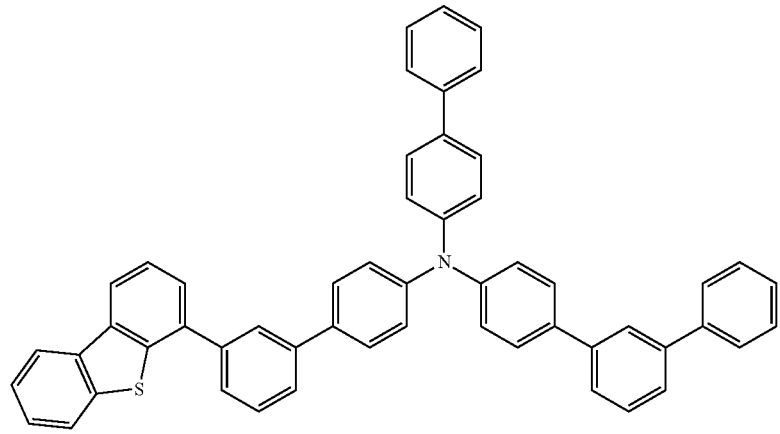
7
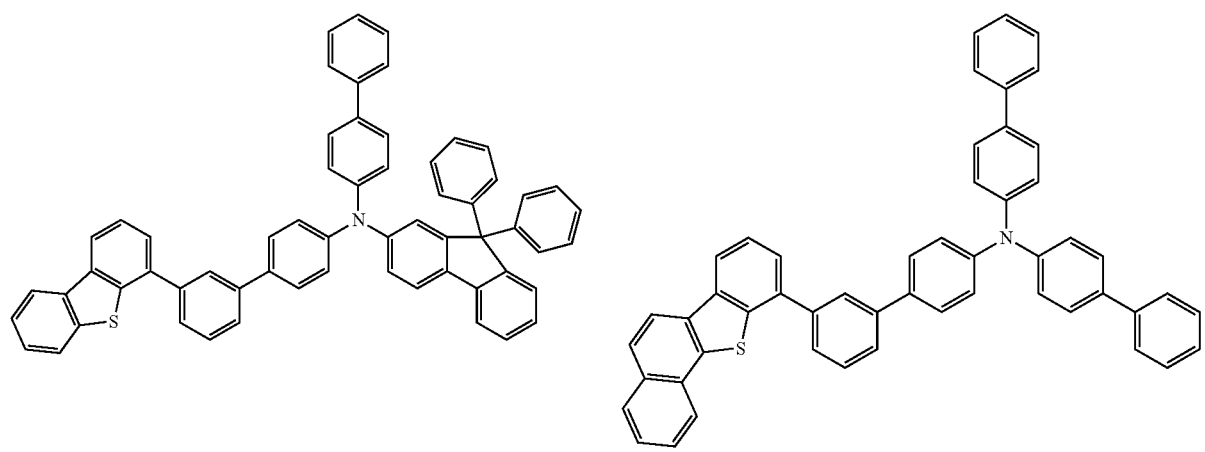
8
9
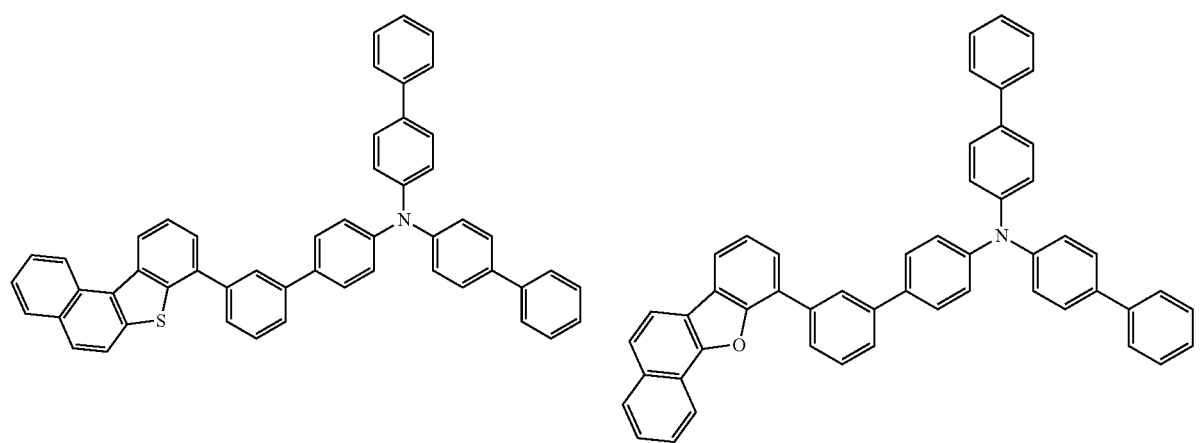
10
11

12
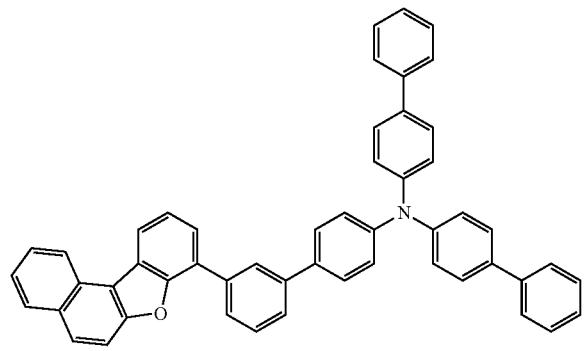
13
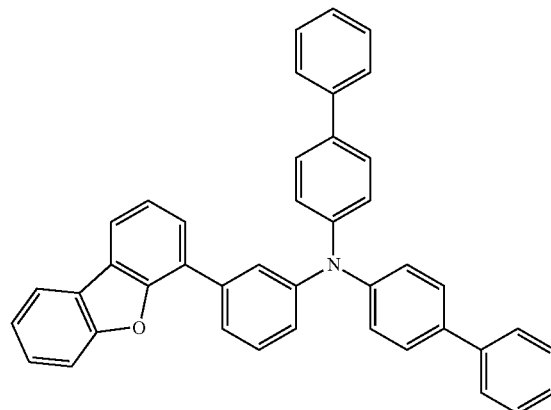
14
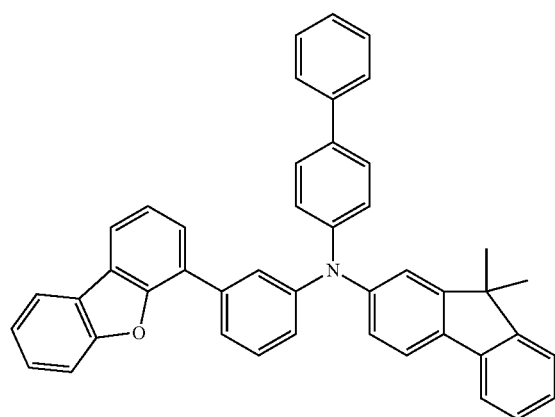
15
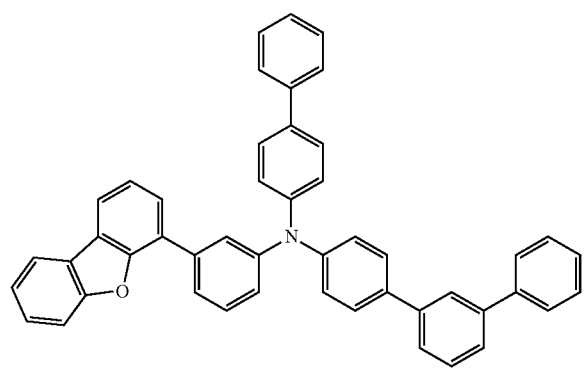
16
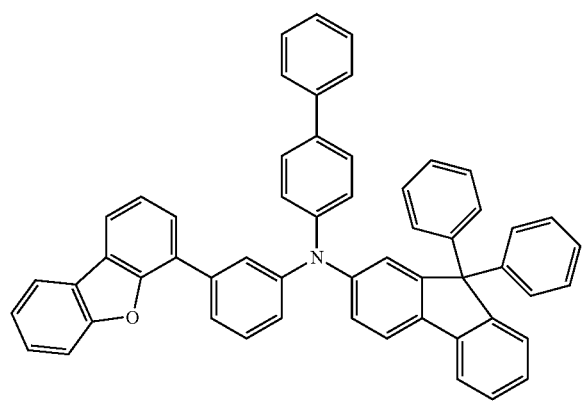
17
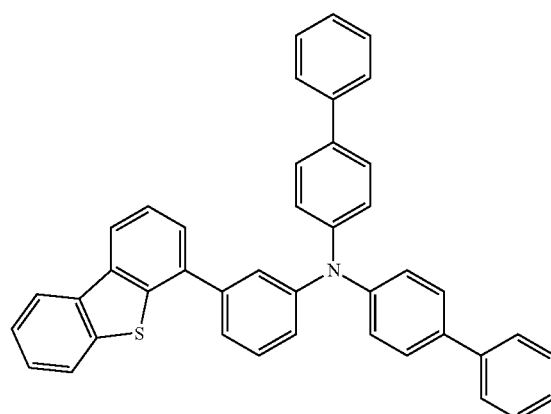

-continued
18
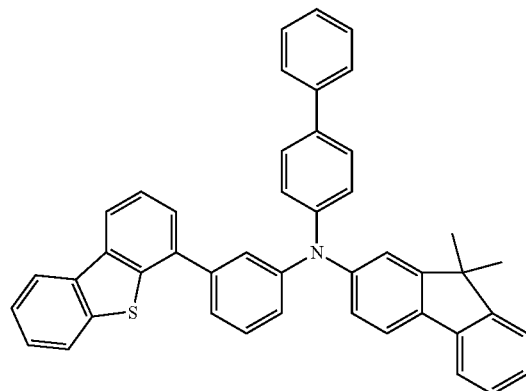
19
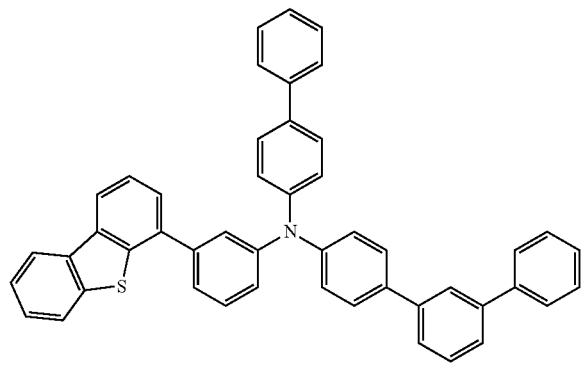
20
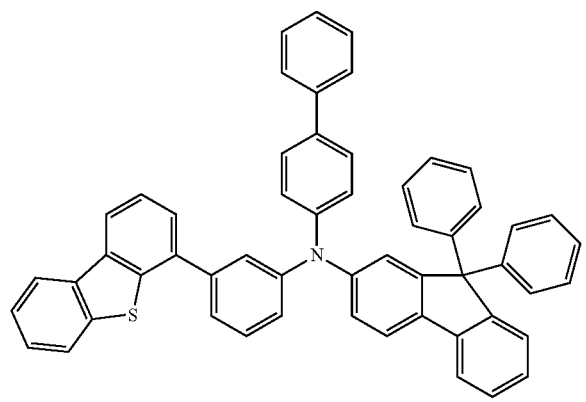
21
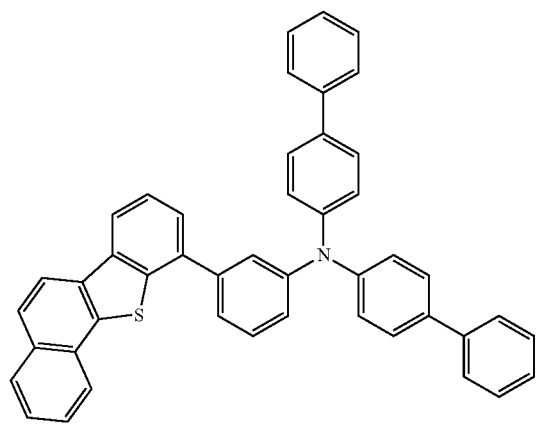
22
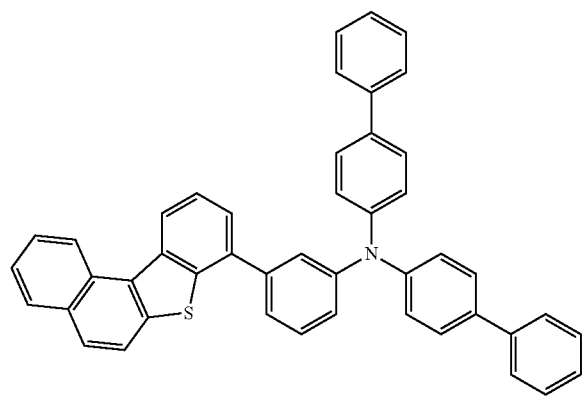
23
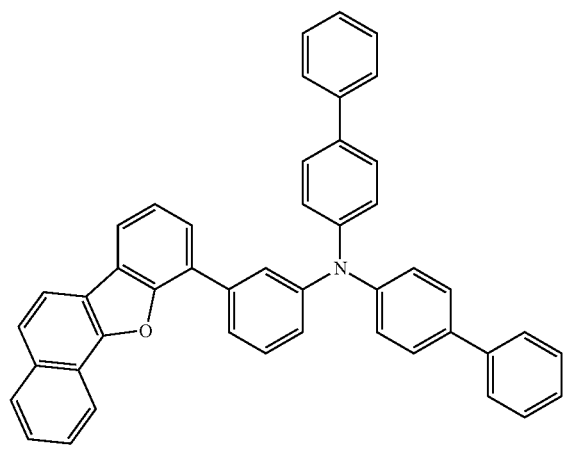

-continued
24
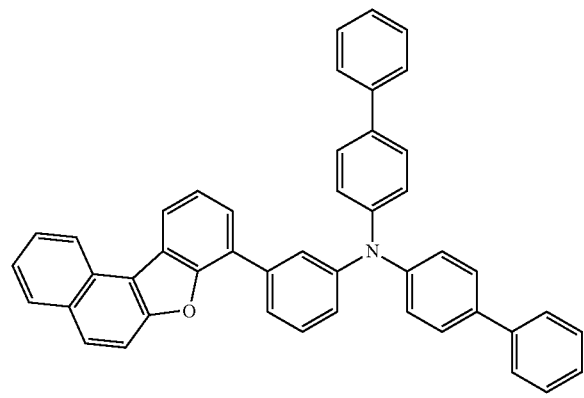
25
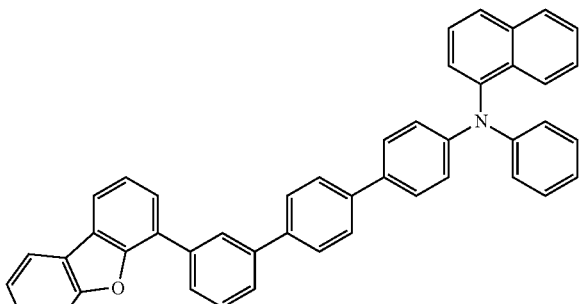
26
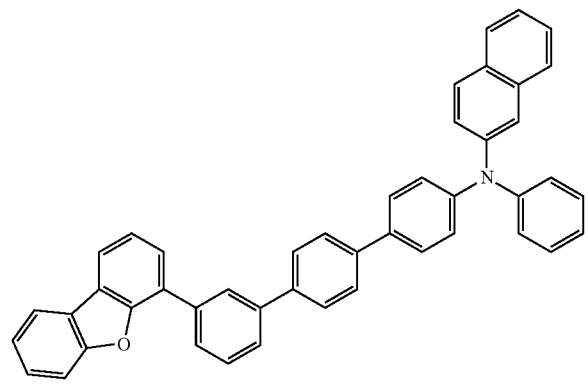
27
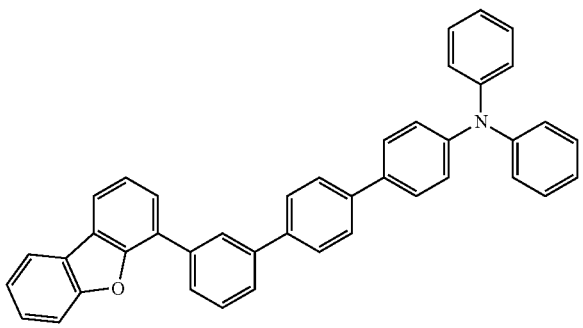
28
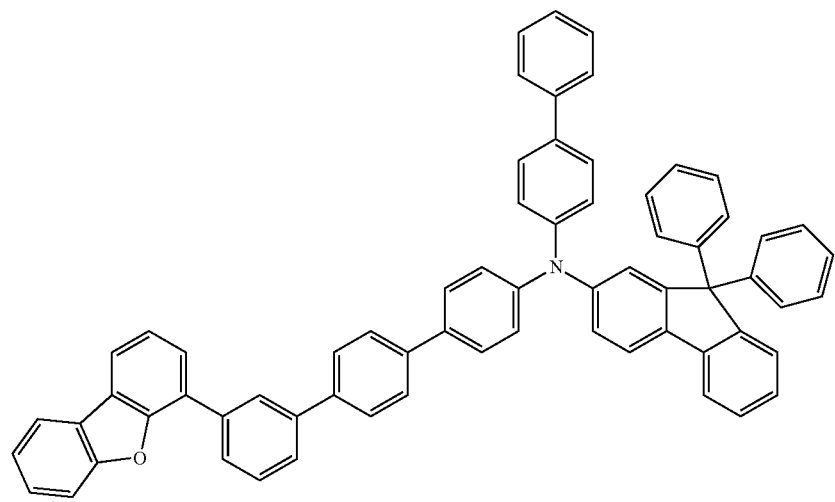

29
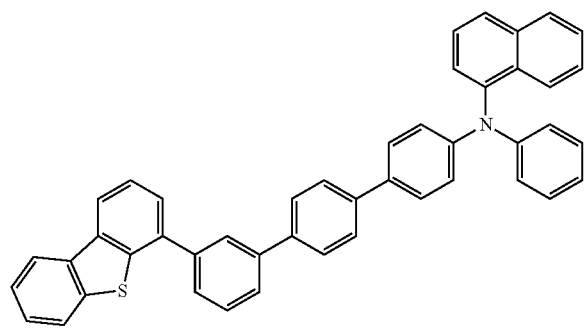
30
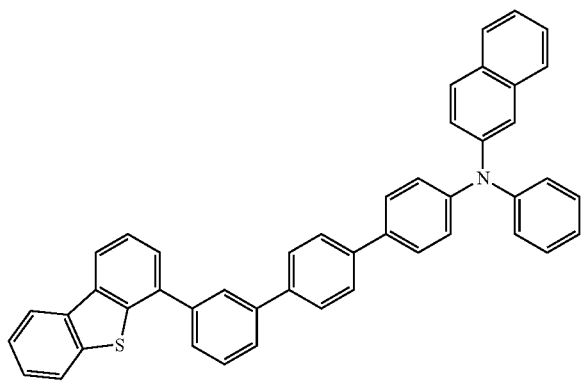
31
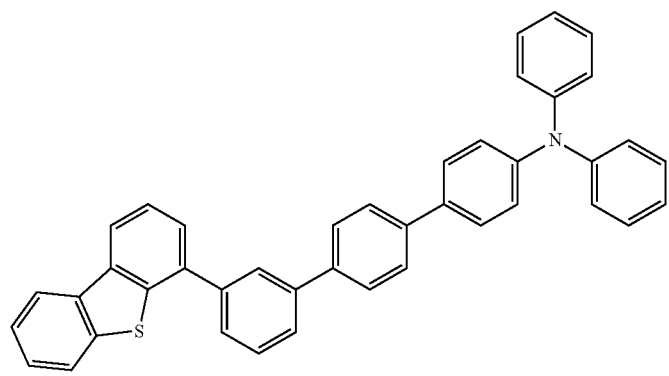
32
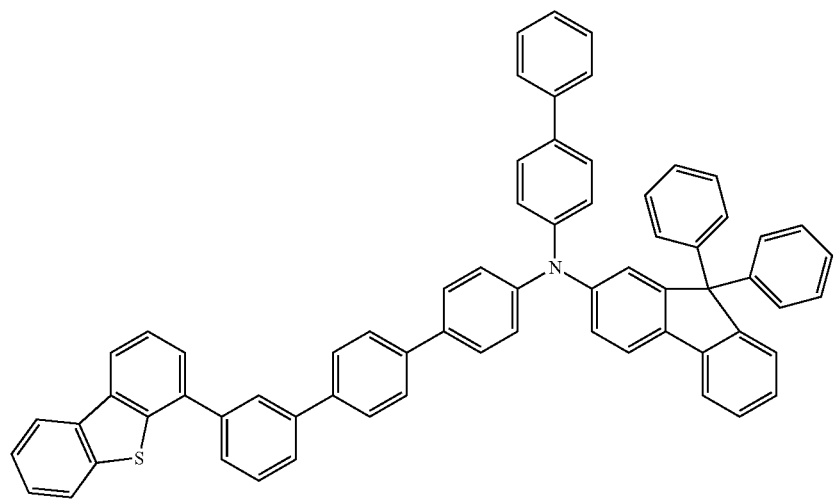

-continued
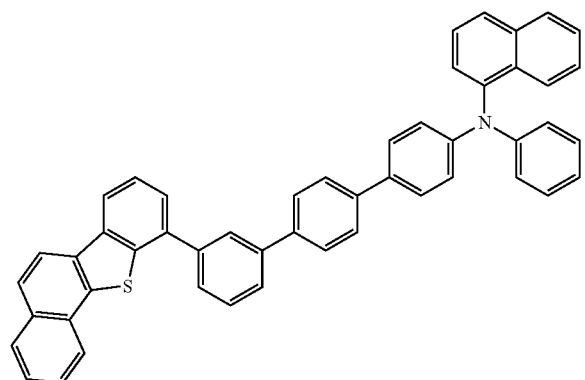
33
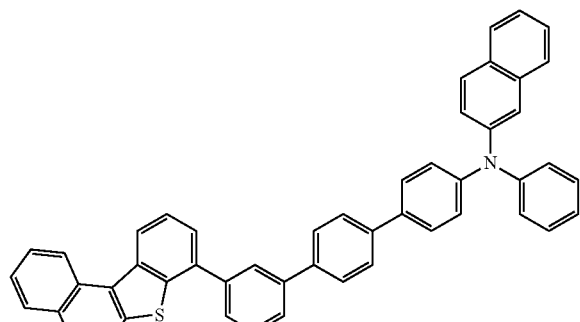
34
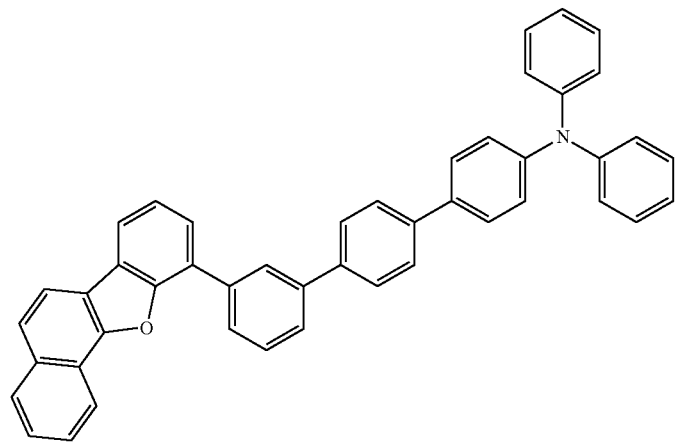
35
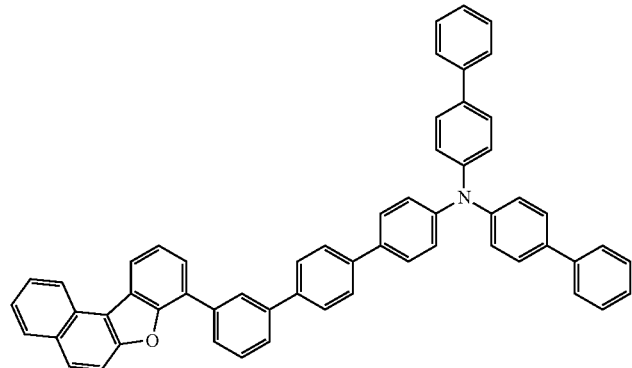
36
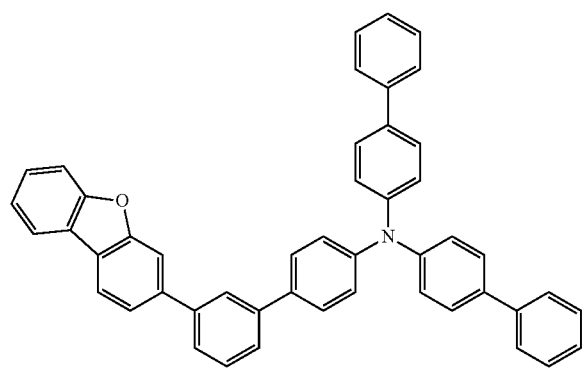
37
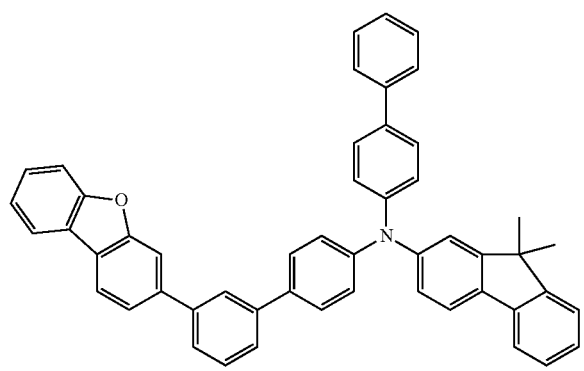
38

-continued
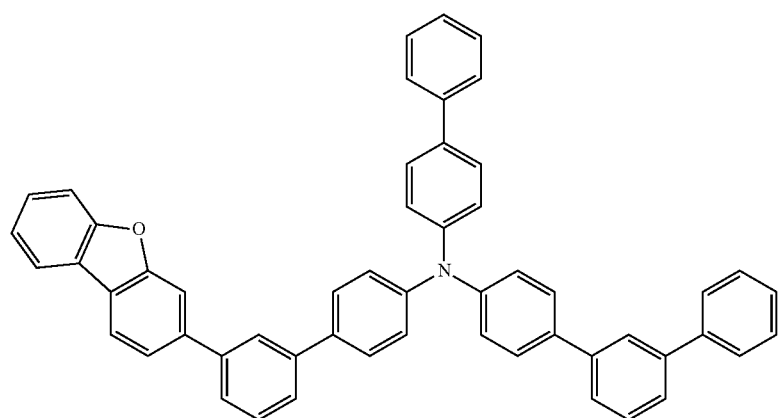
39
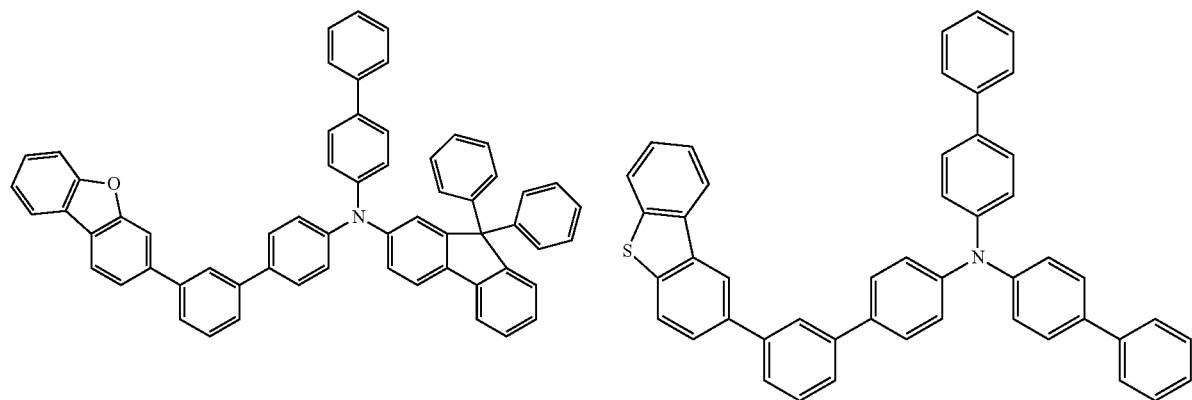
40 41
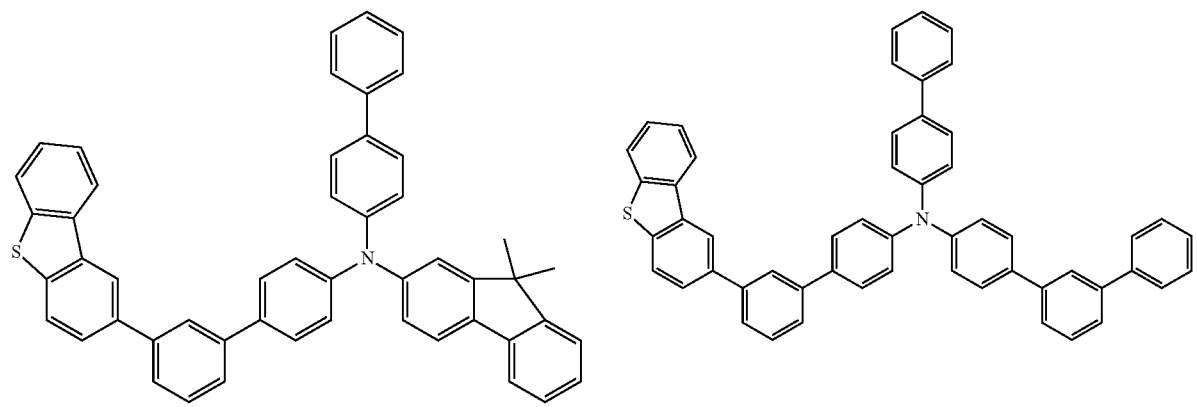
42 43

-continued
44
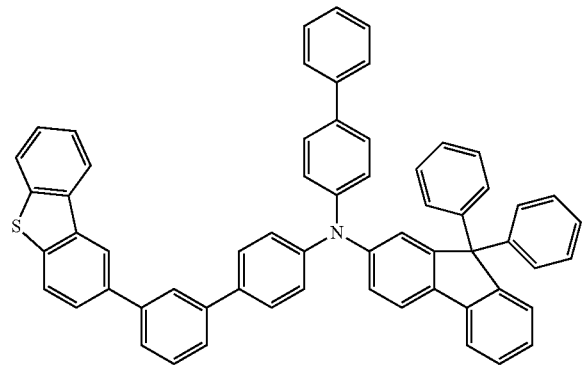
45
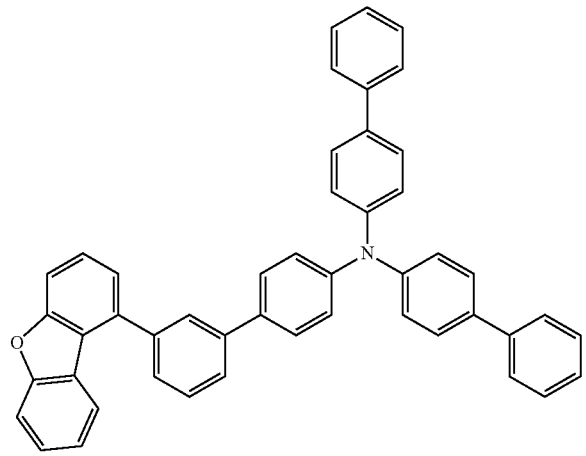
46
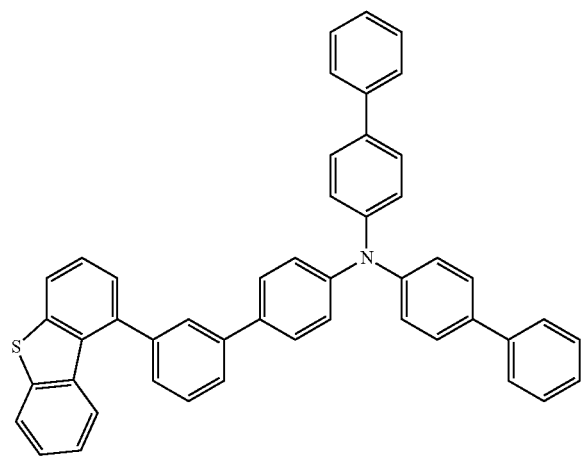
47
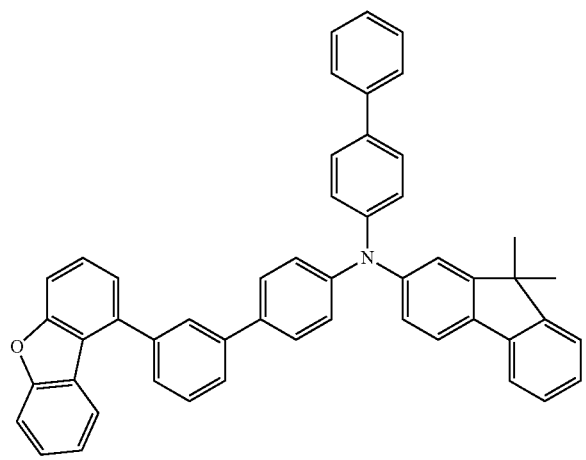
48
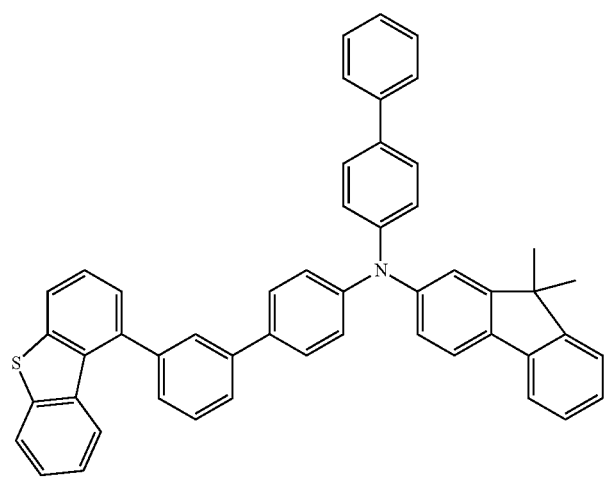

The emission layer-side hole transport layer 135 may include the compound represented by the above Formula 1 as the emission layer-side hole transport material and may passivate the hole transport layer 130 from electrons not consumed in the emission layer 140. Since the emission layer-side hole transport layer 135 includes the compound represented by Formula 1, the diffusion of energy in an excited state generated in the emission layer 140 to the hole transport layer 130 may be reduced or prevented. Thus, according to this configuration, the emission layer-side hole transport layer 135 may improve the current flow durability of the hole transport layer 130.

The emission layer-side hole transport layer 135 may be formed near the emission layer 140, and for example, may be formed adjacent to the emission layer 140 to effectively reduce or prevent the diffusion of the electrons or the energy from the emission layer 140.

Since the emission layer-side hole transport layer 135 includes the compound represented by Formula 1, the charge balance of the whole organic EL device 100 may be controlled, and the diffusion of the electron accepting material included in the anode-side hole transport layer 131 into the emission layer 140 may be restrained (e.g., reduced or prevented). Accordingly, the emission layer-side hole transport layer 135 may improve the charge transport property of the whole hole transport layer 130.

Since the emission layer-side hole transport layer 135 includes the compound represented by Formula 1, the charge transport property and current flow durability of the hole transport layer 130 may be improved. Thus, the emission layer-side hole transport layer 135 may decrease the driving voltage and improve the emission efficiency and emission life of the organic EL device 100.

As explained above, the hole transport layer 130 including the anode-side hole transport layer 131, the intermediate hole transport material layer 133 and the emission layer-side hole transport layer 135 may improve the current flow durability and hole transport property of the organic EL device 100. Thus, the driving voltage may decrease and the emission efficiency and emission life of the organic EL device 100 may be improved.

2-2. Examples

Hereinafter, organic EL devices according to example embodiments will be explained by referring to examples and comparative examples. The following embodiments are only for illustration, and the organic EL devices according to example embodiments are not limited thereto.

(2-2-1. Synthesis of Compound Represented by Formula 1)

First, a synthetic method of a compound represented by Formula 1 will be explained referring to synthetic methods of Compounds 1 and 5. The following embodiments are only for illustration, and the synthetic methods of the compound represented by Formula 1 are not limited thereto.

(2-2-1-1. Synthesis of Compound 1)

According to the following Reaction 1, Compound 1 in the following Formula 13, which is the compound represented by Formula 1 was synthesized. The product thus obtained was identified by measuring the physical properties thereof by means of $^1$HNMR and FAB-MS.

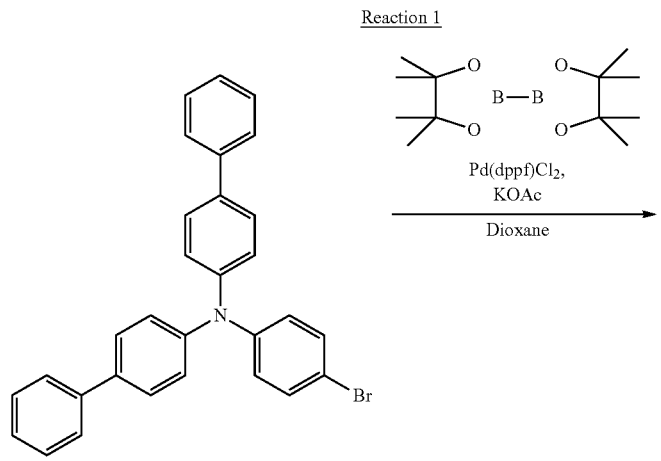

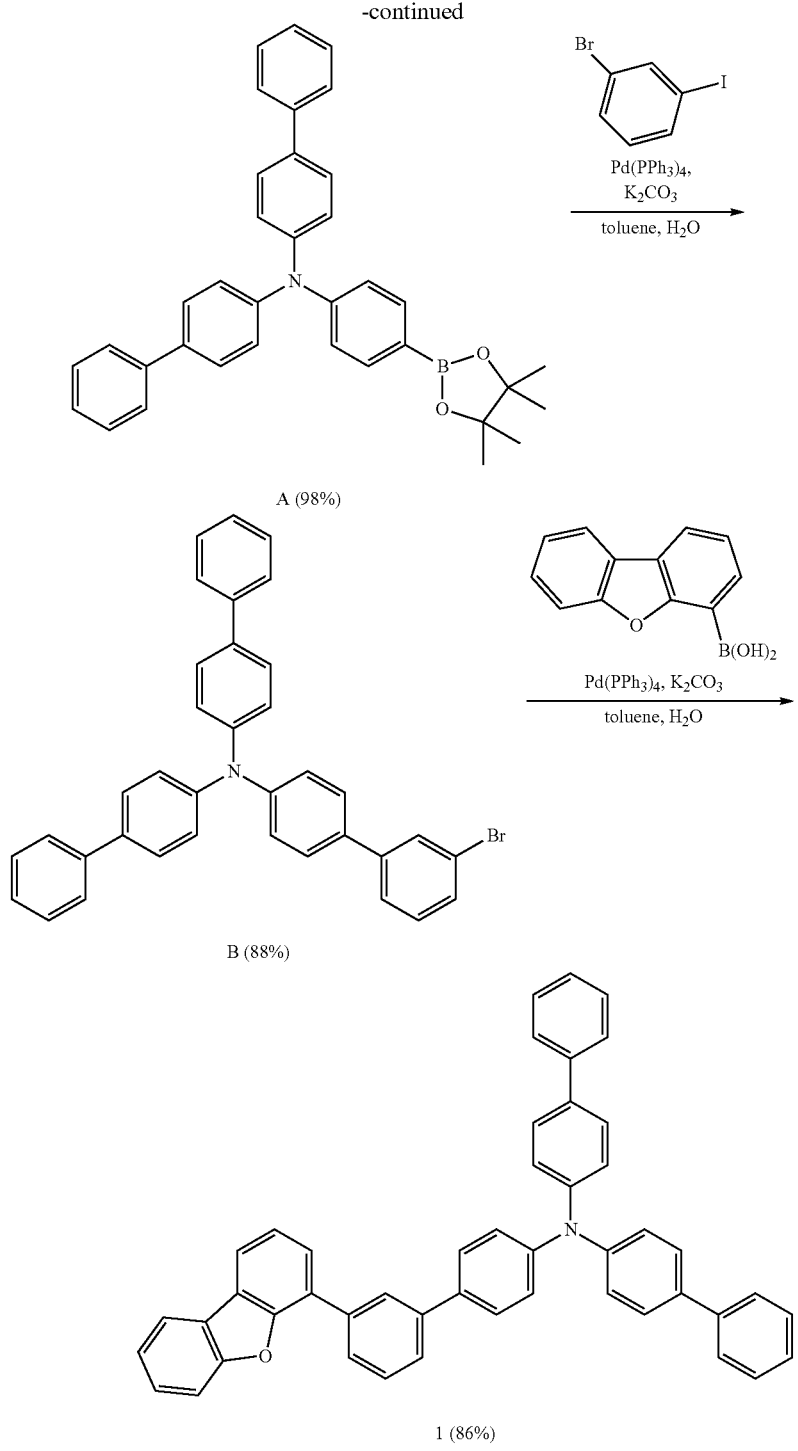

(Synthesis of Compound A)

Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$.CH$_2$Cl$_2$, 33.3 g of KOAc and 33.0 g of bis(pinacolato)diboron were added to a 2 L flask, followed by degassing under vacuum and stirring in a dioxane solvent at about 100° C. for about 12 hours. Then, the solvent was distilled from the reactant, CH$_2$Cl$_2$ and water were added thereto, and an organic phase was separated. To the separated organic phase, magnesium sulfate (Mg$_2$SO$_4$) and activated clay were added, filtering with suction was performed, and the solvent was distilled. The crude product thus obtained was separated by silica gel column chromatography utilizing a mixture solvent of dichloromethane and hexane to produce 56.8 g (Yield 98%) of Compound A as a white solid (FAB-MS: C$_{36}$H$_{34}$BNO$_2$, measured value 523).

(Synthesis of Compound B)

Under an Ar atmosphere, 10.0 g of Compound A, 6.00 g of 1-iodo-3-bromobenzene, 1.54 g of Pd(PPh$_3$)$_4$, and 5.25 g of potassium carbonate (K$_2$CO$_3$) were added to a 300 mL, three necked flask, followed by heating and stirring in a mixture solvent of 450 mL of toluene and 60 mL of water at about 90° C. for about 8 hours. After air cooling, water was added to a mixture, an organic phase was separated, and the solvents were distilled from the separated organic phase. The crude product thus obtained was separated by silica gel column chromatography utilizing a mixture solvent of dichloromethane and hexane and recrystallized utilizing a mixture solvent of toluene and hexane to produce 9.29 g (Yield 88%) of Compound B as a white solid (FAB-MS: $C_{36}H_{26}BrN$, measured value 551).

(Synthesis of Compound 1)

Under an Ar atmosphere, 3.10 g of Compound B, 1.2 g of dibenzofuran-4-boronic acid, 0.84 g of $Pd(PPh_3)_4$, and 2.35 g of potassium carbonate ($K_2CO_3$) were added to a 500 mL, three necked flask, followed by heating and stirring in a mixture solvent of 170 mL of toluene and 80 mL of water at about 90° C. for about 8 hours. After air cooling, water was added to the reactant, an organic phase was separated, and the solvents were distilled from the separated organic phase. The crude product thus obtained was separated by silica gel column chromatography utilizing a mixture solvent of dichloromethane and hexane and recrystallized utilizing a mixture solvent of toluene and hexane to produce 3.08 g (Yield 86%) of Compound 1 as a white solid. Chemical shift values (δ) of Compound 1 by $^1$HNMR (300 MHz, $CDCl_3$) were 8.11 (s, 1H), 8.00 (d, J=7.6 Hz, 1H), 7.96 (d, J=7.6 Hz, 1H), 7.87 (d, J=7.4 Hz, 1H), 7.67-7.23 (m, 29H), and the measured molecular weight of Compound 1 by FAB-MS was 639 ($C_{48}H_{33}NO$).

(2-2-1-2. Synthesis of Compound 5)

According to the following Reaction 2, Compound 5 as the compound represented by Compound 1 was synthesized. The product was identified by measuring the physical properties thereof by $^1$HNMR and FAB-MS.

Reaction 2

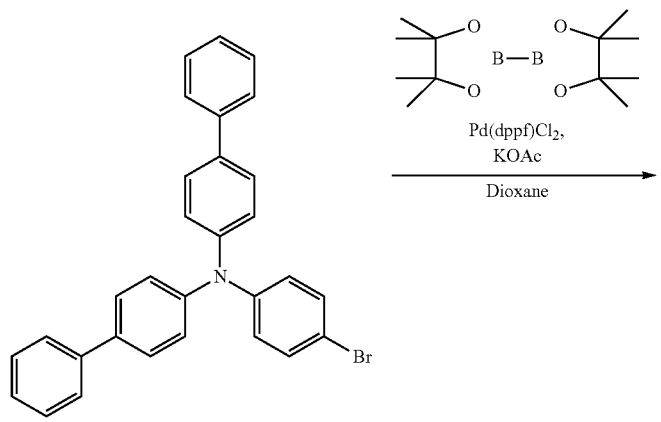

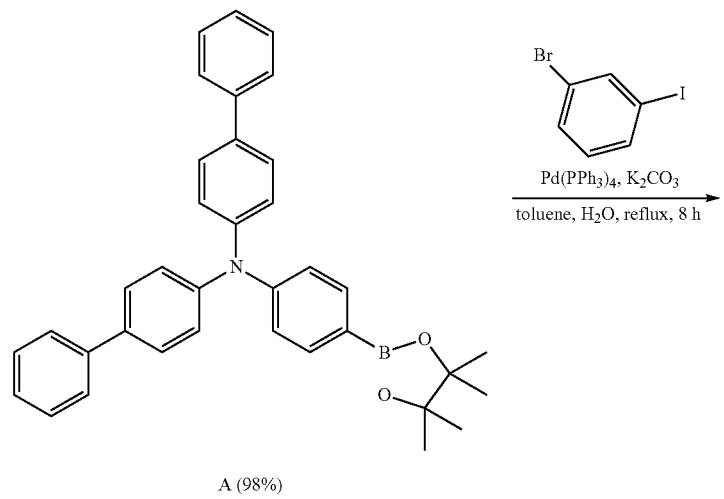

A (98%)

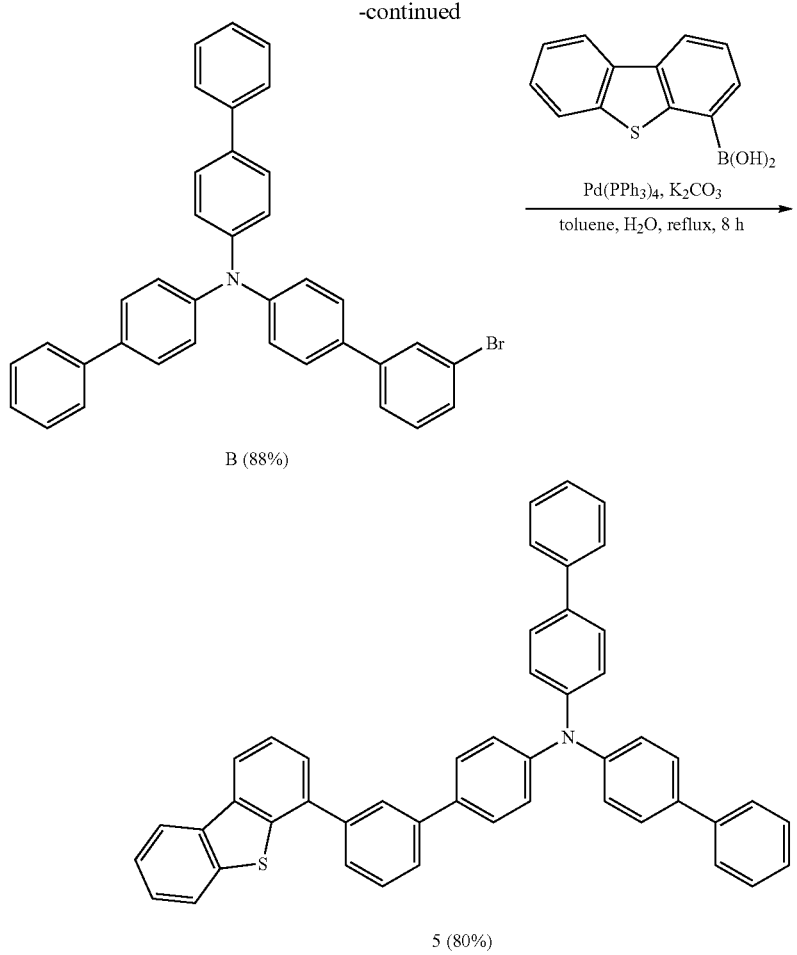

B (88%)

5 (80%)

(Synthesis of Compounds A and B)

Since the synthetic method of Compounds A and B are substantially the same as that described above (2-2-1-1. Synthesis of Compound 1), explanation thereabout will not be repeated.

(Synthesis of Compound 5)

Under an Ar atmosphere, 3.10 g of Compound B, 1.28 g of dibenzothiophene-4-boronic acid, 0.84 g of Pd(PPh$_3$)$_4$, and 2.35 g of potassium carbonate (K$_2$CO$_3$) were added to a 500 mL, three necked flask, followed by heating and stirring in a mixture solvent of 170 mL of toluene and 80 mL of water at about 90° C. for about 8 hours. After air cooling, water was added to the reactant, an organic phase was separated, and solvents were distilled from the separated organic phase. The crude product thus obtained was separated by silica gel column chromatography utilizing a mixture solvent of dichloromethane and hexane and recrystallized utilizing a mixture solvent of toluene and hexane to produce 2.94 g (Yield 80%) of Compound 5 as a white solid. Chemical shift values (δ) of Compound 5 by $^1$HNMR (300 MHz, CDCl$_3$) were 8.46-8.41 (m, 2H), 8.20 (d, 1H, J=7.80 Hz), 7.98 (d, 1H, J=7.90 Hz), 7.58-7.50 (m, 18H), 7.48-7.41 (m, 4H), 6.69-6.65 (m, 4H), and the measured molecular weight of Compound 5 by FAB-MS was 656 (C$_{48}$H$_{33}$NS).

(2-2-2. Manufacture of Organic EL Device Including Anode-Side Hole Transport Material Mainly Including Electron Accepting Material)

An organic EL device according to an embodiment was manufactured by the following manufacturing method.

First, with respect to an ITO-glass substrate patterned and washed in advance, surface treatment utilizing UV-Ozone (O$_3$) was conducted. The layer thickness of an ITO layer (first electrode) on a glass substrate was about 150 nm. After ozone treatment, the surface treated substrate was inserted in a glass bell jar type evaporator for forming an organic layer, and an anode-side hole transport layer, an intermediate hole transport material layer, an emission layer-side hole transport layer, an emission layer and an electron transport layer were evaporated one by one with a vacuum degree of about $10^{-4}$ to about $10^{-5}$ Pa. The layer thickness of each of the anode-side hole transport layer, the intermediate hole transport material layer and the emission layer-side hole transport layer was about 10 nm. The layer thickness of the emission layer was about 25 nm, and the layer thickness of the electron transport layer was about 25 nm. Then, the substrate was moved into a glass bell jar evaporator for forming a metal layer, and the electron injection layer and the second electrode were evaporated with a vacuum degree of about $10^{-4}$ to about $10^{-5}$ Pa. The layer thickness of the electron injection layer was about 1 nm and the layer thickness of the second electrode was about 100 nm.

Here, the anode-side hole transport layer, the intermediate hole transport material layer and the emission layer-side hole transport layer correspond to the hole transport layer with a stacked structure. The anode-side hole transport layer, the intermediate hole transport material layer and the emission layer-side hole transport layer were manufactured in examples and comparative examples utilizing the materials shown in the following Table 2.

In Table 2, Compounds 6-1 and 6-2 represented by the following formulae are referred to as common hole transport materials.

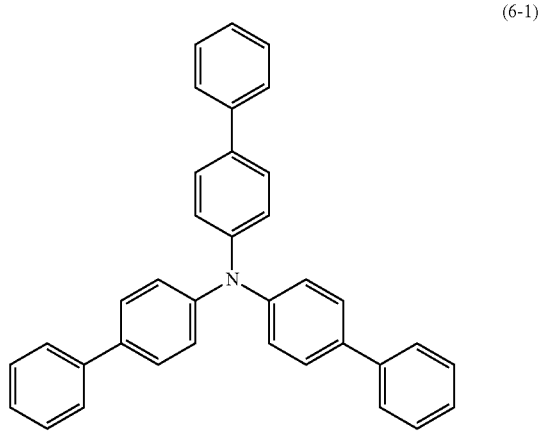

(6-1)

Alq3, the electron injection layer was formed utilizing LiF, and the second electrode was formed utilizing aluminum (Al).

(2-2-2. Evaluation Results)

Then, the driving voltage, emission efficiency and half life of the organic EL device thus manufactured were evaluated. Evaluation results are shown together in the following Table 2. The driving voltage and the emission efficiency in each example and comparative example were obtained by measuring at current density of about 10 mA/cm$^2$. The emission life was obtained by measuring a time period for decreasing luminance to half from the initial luminance of about 1,000 cd/m$^2$.

The measurement was conducted utilizing a source meter of 2400 series of Keithley Instruments Co., a Color brightness photometer CS-200 (Konica Minolta holdings Co., Ltd., measurement angle of 1°), and a PC program LabVIEW8.2 (National instruments Co., Ltd. in Japan) in a dark room.

TABLE 2

| | Anode-side hole transport layer | Intermediate hole transport material layer | Emission layer-side hole transport layer | Driving voltage [V] | Emission efficiency [cd/A] | Life $LT_{50}$ (h) |
|---|---|---|---|---|---|---|
| Example 2-1 | Compound 4-15 | Compound 2-3 | Compound 1 | 6.3 | 7.6 | 4,100 |
| Example 2-2 | Compound 4-15 | Compound 2-3 | Compound 5 | 6.3 | 7.6 | 4,100 |
| Example 2-3 | Compound 4-16 | Compound 2-3 | Compound 1 | 6.5 | 7.5 | 3,900 |
| Example 2-4 | Compound 4-15 | Compound 2-17 | Compound 1 | 6.3 | 7.6 | 3,800 |
| Example 2-5 | Compound 4-15 | Compound 6-2 | Compound 1 | 6.4 | 7.6 | 3,200 |
| Comparative Example 2-1 | Compound 4-15 | Compound 1 | Compound 2-3 | 6.8 | 7.3 | 2,100 |
| Comparative Example 2-2 | Compound 2-3 | Compound 2-3 | Compound 1 | 7.9 | 6.9 | 2,100 |
| Comparative Example 2-3 | Compound 4-15 | Compound 2-3 | Compound 6-1 | 6.9 | 7.4 | 2,300 |

-continued

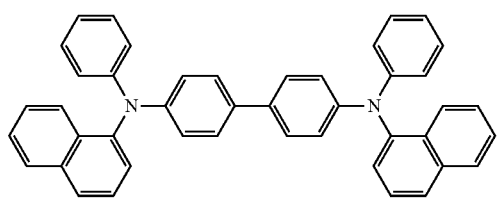

(6-2)

As the host material of the emission layer, 9,10-di(2-naphthyl)anthracene (ADN, Compound 3-2) was utilized, and as a dopant material, 2,5,8,11-tetra-t-butylperylene (TBP) was utilized. 3 wt % of the dopant material on the basis of the amount of the host material was added. In addition, the electron transport layer was formed utilizing Referring to Table 2, the driving voltage may decrease, the emission efficiency may be improved, and the emission life may be increased for Examples 2-1 to 2-5 when compared to those for Comparative Examples 2-1 to 2-3. Thus, it would be desirable that the emission life of the organic EL device may be increased by providing the anode-side hole transport layer, the intermediate hole transport material layer and the emission layer-side hole transport layer between the first electrode and the emission layer.

For example, if comparing Examples 2-1 to 2-5 with Comparative Example 2-3, the properties for Examples 2-1 to 2-5 were better. In Comparative Example 2-3, the emission layer-side hole transport material included in the emission layer-side hole transport layer was not Compound 1 or 5 represented by Formula 1, but a common hole transport material, i.e., Compound 6-1. Thus, it would be desirable that the emission layer-side hole transport layer included the compound represented by Formula 1.

If comparing Example 2-1 with Comparative Example 2-1, the properties for Example 2-1 were better. In Comparative Example 2-1, compounds included in the intermediate hole transport material layer and the emission layer-side hole transport layer were changed from those utilized in Example 2-1. Thus, it would be desirable that the emission layer-side hole transport layer including the compound represented by Formula 1 was adjacent to the emission layer.

If comparing Examples 2-1 to 2-5 with Comparative Example 2-2, the properties for Examples 2-1 to 2-5 were better. In Comparative Example 2-2, the anode-side hole transport layer did not include the electron accepting material (Compound 4-15 or 4-16) but Compound 2-3 represented by Formula 2. Thus, it would be desirable that the anode-side hole transport layer was formed mainly utilizing the electron accepting material.

If comparing Examples 2-1 to 2-4 with Example 2-5, the properties for Examples 2-1 to 2-4 were better. In Example 2-5, the intermediate hole transport material included in the intermediate hole transport material layer was not Compound 2-3 to 2-17 represented by Formula 2 but a common hole transport material, i.e., Compound 6-2. Thus, it would be desirable that the intermediate hole transport material layer may include the compound represented by Formula 2.

As described above, since an anode-side hole transport layer formed mainly utilizing an electron accepting material, an intermediate hole transport material layer and an emission layer-side hole transport layer including a compound represented by Formula 1 were stacked between a first electrode (anode) and an emission layer according to an embodiment, the driving voltage of an organic EL device may decrease, and the emission efficiency and emission life thereof may be improved.

By disposing the emission layer-side hole transport layer including the compound represented by Formula 1, the emission layer-side hole transport layer may passivate the hole transport layer from electrons not consumed in the emission layer, the diffusion of energy in an excited state generated in the emission layer into the hole transport may be reduced or prevented, and the charge balance of a whole device may be controlled. In addition, the results show that the emission layer-side hole transport layer restrained (e.g., reduced or prevented) the diffusion of the electron accepting material included in the anode-side hole transport layer provided near the first electrode (anode) by disposing the emission layer-side hole transport layer including the compound represented by Formula 1.

As described above, an anode side hole transport layer, an intermediate hole transport material layer, and an emission layer side hole transport layer are provided between an anode and an emission layer according to the present disclosure, and the emission efficiency and emission life of an organic EL device may be increased.

Expressions such as "at least one of," when preceding a list of elements, modify the entire list of elements and do not modify the individual elements of the list. Further, the use of "may" when describing embodiments of the inventive concept refers to "one or more embodiments of the inventive concept." Also, the term "exemplary" is intended to refer to an example or illustration.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

The above-disclosed subject matter is to be considered illustrative and not restrictive, and the appended claims are intended to cover all such modifications, enhancements, and other embodiments, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. An organic electroluminescent (EL) device, comprising:
    an anode;
    an emission layer; and
    a hole transport layer between the anode and the emission layer;
    wherein the hole transport layer comprises a hole transport material represented by Formula 1:

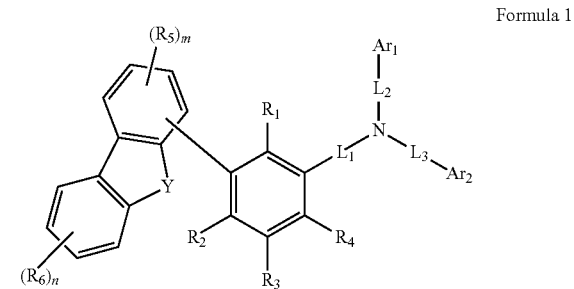

Formula 1 wherein in Formula 1, Y is O or S;
$R_1$ to $R_6$ are each independently hydrogen, deuterium, a halogen atom, a substituted or unsubstituted alkyl group having 1 to 15 carbon atoms, a substituted or unsubstituted silyl group, a substituted or unsubstituted aryl group having 6 to 30 carbon atoms for forming a ring, a substituted or unsubstituted heteroaryl group having 1 to 30 carbon atoms for forming a ring, or a substituted or unsubstituted aryl group or heteroaryl group formed via condensation of optional adjacent substituents;
$Ar_1$ and $Ar_2$ are each independently a substituted or unsubstituted aryl group having 6 to 30 carbon atoms for forming a ring, and each of $Ar_1$ and $Ar_2$ is not a heteroaryl-containing group;
$L_1$ to $L_3$ are each independently a direct linkage, a substituted or unsubstituted alkylene group having 1 to 15 carbon atoms, a substituted or unsubstituted aralkylene group having 7 to 30 carbon atoms, a substituted or unsubstituted arylene group having 6 to 30 carbon atoms for forming a ring, a substituted or unsubstituted heteroarylene group having 1 to 30 carbon atoms for forming a ring, or a substituted or unsubstituted divalent silyl group;

m is an integer from 0 to 3, and n is an integer from 0 to 4.

2. The organic EL device of claim 1, wherein the hole transport layer comprises an anode-side hole transport layer between the anode and the emission layer;
an intermediate hole transport material layer between the anode-side hole transport layer and the emission layer; and
an emission layer-side hole transport layer between the intermediate hole transport material layer and the emission layer.

3. The organic EL device of claim 2, wherein at least one of the intermediate hole transport material layer or the anode-side hole transport layer comprises a compound represented by Formula 2:

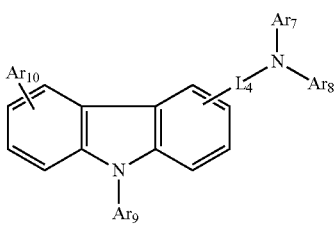

Formula 2 wherein in Formula 2, $Ar_7$ to $Ar_9$ are each independently a substituted or unsubstituted aryl group having 6 to 50 carbon atoms for forming a ring, or a substituted or unsubstituted heteroaryl group having 5 to 50 carbon atoms for forming a ring;

$Ar_{10}$ is hydrogen, deuterium, a halogen atom, a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; and $L_4$ is a direct linkage, a substituted or unsubstituted arylene group having 6 to 18 carbon atoms for forming a ring, or a substituted or unsubstituted heteroarylene group having 5 to 15 carbon atoms for forming a ring.

4. The organic EL device of claim 2, wherein the anode-side hole transport layer comprises an anode-side hole transport material and doped with an electron accepting material, and
the electron accepting material has a lowest unoccupied molecular orbital (LUMO) level within a range from about −9.0 eV to about −4.0 eV.

5. The organic EL device of claim 2, wherein the anode-side hole transport layer comprises an electron accepting material as a main component, and
the electron accepting material has a lowest unoccupied molecular orbital (LUMO) level within a range from about −9.0 eV to about −4.0 eV.

6. The organic EL device of claim 1, wherein the emission layer comprises a compound represented by Formula 3:

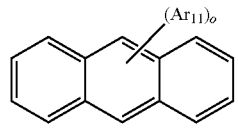

Formula 3 wherein in Formula 3, $Ar_{11}$ is each independently hydrogen, deuterium, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group, or a hydroxyl group; and o is an integer from 1 to 10.

* * * * *